US011186572B2

(12) United States Patent
Potempa et al.

(10) Patent No.: US 11,186,572 B2
(45) Date of Patent: Nov. 30, 2021

(54) BACTERIAL GLUTAMINYL CYCLASES AND INHIBITORS THEREOF FOR USE IN THE TREATMENT OF PERIODONTITIS

(71) Applicant: Fraunhofer-Gesellschaft zur Forderung der Angewandten Forschung E.V., Munich (DE)

(72) Inventors: Jan Potempa, Cracow (PL); Sigrun Eick, Bolligen (CH); Nadine Taudte, Halle (DE); Jens-Ulrich Rahfeld, Seegebiet Mansfelder Land (DE); Mirko Buchholz, Halle (DE); Hans-Ulrich Demuth, Halle (DE)

(73) Assignee: Fraunhofer-Gesellschaft zur Forderung der Angewandten Forschung E.V., Munich (DE)

( * ) Notice: Subject to any disclaimer, the term of this patent is extended or adjusted under 35 U.S.C. 154(b) by 0 days.

(21) Appl. No.: 16/465,878

(22) PCT Filed: Dec. 1, 2017

(86) PCT No.: PCT/EP2017/081190
§ 371 (c)(1),
(2) Date: May 31, 2019

(87) PCT Pub. No.: WO2018/100159
PCT Pub. Date: Jun. 7, 2018

(65) Prior Publication Data
US 2019/0367511 A1 Dec. 5, 2019

(30) Foreign Application Priority Data
Dec. 2, 2016 (EP) .................................... 16201913

(51) Int. Cl.
*C07D 471/04* (2006.01)
*A61P 31/04* (2006.01)
*A61K 9/00* (2006.01)
*C07D 491/20* (2006.01)

(52) U.S. Cl.
CPC .......... *C07D 471/04* (2013.01); *A61K 9/0014* (2013.01); *A61P 31/04* (2018.01); *C07D 491/20* (2013.01)

(58) Field of Classification Search
CPC .................................................. C07D 471/04
See application file for complete search history.

(56) References Cited

U.S. PATENT DOCUMENTS

| 4,999,359 A * | 3/1991 | Vecchietti | A61P 25/04 514/301 |
| 8,124,616 B2 * | 2/2012 | Frechette | A61P 31/04 514/301 |

FOREIGN PATENT DOCUMENTS

| JP | 08325234 A | * 12/1996 |
| JP | 2011-505373 A | 2/2011 |
| WO | WO 00/63208 A1 | 10/2000 |
| WO | WO 2013/184202 A1 | 12/2003 |
| WO | WO 2009/073534 A2 | 6/2009 |
| WO | WO 2013/070657 A1 | 5/2013 |
| WO | WO 2014/152604 A1 | 9/2014 |

OTHER PUBLICATIONS

Popova "Microbiology of Periodontal Diseases. A Review" Biotechnology & Biotechnological Equipment, 2013 27:3, 3754-3759.*
Fraunhofer—OIST Workshop Program Apr. 8, 2015, makes reference to a talk at 14:15-15:00: Targeting Bacterial Glutaminyl Cyclases in Peridontitis-Rational Approaches for the Generation of Selective, Locally Acting Antibiotics; Fighting Against Systemic Diseases Dr. Mirko Buchholz.*
Joint Workshop flier Apr. 8-9, 2015.*
Raunhofer Institute for Cell Therapy and Immunology IZI Annual Reprot 2015, pp. 159-186.*
International Search Report and Written Opinion, dated Jan. 31, 2018, in connection with Application No. PCT/EP2017/081190.
[No Author Listed], Database Accession No. 1359599-75-9, Chemical Abstracts Service. Mar. 2, 2002. XP-002769325, 1 page.
[No Author Listed], Database Accession No. 1791319-43-1, Chemical Abstracts Service. Jun. 29, 2015. XP-002769324, 1 page.
[No Author Listed], Database Accession No. 1791319-49-7, Chemical Abstracts Service. Jun. 29, 2015. XP-002769323, 1 page.
[No Author Listed], Database Accession No. 1357753-89-9, Chemical Abstracts Service. Feb. 28, 2012. XP-002769322, 1 page.
[No Author Listed], Database Accession No. 1357979-51-1, Chemical Abstracts Service. Feb. 28, 2012. XP-002769321,1 page.
[No Author Listed], Database Accession No. 1791114-23-2, Chemical Abstracts Service. Jun. 29, 2015. XP-002769320, 1 page.
[No Author Listed], Database Accession No. 1359578-66-7, Chemical Abstracts Service. Mar. 2, 2012. XP-002769319, 1 page.
[No Author Listed], Database Accession No. 1790477-24-5, Chemical Abstracts Service. Jun. 28, 2015. XP-002769318, 1 page.
[No Author Listed], Database Accession No. 1790883-82-7, Chemical Abstracts Service. Jun. 29, 2015. XP-002769317, 1 page.

(Continued)

*Primary Examiner* — David K O'Dell
(74) *Attorney, Agent, or Firm* — Wolf, Greenfield & Sacks, P.C.

(57) ABSTRACT

The present invention relates to bacterial glutaminyl cyclases and inhibitors thereof for use in the treatment of periodontitis and related conditions, and provides a bacterial glutaminyl cyclase (bacQC); an antibody which recognizes the bacQC, a method for identifying an inhibitor of the bacQC; a compound according to Formula (I); a pharmaceutical composition comprising a bacQC inhibitor compound; a bacQC inhibitor compound and/or a pharmaceutical composition for use in a method for treatment of the human or animal body, for use in a method for therapy or prophylaxis of a bacterial infection, and for use in a method for therapy and/or prophylaxis of an acute, chronic or recurrent periodontal disease.

20 Claims, 7 Drawing Sheets
Specification includes a Sequence Listing.

(56) References Cited

OTHER PUBLICATIONS

[No Author Listed], Database Accession No. 1358167-90-4, Chemical Abstracts Service. Feb. 29, 2012. XP-002769316, 1 page.
[No Author Listed], Database Accession No. 1358191-18-0, Chemical Abstracts Service. Feb. 29, 2012. XP-002769315, 1 page.
[No Author Listed], Database Accession No. 1359598-40-5, Chemical Abstracts Service. Mar. 2, 2012. XP-002769314, 1 page.
[No Author Listed], Database Accession No. 1790653-72-3, Chemical Abstracts Service. Jun. 29, 2015. XP-002769313, 1 page.
[No Author Listed], Database Accession No. 1791318-99-4, Chemical Abstracts Service. Jun. 29, 2015. XP-002769312, 1 page.
[No Author Listed], Database Accession No. 1787475-02-8, Chemical Abstracts Service. Jun. 29, 2015. XP-002769311,1 page.
[No Author Listed], Database Accession No. G8UMP8 sequence. Database UniProt. Feb. 22, 2012. XP-002769310, 1 page.
[No Author Listed], Database Accession No. I1YWY9 sequence. Database UniProt. Jul. 11, 2012. XP-002769309, 1 page.
[No Author Listed], Database Accession No. W1R6V3 sequence. Database UniProt. Mar. 19, 2014. XP-002769308, 1 page.
[No Author Listed], Combatting periodontal pathogens, Fraunhofer Research News. Oct. 1, 2014. XP055361221, retrieved Apr. 3, 2017, https://wwww.fraunhofer.de/content/dam/zv/en/press-media/2014/october/Research-News/rn10_2014_OKTOBER.pdf, 14 pages.
[No Author Listed], Periodic Report Summary 1, Trigger. Apr. 17, 2015. XP055361226, retrieved Apr. 17, 2015, http://cordis.europa.edu/result/rcn/158856_en.pdf, 3 pages.
[No Author Listed] Methanone, CAS Registry No. 1358196-83-4. STN Easy Database. Jul. 10, 2020. 1 page.
Buchholz, Targeting bacterial Glutaminyl Cyclases in Peridontitis-rational approaches for the generation of selective, locally acting antibiotics; fighting against systemic diseases. Fraunhofer-Okinawa Institute of Science and Technology (OIST) Workshop, Apr. 8-10, 2015, Okinawa, Japan. 39 pages.
Buchholz, Targeting bacterial Glutaminyl Cyclases in Peridontitis-rational approaches for the generation of selective, locally acting antibiotics. Joint meeting in honour of Prof. Jan Potempa and annual TRIGGER conference, May 15-17, 2015, Krakow, Poland. 30 pages.
[No. Author Listed] CAS Registry No. 1309290-33-2. STN Database. Jun. 13, 2011. 1 page.
[No. Author Listed] CAS Registry No. 1340700-56-2. STN Database. Nov. 4, 2011. 1 page.
[No. Author Listed] CAS Registry No. 1340788-18-2. STN Database. Nov. 4, 2011. 1 page.
[No. Author Listed] CAS Registry No. 1340870-76-9. STN Database. Nov. 4, 2011. 1 page.
[No. Author Listed] CAS Registry No. 1340943-10-3. STN Database. Nov. 4, 2011. 1 page.
[No. Author Listed] CAS Registry No. 1340984-26-0. STN Database. Nov. 4, 2011. 1 page.
[No. Author Listed] CAS Registry No. 1351068-86-4. STN Database. Dec. 16, 2011. 1 page.
[No. Author Listed] CAS Registry No. 1358168-20-3. STN Database. Feb. 29, 2012. 1 page.
[No. Author Listed] CAS Registry No. 1358190-93-8. STN Database. Feb. 29, 2012. 1 page.
[No. Author Listed] CAS Registry No. 1358191-00-0. STN Database. Feb. 29, 2012. 1 page.
[No. Author Listed] CAS Registry No. 1359591-18-6. STN Database. Mar. 2, 2012. 1 page.
[No. Author Listed] CAS Registry No. 1359591-24-4. STN Database. Mar. 2, 2012. 1 page.
[No. Author Listed] CAS Registry No. 1359591-29-9. STN Database. Mar. 2, 2012. 1 page.
[No. Author Listed] CAS Registry No. 1359591-33-5. STN Database. Mar. 2, 2012. 1 page.
[No. Author Listed] CAS Registry No. 1359591-43-4. STN Database. Mar. 2, 2012. 1 page.
[No. Author Listed] CAS Registry No. 1452895-84-9. STN Database. Sep. 20, 2013. 1 page.
[No. Author Listed] CAS Registry No. 1609920-95-7. STN Database. Jun. 6, 2014. 1 page.
[No. Author Listed] CAS Registry No. 1790949-53-9. STN Database. Jun. 29, 2015. 1 page.
[No. Author Listed] CAS Registry No. 1791114-45-8. STN Database. Jun. 29, 2015. 1 page.
[No. Author Listed] CAS Registry No. 1791240-46-4. STN Database. Jun. 29, 2015. 1 page.
Yutilov et al., Synthesis of Ticlopidine Analogs Based on Spinaceamine and s-Azaspinaceamine. Pharmaceutical Chemistry. 2003;37(5):243-245. Translated from Russian.

\* cited by examiner (A)
```
PgQC    ----MKRLITTGAAFLLAATLSACNGNNTSETQGDRTEQAETVQADLFSADSAYTFVQRQ
hQC     MAGGRHRRVVGTLHLLLLVAALPWASRGVSPSASAWPEEKNYHQPAILNSSALRQIAEGT
            :* :.    :**  .:  .  ....*  :  .  .*: :  *. ::.:.:     :.:

PgQC    VN----------FGPRIPGTAPHRACGDWLVATLRSFGAAVQEQTAEIKAHDGTMLPMR
hQC     SISEMWQNDLQPLLIERYPGSPGSYAARQHIMQRIQRLQADWVLEIDTFLSQTPYGYRSF
            :    * **:.   *. : ::  ::  : *      :    :  :::

PgQC    -NIIASYRPEATGRMLLMAHWDTRPVCDQDANPAMHTETFDGADDGGSGVGVLLEIARYL
hQC     SNIISTLNPTAKRHLVLACHYDSKYFSHWNN------RVFVGATDSAVPCAMMLELARAL
         ***::  .* *.  :::* .*:*::  ... :       ..*  ** *..    .::**:** *

PgQC    GQQKD---------LGMGIDIVFFDTEDYGSYGDDESWCLGSQYWSR----NPHVAGYK-
hQC     DKKLLSLKTVSDSKPDLSLQLIFFDGEEAFLHWSPQDSLYGSRHLAAKMASTPHPPGARG
         .::       .:.:::::*** *:    :   . :.    **:: :        .** .* :

PgQC    ------AEAGILLDMVGAKGATFY--------WEYFSKSYAPGLISAVWQTAAALGYGNY
hQC     TSQLHGMDLLVLLDLIGAPNPTFPNFFPNSARWFERLQAIEHELHELGLLKDHSLEGRYF
              : :***::** ..**         *      ::      *    .   . :*    :

PgQC    FIQADGGALTDDHVPVIKNLGIPCIDIINYSSKNEHGFGDHWHTQRDNMQIIDKNVLDAV
hQC     QNYSYGGVIQDDHIPFLR-RGVPVLHLIPSP------FPEVWHTMDDNEENLDESTIDNL
          : **.: ***:*.::  *:* ..:*  .     * : ***  ** : :*:...:* :

PgQC    GETVIRYLDEQVKAASH
hQC     NKILQVFVLEYLHL---
         .: :  ::  * ::
```

(B)
```
PiQC    MGRQLAARYGTDTGCQTKIKRTTMNGKIKFLCSGMAVLLLAAFAFSCKGKSSNNSTEDGD
PgQC    ---------------------------MKRLITTGAAFLLAATLSACNGNNTS--ETQGD
TfQC    ---------------------------MDRMINKYAGVLLGSLILSCCGQKNTTKEETTE
                                   :. :  .   *  .**.:   :* *:...     :

PiQC    TVATAK-PVGPTFNPDSAFAYTAAQCDFGPRTMNSSAHDKCEQWIISKFKQYGCEVQTQK
PgQC    RTEQAETVQADLFSADSAYTFVQRQVNFGPRIPGTAPHRACGDWLVATLRSFGAAVQEQT
TfQC    PADTDKRIEAPTFNADSAYAYIERQVAFGPRVPNTEAHQRCADYLAGELDRHGAKVYVQE
          .      :   . *. *** :::    *  ****   :  *  * *  :::  .  :  .*. *   *

PiQC    ADLKAYDGTILKSTNIIARTNPNAQRRILLCAHWDSRPWADNDPDSTNHKKPVMAANDGA
PgQC    AEIKAHDGTMLPMRNIIASYRPEATGRMLLMAHWDTRPVCDQDANPAMHTETFDGADDGG
TfQC    AVLTAYNGEKLKAQNIVGAFQPEKSRRVLLFAHWDSRPYADHDTDEANHRKPIDGADDGG
        *  :..*::*   *    **:.   .*:   *:** *****:**  .*. *  :   *  . . .*:**.

PiQC    SGVGVMIELARQLQADSTLNVGVDFVCFDAEDWGVPQWETNYQEQSGDSWALGSNYFAKN
PgQC    SGVGVLLEIARYLGQQKDLGMGIDIVFFDTEDYGSYG-----D---DESWCLGSQYWSRN
TfQC    SGVGILLEIARQIQ-AKAPAIGIDIVFFDAEDYGTPEFVDEYK---PDTWCLGSQFWAKN
        ****:::*:** :        .  :*:*:* **:** .            ::*.***::::*

PiQC    LPL-TVRPEFGILLDMVGGEGAQFYKEGISLQYAPDIVDRVWEAAKSAGFEAYFPTTRGG
PgQC    PHVAGYKAEAGILLDMVGAKGATFYWEYFSKSYAPGLISAVWQTAAALGYGNYFIQADGG
TfQC    PHVPNYKAEFGILLDMVGSRGATFYKESTSVQYAARYVEKVWTAARELGYGKYFINAQGG
          :  : * ******** . ** **  .  . :**  :: ** : * * :  *: : **

PiQC    MVTDDHYPLNKIAAIPTIDIIPHYPDCAQSTFGPTWHTVNDTMEHIDRTTLQAVGQTLIQ
PgQC    ALTDDHVPVIKNLGIPCIDIINY-SSKNEHGFGDHWHTQRDNMQIIDKNVLDAVGETVIR
TfQC    AIVDDHQYVIQGLRTPCLDIINY-DPDTQSGFGPYWHTQNDTMENIDRETLKAVGETILN
        :.***   ::  :   * :*** :      *  **  *** ***.*:*: .*.:*****:::.

PiQC    VLYSM------
PgQC    YLDEQVKAASH
TfQC    VIYNH------
```

FIG. 1

SEQUENCE LISTING

```
<160> NUMBER OF SEQ ID NOS: 14

<210> SEQ ID NO 1
<211> LENGTH: 333
<212> TYPE: PRT
<213> ORGANISM: Porphyromonas gingivalis
<220> FEATURE:
<221> NAME/KEY: misc_feature
<223> OTHER INFORMATION: PgQC

<400> SEQUENCE: 1

Met Lys Arg Leu Ile Thr Thr Gly Ala Ala Phe Leu Leu Ala Ala Thr
1               5                   10                  15

Leu Ser Ala Cys Asn Gly Asn Asn Thr Ser Glu Thr Gln Gly Asp Arg
            20                  25                  30

Thr Glu Gln Ala Glu Thr Val Gln Ala Asp Leu Phe Ser Ala Asp Ser
        35                  40                  45

Ala Tyr Thr Phe Val Gln Arg Gln Val Asn Phe Gly Pro Arg Ile Pro
```

```
            50                  55                  60
Gly Thr Ala Pro His Arg Ala Cys Gly Asp Trp Leu Val Ala Thr Leu
 65                  70                  75                  80

Arg Ser Phe Gly Ala Ala Val Gln Glu Gln Thr Ala Glu Ile Lys Ala
                 85                  90                  95

His Asp Gly Thr Met Leu Pro Met Arg Asn Ile Ile Ala Ser Tyr Arg
            100                 105                 110

Pro Glu Ala Thr Gly Arg Met Leu Leu Met Ala His Trp Asp Thr Arg
            115                 120                 125

Pro Val Cys Asp Gln Asp Ala Asn Pro Ala Met His Thr Glu Thr Phe
        130                 135                 140

Asp Gly Ala Asp Asp Gly Ser Gly Val Gly Val Leu Leu Glu Ile
145                 150                 155                 160

Ala Arg Tyr Leu Gly Gln Gln Lys Asp Leu Gly Met Gly Ile Asp Ile
                165                 170                 175

Val Phe Phe Asp Thr Glu Asp Tyr Gly Ser Tyr Gly Asp Asp Glu Ser
            180                 185                 190

Trp Cys Leu Gly Ser Gln Tyr Trp Ser Arg Asn Pro His Val Ala Gly
        195                 200                 205

Tyr Lys Ala Glu Ala Gly Ile Leu Leu Asp Met Val Gly Ala Lys Gly
        210                 215                 220

Ala Thr Phe Tyr Trp Glu Tyr Phe Ser Lys Ser Tyr Ala Pro Gly Leu
225                 230                 235                 240

Ile Ser Ala Val Trp Gln Thr Ala Ala Ala Leu Gly Tyr Gly Asn Tyr
                245                 250                 255

Phe Ile Gln Ala Asp Gly Gly Ala Leu Thr Asp Asp His Val Pro Val
            260                 265                 270

Ile Lys Asn Leu Gly Ile Pro Cys Ile Asp Ile Asn Tyr Ser Ser
        275                 280                 285

Lys Asn Glu His Gly Phe Gly Asp His Trp His Thr Gln Arg Asp Asn
        290                 295                 300

Met Gln Ile Ile Asp Lys Asn Val Leu Asp Ala Val Gly Glu Thr Val
305                 310                 315                 320

Ile Arg Tyr Leu Asp Glu Gln Val Lys Ala Ala Ser His
                325                 330

<210> SEQ ID NO 2
<211> LENGTH: 363
<212> TYPE: PRT
<213> ORGANISM: Prevotella intermedia
<220> FEATURE:
<221> NAME/KEY: misc_feature
<223> OTHER INFORMATION: PiQC

<400> SEQUENCE: 2

Met Gly Arg Gln Leu Ala Ala Arg Tyr Gly Thr Asp Thr Gly Cys Gln
 1               5                  10                  15

Thr Lys Ile Lys Arg Thr Thr Met Asn Gly Lys Ile Lys Phe Leu Cys
                20                  25                  30

Ser Gly Met Ala Val Leu Leu Leu Ala Ala Phe Ala Phe Ser Cys Lys
            35                  40                  45

Gly Lys Ser Ser Asn Asn Ser Thr Glu Asp Gly Asp Thr Val Ala Thr
        50                  55                  60

Ala Lys Pro Val Gly Pro Thr Phe Asn Pro Asp Ser Ala Phe Ala Tyr
 65                  70                  75                  80
```

-continued

```
Thr Ala Ala Gln Cys Asp Phe Gly Pro Arg Thr Met Asn Ser Ser Ala
                85                  90                  95

His Asp Lys Cys Glu Gln Trp Ile Ile Ser Lys Phe Lys Gln Tyr Gly
            100                 105                 110

Cys Glu Val Gln Thr Gln Lys Ala Asp Leu Lys Ala Tyr Asp Gly Thr
        115                 120                 125

Ile Leu Lys Ser Thr Asn Ile Ile Ala Arg Thr Asn Pro Asn Ala Gln
    130                 135                 140

Arg Arg Ile Leu Leu Cys Ala His Trp Asp Ser Arg Pro Trp Ala Asp
145                 150                 155                 160

Asn Asp Pro Asp Ser Thr Asn His Lys Lys Pro Val Met Ala Ala Asn
                165                 170                 175

Asp Gly Ala Ser Gly Val Gly Val Met Ile Glu Leu Ala Arg Gln Leu
            180                 185                 190

Gln Ala Asp Ser Thr Leu Asn Val Gly Val Asp Phe Val Cys Phe Asp
        195                 200                 205

Ala Glu Asp Trp Gly Val Pro Gln Trp Glu Thr Asn Tyr Gln Glu Gln
    210                 215                 220

Ser Gly Asp Ser Trp Ala Leu Gly Ser Asn Tyr Phe Ala Lys Asn Leu
225                 230                 235                 240

Pro Leu Thr Val Arg Pro Glu Phe Gly Ile Leu Leu Asp Met Val Gly
                245                 250                 255

Gly Glu Gly Ala Gln Phe Tyr Lys Glu Gly Ile Ser Leu Gln Tyr Ala
            260                 265                 270

Pro Asp Ile Val Asp Arg Val Trp Glu Ala Ala Lys Ser Ala Gly Phe
        275                 280                 285

Glu Ala Tyr Phe Pro Thr Thr Arg Gly Gly Met Val Thr Asp Asp His
    290                 295                 300

Tyr Pro Leu Asn Lys Ile Ala Ala Ile Pro Thr Ile Asp Ile Ile Pro
305                 310                 315                 320

His Tyr Pro Asp Cys Ala Gln Ser Thr Phe Gly Pro Thr Trp His Thr
                325                 330                 335

Val Asn Asp Thr Met Glu His Ile Asp Arg Thr Thr Leu Gln Ala Val
            340                 345                 350

Gly Gln Thr Leu Ile Gln Val Leu Tyr Ser Met
        355                 360

<210> SEQ ID NO 3
<211> LENGTH: 333
<212> TYPE: PRT
<213> ORGANISM: Tannerella forsythia
<220> FEATURE:
<221> NAME/KEY: misc_feature
<223> OTHER INFORMATION: TfQC

<400> SEQUENCE: 3

Met Asp Arg Met Ile Asn Lys Tyr Ala Gly Val Leu Leu Gly Ser Leu
1               5                   10                  15

Ile Leu Ser Cys Cys Gly Gln Lys Asn Thr Thr Lys Glu Glu Thr Thr
            20                  25                  30

Glu Pro Ala Asp Thr Asp Lys Arg Ile Glu Ala Pro Thr Phe Asn Ala
        35                  40                  45

Asp Ser Ala Tyr Ala Tyr Ile Glu Arg Gln Val Ala Phe Gly Pro Arg
    50                  55                  60

Val Pro Asn Thr Glu Ala His Gln Arg Cys Ala Asp Tyr Leu Ala Gly
65                  70                  75                  80
```

Glu Leu Asp Arg His Gly Ala Lys Val Tyr Val Gln Glu Ala Val Leu
                    85                  90                  95

Thr Ala Tyr Asn Gly Glu Lys Leu Lys Ala Gln Asn Ile Val Gly Ala
                100                 105                 110

Phe Gln Pro Glu Lys Ser Arg Arg Val Leu Leu Phe Ala His Trp Asp
                115                 120                 125

Ser Arg Pro Tyr Ala Asp His Asp Thr Asp Glu Ala Asn His Arg Lys
            130                 135                 140

Pro Ile Asp Gly Ala Asp Asp Gly Gly Ser Gly Val Gly Ile Leu Leu
145                 150                 155                 160

Glu Ile Ala Arg Gln Ile Gln Ala Lys Ala Pro Ala Ile Gly Ile Asp
                165                 170                 175

Ile Val Phe Phe Asp Ala Glu Asp Tyr Gly Thr Pro Glu Phe Val Asp
            180                 185                 190

Glu Tyr Lys Pro Asp Thr Trp Cys Leu Gly Ser Gln Phe Trp Ala Lys
            195                 200                 205

Asn Pro His Val Pro Asn Tyr Lys Ala Glu Phe Gly Ile Leu Leu Asp
            210                 215                 220

Met Val Gly Ser Arg Gly Ala Thr Phe Tyr Lys Glu Ser Thr Ser Val
225                 230                 235                 240

Gln Tyr Ala Ala Arg Tyr Val Glu Lys Val Trp Thr Ala Ala Arg Glu
                245                 250                 255

Leu Gly Tyr Gly Lys Tyr Phe Ile Asn Ala Gln Gly Gly Ala Ile Val
            260                 265                 270

Asp Asp His Gln Tyr Val Ile Gln Gly Leu Arg Thr Pro Cys Leu Asp
            275                 280                 285

Ile Ile Asn Tyr Asp Pro Asp Thr Gln Ser Gly Phe Gly Pro Tyr Trp
            290                 295                 300

His Thr Gln Asn Asp Thr Met Glu Asn Ile Asp Arg Glu Thr Leu Lys
305                 310                 315                 320

Ala Val Gly Glu Thr Ile Leu Asn Val Ile Tyr Asn His
                325                 330

<210> SEQ ID NO 4
<211> LENGTH: 361
<212> TYPE: PRT
<213> ORGANISM: Homo sapiens
<220> FEATURE:
<221> NAME/KEY: misc_feature
<223> OTHER INFORMATION: hQC

<400> SEQUENCE: 4

Met Ala Gly Gly Arg His Arg Arg Val Val Gly Thr Leu His Leu Leu
1               5                   10                  15

Leu Leu Val Ala Ala Leu Pro Trp Ala Ser Arg Gly Val Ser Pro Ser
                20                  25                  30

Ala Ser Ala Trp Pro Glu Glu Lys Asn Tyr His Gln Pro Ala Ile Leu
            35                  40                  45

Asn Ser Ser Ala Leu Arg Gln Ile Ala Glu Gly Thr Ser Ile Ser Glu
        50                  55                  60

Met Trp Gln Asn Asp Leu Gln Pro Leu Leu Ile Glu Arg Tyr Pro Gly
65                  70                  75                  80

Ser Pro Gly Ser Tyr Ala Ala Arg Gln His Ile Met Gln Arg Ile Gln
                85                  90                  95

Arg Leu Gln Ala Asp Trp Val Leu Glu Ile Asp Thr Phe Leu Ser Gln

```
                100             105             110
Thr Pro Tyr Gly Tyr Arg Ser Phe Ser Asn Ile Ile Ser Thr Leu Asn
            115                 120             125
Pro Thr Ala Lys Arg His Leu Val Leu Ala Cys His Tyr Asp Ser Lys
        130                 135             140
Tyr Phe Ser His Trp Asn Asn Arg Val Phe Val Gly Ala Thr Asp Ser
145                 150                 155                 160
Ala Val Pro Cys Ala Met Met Leu Glu Leu Ala Arg Ala Leu Asp Lys
                165                 170                 175
Lys Leu Leu Ser Leu Lys Thr Val Ser Asp Ser Lys Pro Asp Leu Ser
            180                 185                 190
Leu Gln Leu Ile Phe Phe Asp Gly Glu Glu Ala Phe Leu His Trp Ser
        195                 200                 205
Pro Gln Asp Ser Leu Tyr Gly Ser Arg His Leu Ala Ala Lys Met Ala
    210                 215                 220
Ser Thr Pro His Pro Pro Gly Ala Arg Gly Thr Ser Gln Leu His Gly
225                 230                 235                 240
Met Asp Leu Leu Val Leu Leu Asp Leu Ile Gly Ala Pro Asn Pro Thr
                245                 250                 255
Phe Pro Asn Phe Phe Pro Asn Ser Ala Arg Trp Phe Glu Arg Leu Gln
            260                 265                 270
Ala Ile Glu His Glu Leu His Glu Leu Gly Leu Leu Lys Asp His Ser
        275                 280                 285
Leu Glu Gly Arg Tyr Phe Gln Asn Tyr Ser Tyr Gly Gly Val Ile Gln
    290                 295                 300
Asp Asp His Ile Pro Phe Leu Arg Arg Gly Val Pro Val Leu His Leu
305                 310                 315                 320
Ile Pro Ser Pro Phe Pro Glu Val Trp His Thr Met Asp Asp Asn Glu
                325                 330                 335
Glu Asn Leu Asp Glu Ser Thr Ile Asp Asn Leu Asn Lys Ile Leu Gln
            340                 345                 350
Val Phe Val Leu Glu Tyr Leu His Leu
        355                 360

<210> SEQ ID NO 5
<211> LENGTH: 30
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: pgQC NdeI forward

<400> SEQUENCE: 5
aaacatatga acggcaataa cacaagtgaa                                    30

<210> SEQ ID NO 6
<211> LENGTH: 27
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: pgQC NheI reverse

<400> SEQUENCE: 6
tttgctagct cagtgtgaag cggcttt                                       27
```

<210> SEQ ID NO 7
<211> LENGTH: 27
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: piQC NdeI forward

<400> SEQUENCE: 7
tttcatatga aggaaaatc gtctaac                                 27

<210> SEQ ID NO 8
<211> LENGTH: 26
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: piQC NheI reverse

<400> SEQUENCE: 8
atgctagctt acatgctgta aagcac                                 26

<210> SEQ ID NO 9
<211> LENGTH: 27
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: tfQC NdeI forward

<400> SEQUENCE: 9
tcacatatgg gtcagaaaaa tacgaca                                27

<210> SEQ ID NO 10
<211> LENGTH: 29
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: tfQC NheI reverse

<400> SEQUENCE: 10
atgctagctt atttctcatt ataaatcac                              29

<210> SEQ ID NO 11
<211> LENGTH: 90
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: seq pgQC NdeI forward

<400> SEQUENCE: 11
aaacatatga aaagactgat aacaacagga gcagcctttc tactggctgc tacactctct   60
gcctgcaacg gcaataacac aagtgaaacg                                    90

```
<210> SEQ ID NO 12
<211> LENGTH: 27
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: seq pgQC XhoI reverse

<400> SEQUENCE: 12
tttctcgagg tgtgaagcgg ctttcac                                            27

<210> SEQ ID NO 13
<211> LENGTH: 21
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: seq pgQC RBS NotI forward

<400> SEQUENCE: 13
tggcggccgc taagaaggag a                                                  21

<210> SEQ ID NO 14
<211> LENGTH: 27
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<223> OTHER INFORMATION: seq pgQC XbaI reverse

<400> SEQUENCE: 14
ttttctagag tgtgaagcgg ctttcac                                            27
```

BACTERIAL GLUTAMINYL CYCLASES AND INHIBITORS THEREOF FOR USE IN THE TREATMENT OF PERIODONTITIS

CROSS REFERENCE TO RELATED APPLICATION(S)

This Application is a National Stage filing under 35 U.S.C. 371 of International Patent Application No. PCT/EP2017/081190, filed Dec. 1, 2017, which claims priority to European Application Number 16201913.7, filed Dec. 2, 2016. The entire contents of these applications are incorporated herein by reference in their entirety.

FIELD OF THE INVENTION

The present invention relates to bacterial glutaminyl cyclases and inhibitors thereof for use in the treatment of periodontitis and related conditions.

BACKGROUND ART

Periodontal diseases are highly prevalent with about 30% of the human population being affected worldwide, have considerable impact on individuals and society, and are costly to treat. The cost of dental care is the fourth highest of all diseases and consuming between 5 and 10% of all healthcare resources (Batchelor, P. *British Dental Journal* 2014, 217, 405-409). Representative population studies show that periodontal diseases are widespread and their prevalence has been increasing since 1997 (Micheelis, W. et al. *Vierte Deutsche Mundgesundheitsstudie* (DMS IV), Deutscher Ärzte-Verlag, Köln, 2006). Amongst the adult population in Germany, 52.7% were found to be affected by moderately severe and 20.5% by severe forms of periodontitis. The health insurance expenditure in Germany for the direct treatment of periodontitis amounted to about EUR 1.1 billion (*Statistisches Bundesamt*, 2008), not including the costs incurred by secondary diseases.

Periodontitis is a general term describing inflammation condition of the periodontal apparatus which is caused by multi-bacterial induction and has strong relations to various systemic diseases, such as cardiovascular diseases, rheumatoid arthritis, chronic obstructive pulmonary disease and Alzheimer's disease.

The currently established therapy of periodontitis, according to the recommendations of the German Society Of Dental, Oral And Craniomandibular Sciences, is generally performed by manual supra and subgingival debridement (removal of the bacterial plaques) along with the application of antiseptic substances (daily disinfection by mouth washes), which disintegrates the entire oral biofilm and provides an opportunity for recolonization by potential pathogens. Furthermore, adjuvant systemic broad-spectrum antibiotic therapy is applied in advanced disease forms. The latter also leads to a non-selective destruction of the biofilm and has to be administered in high doses and over a prolonged period of time in order to reach sufficient therapeutic levels at the particular site of action, i.e. the gingival pocket. Standard adjuvant therapy of periodontitis involves, for instance, systemic administration of doxyciclin (per os) 1×200 mg/die for 1 day and 2×100 mg/die for further 18 days (Wissenschaftliche Stellungnahme: Adjuvante Antibiotika in der Parodontitistherapie, Deutsche Gesellschaft für Zahn-Mund-und Kieferheilkunde, D Z Z 2003). As a result, resistance development in oral pathogens is observed. Further, the microbiome in the patient's intestine is destroyed, which leads to a loss of metabolic support, immune modulation, and enables recolonization by potential pathogens.

The presence of periodontopathogenic bacteria varies among periodontitis patients. Nevertheless, the occurrence of certain bacterial species in the subgingival plaques has been found to be closely associated with the etiology of periodontal diseases (Socransky et al., *Journal of Clinical Periodontology*, 1998, 25, 134-144).

Thus, there is a high demand for the development of a new treatment for periodontitis and related conditions which is capable of targeting pathogens which induce a periodontal disease, while preferably substantially preserving the rest of the naturally occurring biofilm. Such treatment would provide significant improvement to patients and healthcare systems.

Problems to be Solved by the Invention

In view of the above, the present invention aims at the object of identification, purification and isolation of a novel therapeutic target protein which can be used for identifying inhibitors capable of targeting pathogens which induce a periodontal disease.

A further object of the present invention is to provide an antibody which recognizes said therapeutic target protein.

A further object of the present invention is to provide a method for identifying an inhibitor of said therapeutic target protein.

A further object of the present invention is to provide an inhibitor of said therapeutic target protein, and a pharmaceutical composition comprising such inhibitor. Said inhibitor should be preferably a selective inhibitor, i.e. selectively killing or selectively inhibiting the growth of (a) target bacterial pathogen(s) while being substantially inactive towards other bacterial and/or human protein targets.

A further object of the present invention is to provide a method for treatment of the human or animal body, and/or a compound or a pharmaceutical composition for use in such method.

A further object of the present invention is to provide a method for therapy or prophylaxis of a bacterial infection, and/or a compound or a pharmaceutical composition for use in such method, preferably by selectively killing or selectively inhibiting the growth of the pathogenic bacterial species.

A further object of the present invention is to provide a method for therapy or prophylaxis of an acute, chronic or recurrent periodontal disease and/or a compound or a pharmaceutical composition compound for use in in such method.

In the methods for treatment according to the above objects, the route of administration should be preferably topical administration or systemic administration, and the methods are preferably non-surgical methods.

SUMMARY OF THE INVENTION

As a solution to the above-formulated problems, the present invention provides a bacterial glutaminyl cyclase (bacQC), wherein the bacQC is a polypeptide comprising an amino acid sequence selected from the group consisting of SEQ ID NO: 1, SEQ ID NO: 2, SEQ ID NO: 3, and an amino acid sequence having a sequence identity of 80% or more to any one of SEQ ID NO: 1, SEQ ID NO: 2 and SEQ ID NO: 3.

The present invention further provides an antibody which recognizes the bacQC as defined above.

The present invention further provides a method for identifying an inhibitor of the bacQC as defined above, the method comprising:
(a) providing a composition comprising a substrate of the bacQC and the bacQC;
(b) providing a candidate compound;
(c) contacting the candidate compound with the composition;
(d) monitoring the catalytic activity of the bacQC;
(e) classifying the candidate compound as an inhibitor of the bacQC based on the effect of the candidate compound on the catalytic activity of bacQC, wherein a candidate compound that reduces the catalytic activity of the bacQC is classified a bacQC inhibitor.

The present invention further provides a compound according to the following Formula I,

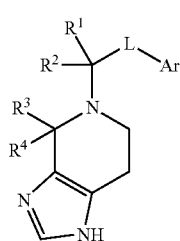

Formula I its individual enantiomers, its individual diastereoisomers, its hydrates, its solvates, its crystal forms, its individual tautomers or a pharmaceutically acceptable salt thereof,
wherein Ar, L, $R^1$, $R^2$, $R^3$, and $R^4$ are defined according to the appended claims.

The present invention further provides a pharmaceutical composition comprising the compound as defined above and a pharmaceutically acceptable excipient.

The present invention further provides a bacQC inhibitor, i.e. a compound identified by the above method for identifying an inhibitor of the bacQC and/or a compound according to the above Formula I, and/or a pharmaceutical composition as defined above for use in a method for treatment of the human or animal body; for use in a method for therapy and/or prophylaxis of a bacterial infection; and for use in a method for therapy and/or prophylaxis of an acute, chronic or recurrent periodontal disease.

BRIEF DESCRIPTION OF THE DRAWINGS

FIG. 1 shows an amino acid sequence alignment of human QC (hQC, SEQ ID NO: 4) and putative bacterial QC from *P. gingivalis* (PgQC, SEQ ID NO: 1) (A), and an amino acid sequence alignment of further putative QC *P. intermedia* (PiQC, SEQ ID NO: 2) and *T. forsythia* (TfQC, SEQ ID NO: 3)) and *P. gingivalis* (PgQC, SEQ ID NO: 1) (B).

DETAILED DESCRIPTION OF THE INVENTION

Figure 2:
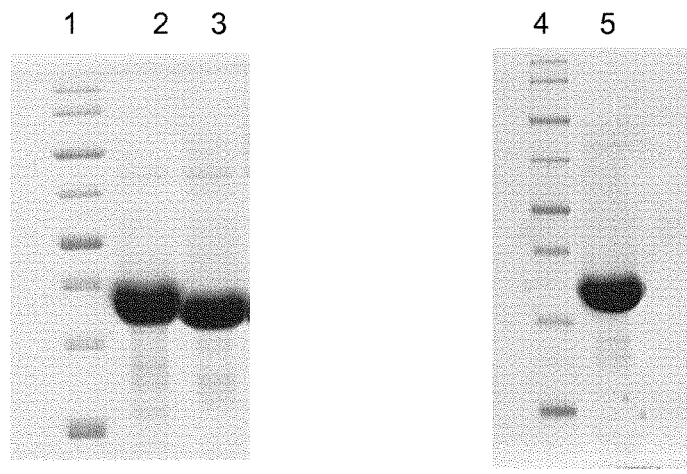
FIG. 2 shows SDS-PAGE of purified recombinant putative bacterial QCs expressed in *E. coli* Rosetta(DE3)pLysS.

Socransky et al. (*Journal of Clinical Periodontology*, 1998, 25 134-144) described that the occurrence in subgingival plaques of a so-called "red complex" consisting of the tightly related group *Tannerella forsythia*, *Porphyromonas gingivalis* and *Treponema denticola* relates strongly to clinical measures of periodontal disease, and in particular to pocket depth and bleeding on probing.

A further related complex (so-called "orange complex") includes members of the *Fusobacterium nucleatum/periodonticum* subspecies, *Prevotella intermedia*, *Prevotella nigrescens* and *Peptostreptococcus* micros. Colonization of healthy periodontal sites by members of the "orange complex" was found to correlate with the occurrence of gingivitis. The bacteria of the "orange complex" furthermore promote the colonization by bacteria of the "red complex", which in turn are associated with deep pockets and chronic periodontitis.

Bacteria of the "red complex" and the "orange complex" secrete a variety of virulence factors. For instance, it was found that *P. gingivalis* secretes cysteine proteases such as gingipain, *P. intermedia* secretes salivary IgA proteases, and *T. forsythia* secretes glycosidases.

The present inventors found surprisingly that about 80% of the secreted proteins bearing a signal peptide in the secretome of the oral pathogens *P. gingivalis*, *T. forsythia*, and *P. intermedia* are cleaved at a Xaa-Gln peptide bond by a signal peptidase. The N-termini of the released proteins contain a pGlu-residue.

This implies the existence of glutaminyl cyclases which seem to be essential for growth protein translocation across outer membrane and the growth of said periodontal pathogens.

Glutaminyl cyclases (QCs) (EC 2.3.2.5) are acyltransferases that catalyze the cyclization of N-terminal glutaminyl residues of proteins to pyroglutamate (pGlu) under release of $NH_3$, thus modifying the N-terminus of the peptides:

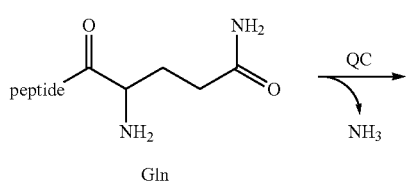

Gln

-continued

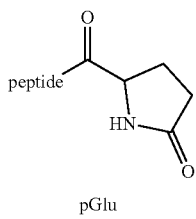
pGlu

Two types of QCs (Type I and Type II) have been defined so far. Type I QCs were found in plants and in several pathogenic bacteria and human parasites (Huang et al., *J. Mol. Biol.* 2010, 401, 374-388). Papaya QC (pQC) is the best-known Type I QC. This enzyme was first discovered in the latex of the tropical plant *Carica papaya* (Messer, M. *Nature* 1963, 197, 1299). The enzyme exhibits catalytic activity over a broad pH range (pH 3.5-11). X-ray crystallographic analyses revealed that pQC is a hatbox-shaped molecule, consisting of a five-bladed β-propeller traversed by a central channel (Wintjens, R., Belrhali, H., Clantin, B., Azarkan, M., Bompard, C., Baeyens-Volant, D., Looze, Y., and Villeret, V. *J. Mol. Biol.* 2006, 357, 457-470). pQC contains a zinc ion but is not inhibited at all by heterocyclic chelators (Zerhouni et al. *Biochim. Biophys. Acta* 1998, 1387, 275-290), and it is therefore assumed that the zinc has only a structural and stabilizing function. pQC is highly resistant to proteolytic, chemical, and thermal denaturations (Wintjens et al., Zerhouni et al.)

Type II QCs were mainly identified in the neuroendocrine tissues of mammals. Among Type II QCs, the human QC (hQC) is the most extensively studied one, which is known to be important in the maturation of numerous neuropeptides and cytokines in their secretory pathways. In contrast to Type I QCs, hQC is quite susceptible to chemical and thermal denaturation. Schilling et al., 2003 (*J. Biol. Chem.* 2003, 278, 49773-49779) have shown that hQC was significantly unstable above pH 8.5 and below pH 6.0. hQC adopts an α/β topology (Huang et al. *Proc. Nat/Acad. Sci. USA*, 2005, 102, 13117-13122) and was identified as a metalloenzyme, as suggested by the time-dependent inhibition by the heterocyclic chelators. Inactivated enzyme can be fully restored by the addition of $Zn^{2+}$ in the presence of equimolar concentrations of EDTA (Schilling et al., 2003). Thus, Type II QCs are metal-dependent transferases, suggesting that the active site bound metal ($Zn^{2+}$) is essential for the catalytic activity, in contrast to the Type I QCs, wherein zinc has only a structural and stabilizing function.

In summary, Type I QCs are generally found in plants, several bacteria and protozoa; they exhibit β-propeller structures; high resistance against proteolysis, heat, and acid; the optimal catalytic activity is at pH 3.5-11; and possess a structural $Ca^{2+}/Zn^{2+}$ ion.

In contrast, Type II QCs are mainly found in vertebrates; they exhibit α/β-topologies; low resistance against proteolysis, heat, and acid; the optimal catalytic activity is at pH 6.0-8.0; and there is catalytically essential $Zn^{2+}$ ion. Thus, Type II glutaminyl cyclases are zinc-dependent acyltransferases.

The present inventors surprisingly found that Type II QCs (in the following: "bacQC") are expressed in the oral pathogens *P. gingivalis, T. forsythia*, and *P. intermedia*.

The primary structure of the QC protein from *P. gingivalis* (PgQC, SEQ ID NO: 1) has a 25% identity to human QC (hQC, SEQ ID NO: 4). Furthermore, QC from *P. intermedia* (PiQC, SEQ ID NO: 2) and *T. forsythia* (TfQC, SEQ ID NO: 3) were identified, which share an identity to PgQC of 42% and 49%, respectively. Further experimental evidence shows that these enzymes indeed belong to the Type II QC family, as confirmed inter alia by pH and ionic strength dependency of the bacQC activity (Example 4), the inhibition of the QC activity by metal chelators (Example 5), the folding patterns of all three proteins suggesting an α/β topology as indicated by the CD spectroscopic analysis (Example 6), and their thermal stability (Example 7).

The present inventors found that bacQCs are expressed in and are essential for the growth of 2 out of 3 periodontitis-causing bacterial species of the "red complex", as well as at least one bacterial species of the "orange complex", and are therefore of crucial importance for as a target for the development of a therapeutic inhibitor with antibiotic properties for the treatment of periodontitis diseases and conditions.

Therapeutic Target Proteins (bacQC)

The present invention provides a bacterial glutaminyl cyclase (bacQC), wherein the bacQC is a polypeptide comprising an amino acid sequence selected from the group consisting of SEQ ID NO: 1, SEQ ID NO: 2, SEQ ID NO: 3, and an amino acid sequence having a sequence identity of 80% or more to any one of SEQ ID NO: 1, SEQ ID NO: 2 and SEQ ID NO: 3. bacQCs according to the present inventions can be identified, isolated and purified as described in Example 1, and can be used to identify inhibitors capable of selective targeting of periodontitis-inducing pathogens as further described in Examples 2 and 3.

For the purposes of comparing two or more amino acid sequences, the degree of identity between two amino acid sequences (percentage of "sequence identity") can be determined by conventional methods, for example, by means of standard sequence alignment algorithms known in the state of the art, such as, for example BLAST (Altschul S. F. et al. *J Mol Biol.* 1990, 215(3), 403-10).

Antibodies

The present invention further provides an antibody which recognizes a bacterial Type II glutaminyl cyclase (bacQC). The bacQC recognized by the antibody according to the present invention is preferably a polypeptide comprising an amino acid sequence selected from the group consisting of SEQ ID NO: 1, SEQ ID NO: 2, SEQ ID NO: 3, and an amino acid sequence having a sequence identity of 80% or more to any one of SEQ ID NO: 1, SEQ ID NO: 2 and SEQ ID NO: 3.

In one embodiment, the antibody is a polyclonal antibody. In another embodiment, the antibody is a monoclonal antibody.

In one further embodiment, the antibody exhibits high affinity and specificity for PgQC (SEQ ID NO: 1) as compared to any one of PiQC (SEQ ID NO: 2), TfQC (SEQ ID NO: 3) and/or hQC (SEQ ID NO: 4). In another embodiment, the antibody exhibits high affinity and specificity for PgQC (SEQ ID NO: 1) as compared to any one of PiQC (SEQ ID NO: 2), TfQC (SEQ ID NO: 3), and/or hQC (SEQ ID NO: 4).

In another embodiment, the antibody exhibits high affinity and specificity for PiQC (SEQ ID NO: 2) as compared to any one of PgQC (SEQ ID NO: 1), TfQC (SEQ ID NO: 3), and/or hQC (SEQ ID NO: 4).

In another embodiment, the antibody exhibits high affinity and specificity for TfQC (SEQ ID NO: 3) as compared to any one of PgQC (SEQ ID NO: 1), PiQC (SEQ ID NO: 2), and/or hQC (SEQ ID NO: 4).

In yet another embodiment, the antibody is preferably a chimeric, humanized or human antibody.

Method for Identifying an Inhibitor

The present invention further provides a method for identifying an inhibitor of the bacQC comprising the following steps a)-e):

a) providing a composition comprising a substrate of the bacQC and the bacQC;

b) providing a candidate compound;

c) contacting the candidate compound with the composition;

d) monitoring the catalytic activity of the bacQC;

e) classifying the candidate compound as an inhibitor of the bacQC based on the effect of the candidate compound on the catalytic activity of bacQC, wherein a candidate compound that reduces the catalytic activity of the bacQC is classified a bacQC inhibitor.

According to an embodiment of the invention, said composition is an aqueous solution, preferably comprising suitable buffer and/or salt components. Said substrate is preferably a peptide or peptide derivative comprising a glutamine residue at its N-terminus. Said substrate is preferably labeled, more preferably isotopically labeled, most preferably a fluorogenic substrate. The fluorogenic substrate preferably undergoes a change in fluorescence intensity after being converted in the course of a reaction catalyzed by a bacQC.

A suitable fluorogenic substrate for monitoring bacQC activity is H-Gln-AMC, as described in Schilling, S., Hoffmann, T., Wermann, M., Heiser, U., Wasternack, C., and Demuth, H.-U. *Anal. Biochem.* 2002, 303, 49-56 (Schilling et al., 2002):

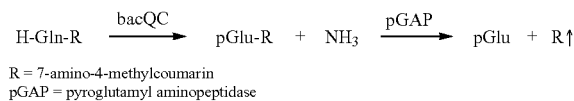

R = 7-amino-4-methylcoumarin
pGAP = pyroglutamyl aminopeptidase

The candidate compound can be contacted prior to, simultaneously with or after the addition of the remaining components of the composition of step a). The candidate compound is preferably provided in solution, more preferably as a DMSO solution.

The conversion of the substrate is monitored over time, e.g., by monitoring the emission of the fluorophore generated by the cleavage of a fluorogenic substrate. bacQC activity can be determined from a standard curve of the AMC under assay conditions.

The bacQC catalytic activity can be determined using different concentration of substrate, bacQC and/or candidate compound. Suitable measures for the bacQC catalytic activity are, e.g., inhibitory constants ($K_i$), 50% residual activity (RA) in the presence of a given concentration of a candidate compound, and/or $IC_{50}$ values.

bacQC Inhibitors

The present invention further provides a bacQC inhibitor, which is a compound identified by the method for identifying an inhibitor of the bacQC according to the present invention and/or a compound according to any one of the following aspects <1>-<20>.

<1> A compound according to the following Formula I,

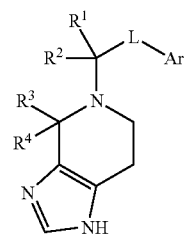

Formula I its individual enantiomers, its individual diastereoisomers, its hydrates, its solvates, its crystal forms, its individual tautomers or a pharmaceutically acceptable salt thereof, wherein Ar is selected from the group consisting of optionally substituted aryl and optionally substituted heteroaryl;

wherein L is selected from the group consisting of single bond, —$CR^5(R^6)$—, —$CR^5(R^6)$—$CR^7(R^8)$—, and —$C(R^5)$=$C(R^6)$—;

wherein $R^1$, $R^2$, $R^3$, $R^4$, $R^5$, $R^6$, $R^7$, and $R^8$ are the same or different from each other and are independently selected from the group consisting of H, F, Cl, Br, I, OH, optionally substituted alkyl, optionally substituted aryl, optionally substituted heteroalkyl, and optionally substituted heteroaryl;

wherein in each pair of groups $R^1/R^2$, $R^3/R^4$, $R^5/R^6$ and $R^7/R^8$, the two groups can be optionally joined together to form a carbocyclic or a heterocyclic ring, or can optionally represent =O.

<2> The compound according to aspect <1>, wherein $R^1$, $R^2$, $R^3$, and $R^4$ are the same or different from each other and are independently selected from H, OH, optionally substituted $C_{1-6}$ alkyl, and optionally substituted $C_{1-6}$ heteroalkyl.

<3> The compound according to aspect <1> or <2>, wherein each of $R^1$ and $R^2$ is H.

<4> The compound according to any one of aspects <1> to <3>, wherein $R^1$ and $R^2$ together represent =O.

<5> The compound according to any one of aspects <1> to <4>, wherein $R^3$ and $R^4$ are independently selected from group consisting of H, optionally substituted $C_{1-6}$ alkyl, and optionally substituted $C_{1-6}$ heteroalkyl.

<6> The compound according to aspect <5>, wherein $R^3$ is methyl.

<7> The compound according to aspect <5> or <6>, wherein $R^4$ is selected from the group consisting of H and methyl.

<8> The compound according to aspect <7>, wherein each of $R^3$ and $R^4$ is methyl.

<9> The compound according to any one of aspects <1> to <7>, wherein each of $R^3$ and $R^4$ is H.

<10> The compound according to aspect <1>, wherein $R^1$ and $R^2$ are joined together to form a carbocyclic or a heterocyclic ring.

<11> The compound according to any one of aspects <1> to <5>, wherein $R^3$ and $R^4$ are joined together to form a carbocyclic or a heterocyclic ring.

<12> The compound according to aspect <10> or <11>, wherein $R^1$ and $R^2$ or $R^3$ and $R^4$ are joined together to form a heterocyclic group represented by the following Formula II:

Formula II

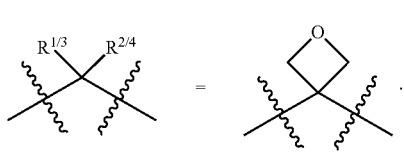

<13> The compound according to any one of aspects <1> to <12>, wherein L is a single bond.

<14> The compound according to any one of aspects <1> to <12>, wherein L is selected from the group consisting of —$CR^5(R^6)$—, —$C(R^5)=C(R^6)$— and —$CR^5(R^6)$—$CR^7(R^8)$—.

<15> The compound according to aspect <14>, wherein $R^5$, $R^6$, $R^7$ and $R^8$ are the same or different from each other and are independently selected from group consisting of H, OH, optionally substituted $C_{1-6}$ alkyl, and optionally substituted $C_{1-6}$ heteroalkyl.

<16> The compound according to aspect <15>, wherein each of $R^5$, $R^6$, $R^7$ and $R^8$ is H.

<17> The compound according to any of aspects <1> to <16>, wherein Ar is selected from the group consisting of aryl, alkoxyaryl, carboxyaryl, cyanoaryl, haloaryl, hydroxyaryl, alkoxyheteroaryl, cyanoheteroaryl, haloheteroaryl, heteroarylaryl, hydroxyheteroaryl and carboxyheteroaryl, each of which can be optionally substituted.

<18> The compound according to any one of aspects <1> to <17>, wherein Ar is selected from the group consisting of: 1,3-benzodioxol-5-yl, 2,3-dichlorophenyl, 2,3-dihydro-1,4-benzodioxin-6-yl, 3-chloro-5-methoxyphenyl, 3-chlorophenyl, 3-fluorophenyl, 3-methoxyphenyl, 3,4,5-trifluorophenyl, 3,5-dichlorophenyl, 4-(benzyloxy)phenyl, 4-[2-(morpholin-4-yl)ethoxy]phen-1-yl, 4-butoxyphenyl, 4-chlorophenyl, 4-fluoro-3-methoxyphenyl, 4-fluorophenyl, 4-methoxyphenyl, biphenyl-3-yl, naphthalen-2-yl, and phenyl.

<19> The compound according to any one of aspects <1> to <17>, wherein said substituted aryl is represented by one of the following structures Ar-I to Ar-VI, Ar-I

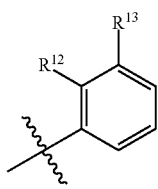

Ar-II

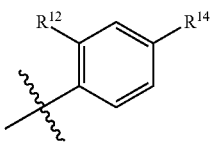

Ar-III

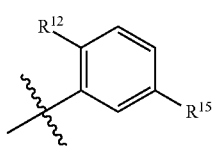

Ar-IV

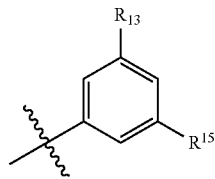

Ar-V

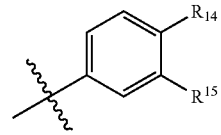

Ar-VI

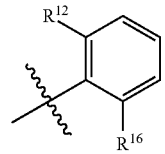

wherein:

$R^{12}$ is independently selected from the group consisting of H, F, Cl, Br, I, OH, CN, optionally substituted alkyl, optionally substituted alkoxy, optionally substituted aryl, optionally substituted heteroalkyl, and optionally substituted heteroaryl;

$R^{13}$ is independently selected from the group consisting of H, Cl, Br, I, OH, CN, optionally substituted alkyl, optionally substituted alkoxy, optionally substituted aryl, optionally substituted heteroalkyl, and optionally substituted heteroaryl;

$R^{14}$ is independently selected from the group consisting of H, F, Cl, Br, I, OH, CN, optionally substituted alkyl, optionally substituted alkoxy, optionally substituted aryl, optionally substituted heteroalkyl, and optionally substituted heteroaryl;

$R^{15}$ is independently selected from the group consisting of H, Cl, Br, I, OH, CN, optionally substituted alkyl, optionally substituted alkoxy, optionally substituted aryl, optionally substituted heteroalkyl, and optionally substituted heteroaryl;

$R^{16}$ is independently selected from the group consisting of H, F, Cl, Br, I, OH, CN, optionally substituted alkyl, optionally substituted alkoxy, optionally substituted aryl, optionally substituted heteroalkyl, and optionally substituted heteroaryl;

wherein any two groups of $R^{12}$ to $R^{16}$ can optionally be joined together to form a carbocyclic or a heterocyclic ring; and wherein at least one of $R^{12}$ to $R^{16}$ is not H.

<20> The compound according to any one of aspects <1> to <17>, wherein said substituted aryl is represented by one of the following structures Ar-VII to Ar-XIV, Ar-VII

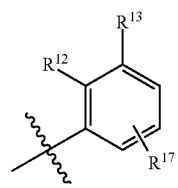

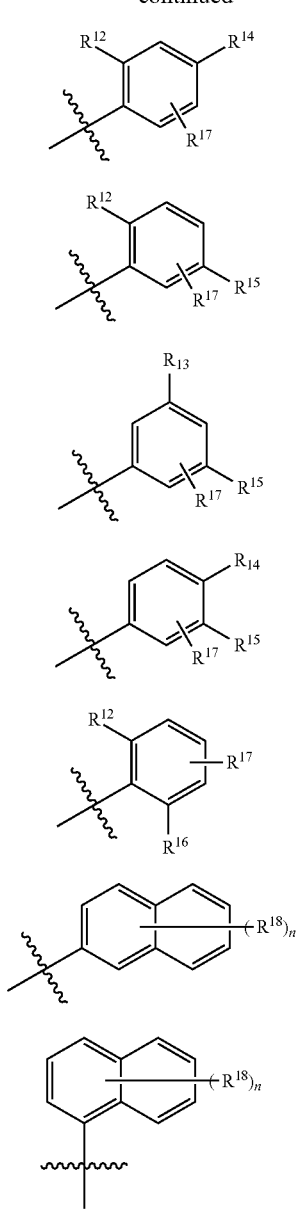

wherein:

R¹² is independently selected from the group consisting of F, Cl, Br, I, OH, CN, optionally substituted alkyl, optionally substituted alkoxy, optionally substituted aryl, optionally substituted heteroalkyl, and optionally substituted heteroaryl;

R¹³ is independently selected from the group consisting of F, Cl, Br, I, OH, CN, optionally substituted alkyl, optionally substituted alkoxy, optionally substituted aryl, optionally substituted heteroalkyl, and optionally substituted heteroaryl;

R¹⁴ is independently selected from the group consisting of F, Cl, Br, I, OH, CN, optionally substituted alkyl, optionally substituted alkoxy, optionally substituted aryl, optionally substituted heteroalkyl and optionally substituted heteroaryl;

R¹⁵ is independently selected from the group consisting of F, Cl, Br, I, OH, CN, optionally substituted alkyl, optionally substituted alkoxy, optionally substituted aryl, optionally substituted heteroalkyl, and optionally substituted heteroaryl;

R¹⁶ is independently selected from the group consisting of F, Cl, Br, I, OH, CN, optionally substituted alkyl, optionally substituted alkoxy, optionally substituted aryl, optionally substituted heteroalkyl, and optionally substituted heteroaryl;

R¹⁷ is independently selected from the group consisting of F, Cl, Br, I, OH, CN, optionally substituted alkyl, optionally substituted alkoxy, optionally substituted aryl, optionally substituted heteroalkyl, and optionally substituted heteroaryl;

each R¹⁸ is independently selected from the group consisting of H, F, Cl, Br, I, OH, CN, optionally substituted alkyl, optionally substituted alkoxy, optionally substituted aryl, optionally substituted heteroalkyl, and optionally substituted heteroaryl; and n is selected from 0, 1, 2, 3, 4, 5 and 6; and any two groups of R¹² to R¹⁸ can optionally be joined together to form a carbocyclic or a heterocyclic ring.

The expression "alkyl" as used herein, unless specifically limited, denotes a $C_{1-12}$ alkyl group, suitably a $C_{1-8}$ alkyl group, e.g. $C_{1-6}$ alkyl group, e.g. $C_{1-4}$ alkyl group. Alkyl groups may be straight chain or branched. Suitable alkyl groups include, for example, methyl, ethyl, propyl (e.g. n-propyl and isopropyl), butyl (e.g. n-butyl, iso-butyl, sec-butyl and tert-butyl), pentyl (e.g. n-pentyl), hexyl (e.g. n-hexyl), heptyl (e.g. n-heptyl) and octyl (e.g. n-octyl). The term "alkyl" also comprises cycloalkyl groups. The expression "cycloalkyl", unless specifically limited, denotes a $C_{3-10}$ cycloalkyl group (i.e. 3 to 10 ring carbon atoms), more suitably a $C_{3-8}$ cycloalkyl group, e.g. a $C_{3-6}$ cycloalkyl group. Exemplary cycloalkyl groups include cyclopropyl, cyclobutyl, cyclopentyl, cyclohexyl, cycloheptyl and cyclooctyl. A most suitable number of ring carbon atoms is three to six.

The expression "heteroalkyl", unless specifically limited, refers to an alkyl group wherein one or more carbon atoms, preferably 1, 2 or 3, are replaced by heteroatoms selected from N, S and O.

The expressions "carbocyclyl" and "carbocyclic", unless specifically limited, denote any ring system in which all the ring atoms are carbon and which contains between three and twelve ring carbon atoms, suitably between three and ten carbon atoms and more suitably between three and eight carbon atoms. Carbocyclyl groups may be saturated or partially unsaturated, but do not include aromatic rings. Examples of carbocyclyl groups include monocyclic, bicyclic, and tricyclic ring systems, in particular monocyclic and bicyclic ring systems. Other carbocylcyl groups include bridged ring systems (e.g. bicyclo[2.2.1]heptenyl). A specific example of a carbocyclyl group is a cycloalkyl group. A further example of a carbocyclyl group is a cycloalkenyl group.

The expression "aryl", unless specifically limited, denotes a $C_{6-12}$ aryl group, suitably a $C_{6-10}$ aryl group, more suitably a $C_{6-8}$ aryl group. Aryl groups will contain at least one aromatic ring (e.g. one, two or three rings). An example of a typical aryl group with one aromatic ring is phenyl. An example of a typical aryl group with two aromatic rings is naphthyl.

The expressions "heterocyclyl" and "heterocyclyc", unless specifically limited, refer to a carbocyclyl group wherein one or more (e.g. 1, 2 or 3) ring atoms are replaced by heteroatoms selected from N, S and O. A specific example of a heterocyclyl group is a cycloalkyl group (e.g.

cyclopentyl or more particularly cyclohexyl) wherein one or more (e.g. 1, 2 or 3, particularly 1 or 2, especially 1) ring atoms are replaced by heteroatoms selected from N, S or O. Exemplary heterocyclyl groups containing one hetero atom include pyrrolidine, tetrahydrofuran and piperidine, and exemplary heterocyclyl groups containing two hetero atoms include morpholine and piperazine. A further specific example of a heterocyclyl group is a cycloalkenyl group (e.g. a cyclohexenyl group) wherein one or more (e.g. 1, 2 or 3, particularly 1 or 2, especially 1) ring atoms are replaced by heteroatoms selected from N, S and O. An example of such a group is dihydropyranyl (e.g. 3,4-dihydro-2H-pyran-2-yl-).

The expression "heteroaryl", unless specifically limited, denotes an aryl residue, wherein one or more (e.g. 1, 2, 3, or 4, suitably 1, 2 or 3) ring atoms are replaced by heteroatoms selected from N, S and O, or else a 5-membered aromatic ring containing one or more (e.g. 1, 2, 3, or 4, suitably 1, 2 or 3) ring atoms selected from N, S and O. Exemplary monocyclic heteroaryl groups having one heteroatom include: five membered rings (e.g. pyrrole, furan, thiophene); and six membered rings (e.g. pyridine, such as pyridin-2-yl, pyridin-3-yl and pyridin-4-yl). Exemplary monocyclic heteroaryl groups having two heteroatoms include: five membered rings (e.g. pyrazole, oxazole, isoxazole, thiazole, isothiazole, imidazole, such as imidazol-1-yl, imidazol-2-yl imidazol-4-yl); six membered rings (e.g. pyridazine, pyrimidine, pyrazine). Exemplary monocyclic heteroaryl groups having three heteroatoms include: 1,2,3-triazole and 1,2,4-triazole. Exemplary monocyclic heteroaryl groups having four heteroatoms include tetrazole. Exemplary bicyclic heteroaryl groups include: indole (e.g. indol-6-yl), benzofuran, benzthiophene, quinoline, isoquinoline, indazole, benzimidazole, benzothiazole, quinazoline and purine.

The expressions "alkoxyaryl", "carboxyaryl", "cyanoaryl", "haloaryl", "hydroxyaryl" and "heteroarylaryl", unless specifically limited, denote an aryl residue which is substituted by at least one alkoxy, carboxy, cyano, halo, hydroxy and heteroaryl group, respectively.

The expressions "alkoxyheteroaryl", "carboxyheteroaryl", "cyanoheteroaryl", "haloheteroaryl" and "hydroxyheteroaryl", unless specifically limited, denote a heteroaryl residue which is substituted by at least one alkoxy, carboxy, cyano, halo, and hydroxy group, respectively.

The expression "alk", for example in the expressions "alkoxy", "haloalkyl" should be interpreted in accordance with the definition of "alkyl". Exemplary alkoxy groups include methoxy, ethoxy, propoxy (e.g. n-propoxy), butoxy (e.g. n-butoxy), pentoxy (e.g. n-pentoxy), hexoxy (e.g. n-hexoxy), heptoxy (e.g. n-heptoxy) and octoxy (e.g. n-octoxy). Exemplary haloalkyl groups include fluoroalkyl e.g. $CF_3$; exemplary haloalkoxy groups include fluoroalkyl e.g. $OCF_3$.

The term "halogen" or "halo" comprises fluorine (F), chlorine (Cl), bromine (Br) and iodine (I).

The term "optionally substituted" refers to optional substitution by one or several groups independently selected from $C_{1-6}$ alkyl, $C_{1-6}$ heteroalkyl, $C_{1-6}$ carbocyclyl, $C_{1-5}$ heterocyclyl, and $C_{1-5}$ heteroaryl group, each of which may be substituted by one or several halogen atoms and/or hydroxyl groups; a halogen atom, cyano group, and hydroxyl group.

Stereoisomers

All possible stereoisomers of the claimed compounds are included in the present invention.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base, or by salt formation with an optically active base, such as quinine, quinidine, quinotoxine, cinkotoxine, (S)-phenylethylamine, (1R,2S)-ephedrine, (R)-phenylglycinol, (S)-2-aminobutanol, followed by fractional crystallization and regeneration of the free acid. The compounds may also be resolved by formation of diastereomeric esters or amides, followed by chromatographic separation and removal of the chiral auxiliary. Alternatively, the compounds may be resolved using a chiral HPLC column.

Polymorph Crystal Forms, Solvates, Hydrates

Furthermore, some of the individual crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention. The compounds, including their salts, can also be obtained in the form of their hydrates, or include other solvents used for their crystallization. In view of the close relationship between the free compounds and the compounds in the form of their salts, hydrates or solvates, whenever a compound is referred to in this context, a corresponding salt, solvate or polymorph is also intended, provided such is possible or appropriate under the circumstances.

Tautomers

As used herein, the term "tautomer" refers to the migration of protons between adjacent single and double bonds. The tautomerization process is reversible. Compounds described herein can undergo any possible tautomerization that is within the physical characteristics of the compound.

Pharmaceutically Acceptable Salts

As used herein, the term "pharmaceutically acceptable" embraces both human and veterinary use. For example, the term "pharmaceutically acceptable" embraces a veterinarily acceptable compound or a compound acceptable in human medicine and health care.

Salts, hydrates and solvates of the compounds of Formula I and physiologically functional derivatives thereof which are suitable for use in medicine are those wherein the counter-ion or associated solvent is pharmaceutically acceptable. However, salts, hydrates and solvates having non-pharmaceutically acceptable counter-ions or associated solvents are within the scope of the present invention, for example, for use as intermediates in the preparation of other compounds and their pharmaceutically acceptable salts, hydrates and solvates.

Suitable salts according to the invention include those formed with either organic and inorganic acids or bases.

Pharmaceutically acceptable acid addition salts include those formed from hydrochloric, hydrobromic, sulfuric, nitric, citric, tartaric, phosphoric, lactic, pyruvic, acetic, trifluoroacetic, triphenylacetic, sulfamic, sulfanilic, succinic, oxalic, fumaric, maleic, malic, mandelic, glutamic, aspartic, oxaloacetic, methanesulfonic, ethanesulfonic, arylsulfonic (for example p-toluenesulfonic, benzenesulfonic, naphthalenesulfonic or naphthalenedisulfonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalenes-acrylic), benzoic, 4-methoxybenzoic, 2- or 4-hydroxybenzoic, 4-chlorobenzoic, 4-phenylbenzoic, benzeneacrylic (for example 1,4-benzenediacrylic), isethionic acids, perchloric, propionic, glycolic, hydroxyethanesulfonic, pamoic, cyclohexanesulfamic, salicylic, saccharinic and trifluoroacetic acid. Pharmaceutically acceptable base salts include ammonium salts, alkali metal salts such as those of sodium and potassium, alkaline earth metal salts such as those of calcium and magnesium and salts with organic bases such as dicyclohexylamine and N-methyl-D-glucamine.

All pharmaceutically acceptable acid addition salt forms of the compounds of the present invention are intended to be embraced by the scope of the present invention.

Pharmaceutical Compositions

The pharmaceutical composition according to the present invention comprises a compound as described above and a pharmaceutically acceptable excipient.

As used herein, the term "pharmaceutical composition" is intended to encompass a product comprising the claimed compounds in the therapeutically effective amounts, as well as any product that results, directly or indirectly, from combinations of the claimed compounds. As used herein, the term "excipient" refers to a carrier, a binder, a disintegrator and/or a further suitable additive for galenic formulations, for instance, for liquid oral preparations, such as suspensions, elixirs and solutions; and/or for solid oral preparations, such as, for example, powders, capsules, gelcaps and tablets. Carriers, which can be added to the mixture, include necessary and inert pharmaceutical excipients, including, but not limited to, suitable suspending agents, lubricants, flavorants, sweeteners, preservatives, coatings, granulating agents, dyes, and coloring agents.

Therapeutic Applications

The present invention provides a bacQC inhibitor compound, i.e. a compound identified by the method for identifying an inhibitor of the bacQC according to the present invention and/or a compound according to any one of the above aspects <1>-<20>, or a pharmaceutical composition as described above for use in a method for treatment of the human or animal body. The present disclosure also provides a method for treatment of the human or animal body wherein the method comprises administration of a therapeutically effective amount of said compound or composition to a subject in need thereof.

The present invention further provides a bacQC inhibitor compound or a pharmaceutical composition as described above for use in a method for therapy or prophylaxis of a bacterial infection. The present disclosure also provides a method for therapy or prophylaxis of a bacterial infection wherein the method comprises administration of a therapeutically effective amount of said compound or composition to a subject in need thereof. The bacterial infection is preferably caused by a bacterium that expresses a Type II bacterial glutaminyl cyclase (bacQC). More preferably, the bacterial infection is caused by a bacterium selected from the group consisting of the genera *Porphyromonas, Prevotella* and *Tannerella*, preferably selected from the group consisting of the species *Porphyromonas gingivalis, Prevotella intermedia* and *Tannerella forsythia*.

The bacQC inhibitor compound or the pharmaceutical composition used in the methods according the present invention preferably selectively kill or selectively inhibit the growth of a bacterium selected from the group consisting of the genera *Porphyromonas, Prevotella* and Tannerella, preferably selected from the group consisting of the species *Porphyromonas gingivalis, Prevotella intermedia* and *Tannerella forsythia*, within a biofilm, whereas the remaining bacteria within the biofilm preferably remain essentially unaffected (i.e. are killed or their growth is inhibited to a significantly smaller extent). Said biofilm is preferably a complex biofilm, more preferably a naturally occurring biofilm, and even more preferably a naturally occurring oral biofilm.

The present invention further provides a bacQC inhibitor compound or a pharmaceutical composition for use in a method for therapy or prophylaxis of an acute, chronic or recurrent periodontal disease or condition. The major categories of periodontal diseases and conditions are classified in the groups of dental plaque-induced gingival diseases, chronic periodontitis, aggressive periodontitis, periodontitis as a manifestation of systemic diseases, necrotizing periodontal diseases, abscesses of the periodontium, periodontitis associated with endodontic lesions, peri-implant mucositis, peri-implantitis, and endodontic infections. In the present invention, the acute, chronic or recurrent periodontal disease is preferably selected from the group consisting of dental plaque-induced gingival diseases, chronic periodontitis, aggressive periodontitis, periodontitis as a manifestation of systemic diseases, necrotizing periodontal diseases, abscesses of the periodontium, periodontitis associated with endodontic lesions, peri-implant mucositis, peri-implantitis, and endodontic infections. The present disclosure also provides a method for therapy or prophylaxis of an acute, chronic or recurrent periodontal disease which is preferably selected from the group consisting of dental plaque-induced gingival diseases, chronic periodontitis, aggressive periodontitis, periodontitis as a manifestation of systemic diseases, necrotizing periodontal diseases, abscesses of the periodontium, periodontitis associated with endodontic lesions, peri-implant mucositis, peri-implantitis, and endodontic infections, wherein the method comprises administration of a therapeutically effective amount of a bacQC inhibitor compound or a pharmaceutical composition according to the present invention to a subject in need thereof. Further acute, chronic or recurrent periodontal diseases are described, e.g., in Armitage, A. *Ann Periodontol* 1999, 4, 1-6.

In one embodiment of the present invention, the inhibitor compound or the pharmaceutical composition according to the present invention is preferably used in any of the methods described above, wherein the route of administration is topical administration, and/or wherein the method is a nonsurgical method. In another embodiment, the inhibitor compound or the pharmaceutical composition according to the present invention is preferably used in any of the methods described above, wherein the route of administration is systemic administration, and/or wherein the method is a nonsurgical method.

The term "subject" as used herein refers to an animal, preferably a mammal, most preferably a human, who is or has been the object of treatment, therapy, prophylaxis, observation or experiment.

The term "therapeutically effective amount" as used herein means that amount of active compound or pharmaceutical agent that elicits the biological or medicinal response in a tissue system, animal or human being sought by a researcher, veterinarian, medical doctor or other clinician, which includes alleviation of the symptoms of the disease or disorder being treated.

EXAMPLES

Example 1: Identification and Preparation of Putative Bacterial Glutaminyl Cyclases (bacQC)

a) Identification

Bioinformatics analysis of the secretome of the oral pathogens P. gingivalis, T. forsythia, and P. intermedia (http://www.oralgen.laln.gov/) showed that about 80% of the secreted proteins bearing a signal peptide are cleaved at a Xaa-Gln peptide bond by the signal peptidase. The N-termini of the released proteins contain a pGlu-residue. This implies the existence of glutaminyl cyclases which seem to be essential for growth protein translocation across outer membrane and the growth of periodontal pathogens.

FIG. 1 shows an amino acid sequence alignment of human QC (hQC, SEQ ID NO: 4) and putative bacterial QC from P. gingivalis (PgQC, SEQ ID NO: 1) (A), and an amino acid sequence alignment of further putative QC P. intermedia (PiQC, SEQ ID NO: 2) and T. forsythia (TfQC, SEQ ID NO: 3) and P. gingivalis (PgQC, SEQ ID NO: 1) (B). Putative PgQC possesses a 25% identity to human QC. Furthermore, putative TfQC exhibits a 49% identity to PgQC and QC from P. intermedia possess a 42% identity to PgQC. Grey underlined cysteine residues reflects disulfide bridges in hQC which is missing in PgQC. Bold sequences in human QC reflects highly conserved residues of Type II QC. Grey sequences described putative signal sequences of PgQC and hQC Furthermore the typical metal binding motif Asp-Glu-His is presented in bold and underlined letters. A putative metal binding motif was also identified in TfQC and PiQC (B, bold letters). The alignments were prepared using program Clustal Omega at EMBL-EBlnet; (*) indicates positions which have a single, fully conserved residue, (:) indicates conservation between groups of strongly similar properties, (.) indicates conservation between groups of weakly similar properties (http://www.ebi.ac.uk/Tools/msa/clustalo/).

BLAST analysis revealed an open reading frame (ORF) encoding putative QC protein in P. gingivalis (WP_005874301). The primary structure of this putative QC protein shows a 25% identity to human QC. Furthermore, putative QC proteins were also identified in the genome of the oral pathogens P. intermedia (WP_014709208) and T. forsythia (WP_014225037) which shares a 42% or 49% identity to putative QC from P. gingivalis (FIG. 1). As shown by the amino acid alignment, conserved residues of human QC seem to be different in bacterial QCs from those conserved cysteine residues which form disulfide bound in human and other Type II QCs are presumably not presence in all three putative bacterial QC. However, highly conserved metal binding motif Asp144, Glu184 (Asp) and His322 of Type II QC (Wintjens et al., 2006) seem to be present in bacterial putative QC which could represent the catalytic center. The primary structures of these proteins may provide an indication that these proteins are actual QCs.

b) Preparation

FIG. 2 shows SDS-PAGE of purified recombinant putative bacterial QCs expressed in E. coli Rosetta(DE3)pLysS and purified as described in detail below. Therefore, 30 µg purified protein were loaded to 12% SDS-PAGE and visualized by coomassie staining, lane 1, PageRuler Broad Range unstained (Thermofisher Scientific), lane 2, His-PgQC, lane 3, HisPiQC and lane 5, HisTfQC. All three putative bacterial QCs possess a theoretical molecular mass of ≈37 KDa.

Host Strains and Media

E. coli strain DH5a or XL-1 blue (Stratagene) were used for cloning procedures. E. coli Rosetta(DE3)pLysS (Novagene) was used for protein expression. The alkaline phosphatase activity assay was performed in the CC118 pGP1-2 strain (Tabor, S. and Richardson, C. C. Proc. Natl. Acad. Sci. U.S.A. 1985, 82, 1074-1078; Manoil, C., J. J. Mekalanos and Beckwith, J. J. Bacteriol. 1990, 172(2), 515-518). All E. coli strains were grown in Luria-Bertani medium as indicated at 20° C., 30° C. or 37° C. Antibiotics (ampicillin [50 to 125 mg/liter], chloramphenicol [15 to 30 mg/liter], and kanamycin [25 mg/liter]) were added where appropriate. For preparation of solid media 1.5% agar (Roth) was added to corresponding broth.

Molecular Cloning of Plasmid Vectors Encoding the Bacterial QCs

All cloning procedures were performed applying standard molecular biology techniques. For protein expression, open reading frames (ORFs) of PgQC (SEQ ID NO: 1, putative QC from P. gingivalis), PiQC (SEQ ID NO: 2 putative QC from P. intermedia) and TfQC (SEQ ID NO: 3, putative QC from T. forsythia) were amplified using synthesized DNA sequences purchased from Eurofins Genomics as templates in a PCR to introduce a NheI/NdeI restriction site essential for direct cloning into the vector pET28a(+) (Novagen). For the construction of a PgQC-'PhoA fusion protein, putative pgQC with predicted signal sequence was subcloned into pET26b(+) via NheI/XhoI restriction site using primer pair $_{seq}$pgQC NdeI (forward) and seqpgQC XhoI reverse. Furthermore, pgQC with native signal sequence including a ribosome binding site of a pET26b(+) vector was amplified using primer pair $_{seq}$pgQC RBS NotI (forward) and $_{seq}$pgQC XbaI (reverse) to clone into the phoA expression vector pECD637. All Primers for cloning were purchased from Metabion and described in Table 1.

TABLE 1

Oligonucleotides used for cloning of bacQC constructs

| SEQ ID NO: | Primer | Sequence (5'→3') |
|---|---|---|
| 5 | pgQC NdeI (forward) | AAA CAT ATG AAC GGC AAT AAC ACA AGT GAA |
| 6 | pgQC NheI (reverse) | TTT GCT AGC TCA GTG TGA AGC GGC TTT |
| 7 | piQC NdeI (forward) | TTT CAT ATG AAA GGA AAA TCG TCT AAC |
| 8 | piQC NheI (reverse) | ATG CTA GCT TAC ATG CTG TAA AGC AC |

TABLE 1-continued

Oligonucleotides used for cloning of bacQC constructs

| SEQ ID NO: | Primer | Sequence (5'→3') |
|---|---|---|
| 9 | tfQC NdeI (forward) | TCA CAT ATG GGT CAG AAA AAT ACG ACA |
| 10 | tfQC NheI (reverse) | ATG CTA GCT TAT TTC TCA TTA TAA ATC AC |
| 11 | seqPgQC NdeI (forward) | AAA CAT ATG AAA AGA CTG ATA ACA ACA GGA GCA GCC TTT CTA CTG GCT GCT ACA CTC TCT GCC TGC AAC GGC AAT AAC ACA AGT GAA ACG |
| 12 | seqPgQC XhoI (reverse) | TTT CTC GAG GTG TGA AGC GGC TTT CAC |
| 13 | seqPgQC RBS NotI (forward) | TGG CGG CCG CTA AGA AGG AGA |
| 14 | seqPgQC XbaI (reverse) | TTT TCT AGA GTG TGA AGC GGC TTT CAC |

Expression of Bacterial QC as His Tag Fusion Protein or as 'PhoA Fusion Protein

The expression vector pET28a(+)::pgQC was transformed in *E. coli* Rosetta(DE3)pLysS. Bacteria were grown in Luria-Bertani medium containing kanamycin (25 μg/ml) and chloramphenicol (15 μg/ml) at 37° C. until the cell density reached an OD 600~0.6. The cultures were induced with 0.4 mM isopropyl β-D-1-thiogalactopyranoside and a 2% (v/v) ethanol volume was added followed by an incubation time for 16 h at 20° C. Cultures were harvested by centrifugation at 4° C. and 3900 g for 30 min and cell pellets were storage at −20°.

For expression of $_{seq}$PgQC-'PhoA fusion protein, recombinant vector pECD637::$_{seq}$pgQC was transformed into CC118 (lacking e.g. phoA gene) along with helper plasmid pGP1-2. Cultures were inoculated at 30° C. overnight. Furthermore overnight cultures were diluted into fresh Luria-Bertani media to a final optical density (OD600) ~0.4 followed by an incubation at 42° C. for 20 min to induce expression of $_{seq}$PgQC-'PhoA fusion proteins. Then cultures were inoculated for further 2 h at 30° C. Finally optical density OD600 was determined using spectrophotometer (BioRad) and 200 μl of cultures were harvested by centrifugation at 4° C. and 16000 g for 15 min for determination of PhoA activity.

Purification of Bacterial QCs

Cell pellet of 500 ml culture were resuspended in 20 ml buffer consists of 50 mM Tris-HCl, 150 mM NaCl pH 8.0, 10 μg/ml DNase and protease inhibitor cocktail mix (complete mini tablets, EDTA-free, Roche). Cells were disrupted by passing through French Press (Thermo Scientific, Waltman, MA, USA) for 3-4 times. Cell debris was removed by centrifugation at 4° C. and 30000 g for 30 min. Supernatant was 1:2 diluted with equilibration buffer and loaded on 5 ml HisTrap column (GE Healthcare). The column was equilibrated with 50 mM Tris-HCl containing 150 mM NaCl pH 8.0. After washing with several column volumes of equilibration buffer and at least with 20 mM imidazole protein were eluted using multiple step gradients, reaching a final concentration of 250 mM imidazole, whereas majority of pure protein was already eluted with approximately 100 mM imidazole. All bacQC containing fractions were pooled, concentrated with Vivaspin 20 (Sartorius AG) and applied to a HiPrep 26/10 desalting column (GE, Healthcare), which was equilibrated with 50 mM Tris-HCl, 150 mM NaCl pH 8.0. The purification was analyzed by SDS-PAGE and the protein content was determined by absorption at 280 nm using NanoDrop 2000 spectrophotometer (Thermo Scientifc) or according to the methods of Bradford or Gill and von Hippel (Bradford, M. M. 1976 Anal Biochem 72, 248-254; Gill, S. C. and von Hippel, P. H. 1989 Anal Biochem 182, 319-326). Finally purified recombinant fusion bacQC proteins were shock-frozen in liquid nitrogen and stored at −80° C. or glycerol was added to a final concentration of 50% and storage at −20° C. His Tag of N-terminal fusion proteins were removed using 1 Unit Thrombin per 1 mg fusion protein (Thrombin cleavage Capture Kit, Novagen) in presence of 20 mM Tris-HCl, 150 mM NaCl, 2.5 mM $CaCl_2$ at pH 8.0 followed by an incubation for 16 h at 4° C. Thrombin was removed through binding to Steptavidin Agarose (Thrombin cleavage Capture Kit, Novagen) and bacQC proteins without HisTag were recovered by spin-filtration. After further desalting step using HiPrep (26/10) bacQC fractions were pooled and concentrated with Vivaspin 20 (Sartorius AG). Finally recombinant bacQC in 50 mM Tris-HCl, 150 mM NaCl pH 8.0 was shock-frozen in liquid nitrogen and storage at −80° C. or glycerol was added to a final concentration of 50% and storage at −20° C. PiQC was expressed and purified in the same way like PgQC. TfQC was expressed in the same way like PgQC and purified using HiTrap Talon column (GE, Healthcare).

Conclusions:

All putative bacterial QC were expressed in *E. coli* Rosetta(DE3)pLysS without signal sequence as N-terminal His Tag fusion proteins and purified to homogeneity via affinity chromatography. 16-40 mg recombinant pure His-Tag fusion proteins were isolated from approximately 500 ml of induced *E. coli* cultures. Subsequently, His-tag of fusion proteins was cleaved by thrombin followed by enzymatic characterization of these putative bacterial QCs.

Example 2: Fluorometric Assay for Glutaminyl Cyclase Activity

QC activity was evaluated using H-Gln-AMC as the substrate (as previously described in Schilling et al., 2002).

The assay consists of varying concentration of the fluorogenic substrate and 0.5 U pyroglutaminyl aminopeptidase in 50 mM Tris-HCl, 50 mM NaCl at pH 8.0. After 10 minute incubation time at 30° C. reaction was initiated by addition of bacQC to a final volume of 125 μl reaction mixture. The excitation/emission wavelength was 380/460 nm. bacQC activity was determined from a standard curve of the fluorophore AMC under assay conditions. All determinations were carried out in 96 well microtiter plates (Fisher Scientific) at 30° C. using the FluoStar Optima (BMG Labtech). The kinetic data were evaluated using GraFit software (Version 7, Erithacus software Ltd., Horley, UK).

Figure 3:
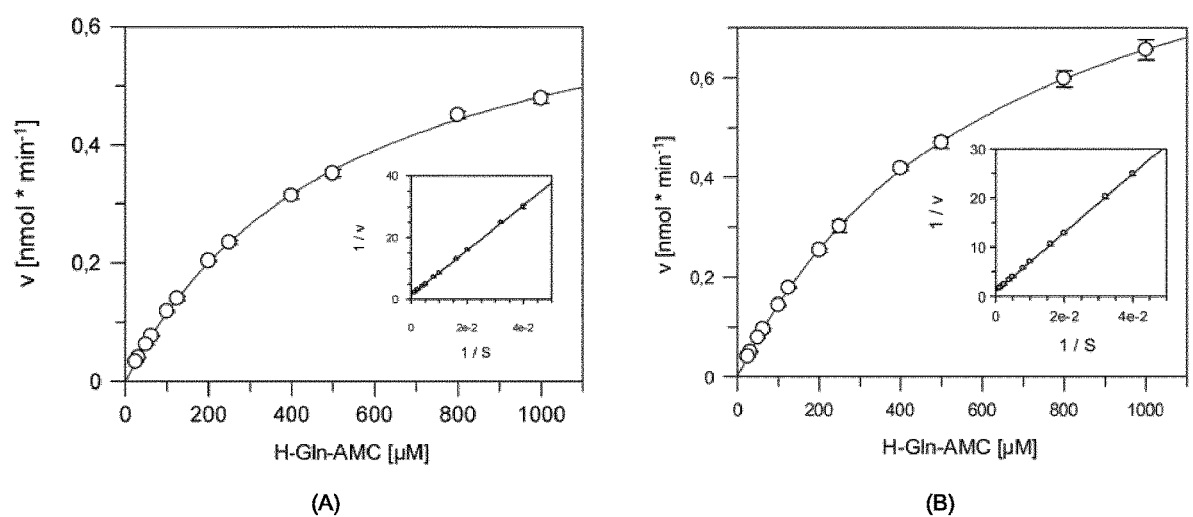
FIG. 3 shows Lineweaver-Burk plots for PgQC (A), PiQC (B) and TfQC (C) catalyzed cyclization of H-Gln-AMC.

FIG. 3 shows Lineweaver-Burk plots for PgQC (A), PiQC (B) and TfQC (C) catalyzed cyclization of H-Gln-AMC. The inset shows a secondary plot of the obtained slopes of the Lineweaver-Burk evaluation. bacQC activity measurement carried out in 50 mM Tris-HCl, pH 8.0 and 50 mM Tris-HCl at 30° C. The kinetic data were evaluated using GraFit software (Version 7, Erithacus software Ltd., Horley, UK). Enzymatic parameters of bacterial QC were determined (Table 2), which differ from those of hQC (Schilling, S., Manhart, S., Hoffmann, T., Ludwig, H.-H., Wasternack, C., and Demuth, H.-U. *Biol. Chem.* 2003, 384, 1583-1592).

TABLE 2

Kinetic parameters for the conversion of H-Gln-AMC by bacterial QC. Determination of kinetic parameters was carried out in 50 mM Tris-HCl pH 8 and 50 mM NaCl at 30° C.

| | $K_m$ [μM] | $k_{cat}$ [s$^{-1}$] | $k_{cat}/K_m$ [mM$^{-1}$ s$^{-1}$] |
|---|---|---|---|
| PgQC | 510.94 ± 13.3 | 4.71 ± 0.22 | 9.24 ± 0.28 |
| PiQC | 645.33 ± 7.4 | 8.51 ± 0.37 | 13.18 ± 0.05 |
| TfQC | 1091.67 ± 34.36 | 4.49 ± 0.22 | 4.1 ± 0.14 |

Conclusions:

Purified recombinant proteins were tested for enzymatic activity using fluorometric assay with H-Gln-AMC as substrate. H-Gln-AMC as substrate was turned over by these bacterial proteins resulted in an increase of RFU and therefore an increasing reaction rate (FIG. 3). The affinity for H-Gln AMC as substrate is, in the case of PgQC and PiQC, approximately tenfold lower than that of hQC for this substrate. The $K_m$ value of TfQC is actually 20-fold higher than the $K_m$ value of hQC. Furthermore, the efficiency of bacterial proteins seems to be similar to that of hQC whereat PiQC possesses a twofold higher turnover number comparing PgQC or TfQC.

Example 3: Inhibitor Assay for Glutaminyl Cyclase Activity

For inhibitor testing, the sample composition was the same as described above, except for the addition of the putative inhibitory compound. This resulted in presence of 1% or 2% (v/v) DMSO in reaction mixture. Inhibitory constants were determined using different concentration of H-Gln-AMC varying from ¼ $K_m$-2 $K_m$. Final concentration of bacterial QC was in a range between 25 nM-50 nM. The inhibitory constant was evaluated by fitting the set of progress curves to the general equation for competitive inhibition using GraFit software (Version 7, Erithacus software Ltd., Horley, UK).

Figure 4:
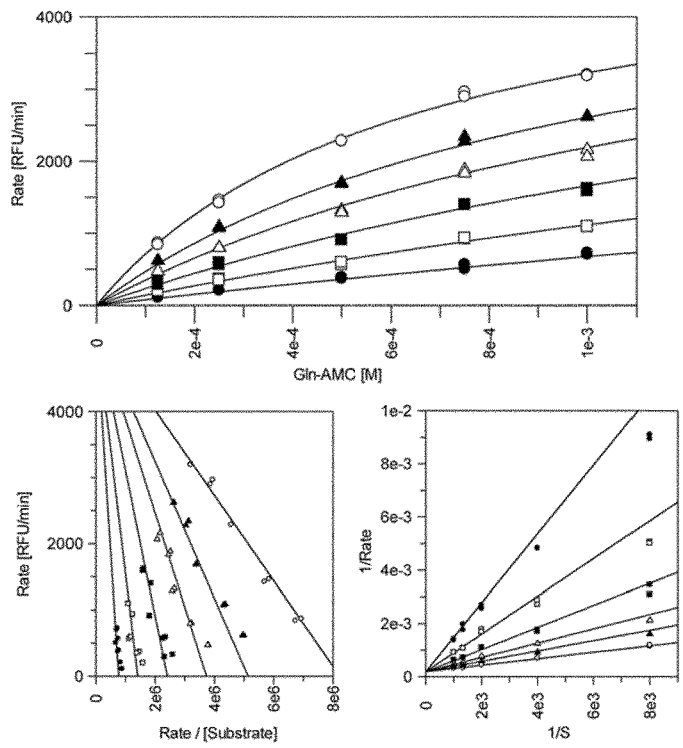
FIG. 4 shows exemplary v/S characteristics, Lineweaver-Burk and Eadie-Hofstee plots for PgQC-catalyzed cyclization of H-Gln-AMC in the presence of compound MWT-S-00431.

FIG. 4 shows exemplary v/S characteristics, Lineweaver-Burk and Eadie-Hofstee plots for PgQC catalyzed cyclization of H-Gln-AMC (A) in presence of (●) 1 μM, (□) 0.5 μM, (■) 0.25 μM, (Δ) 0.125 μM and (▲) 0.063 μM of MWT-S-00431. (○) represents reaction without inhibitor. Determinations were carried out in 50 mM Tris-HCl, 50 mM NaCl pH 8.0 and 1% (v/v) DMSO at 30° C. The kinetic parameters shown in Table 3 were obtained.

Conclusions:

PgQC is inhibited by compound MWT-S-00431. The substance exhibits a $K_i$ of 103.7±3.31 nM.

TABLE 3

Kinetic parameters for the inhibition of the conversion of H-Gln-AMC by PgQC in the presence of MWT-S-00431.

| Parameter | Value | Std. Error |
|---|---|---|
| Vmax [μM min$^{-1}$] | 4.41161 | 1.0569 · 10$^{-1}$ |
| $K_m$ [M] | 6.45485 · 10$^{-4}$ | 3.14087 · 10$^{-5}$ |
| $K_i$ [M] | 1.03698 · 10$^{-7}$ | 3.31239 · 10$^{-9}$ |

Furthermore, the following compounds were synthesized as described in Example 10 below. Average residual activity (RA) and average $K_i$ values for the inhibition of PgQC (isolated and purified as described in Example 1) were measured using the above inhibitor assay and are shown in Table 4. RA refers to the average residual QC activity of PgQC measured in the presence of a concentration c of the respective compound. $K_i$ refers to the average $K_i$ values measured as described above, and Std($K_i$) refers to the standard deviation of $K_i$.

TABLE 4

Inhibition of PgQC by bacQC inhibitors.

| Structure | ID | RA [%] | c [μM] | $K_i$ [nM] | Std($K_i$) [nM] |
|---|---|---|---|---|---|
| 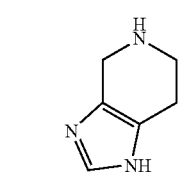 | MWT-S-00132 | 45 | 200 | 66700 | 2500 |
| 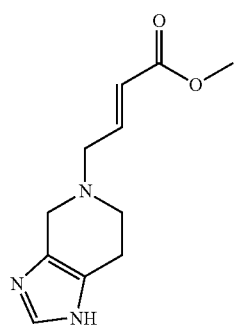 [SMILES: COC(=O)/C=C/CN1CCc2[nH]cnc2C1] | MWT-S-00138 | 21 | 20 | 3000 | 300 |

TABLE 4-continued

Inhibition of PgQC by bacQC inhibitors.

| Structure | ID | RA [%] | c [μM] | $K_i$ [nM] | Std($K_i$) [nM] |
|---|---|---|---|---|---|
| 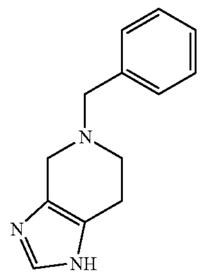 [SMILES: c1ccc(CN2CCc3[nH]cnc3C2)cc1] | MWT-S-00139 | 18 | 8 | 909 | 6 |
| 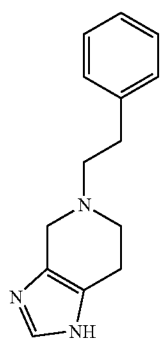 [SMILES: c1ccc(CCN2CCc3[nH]cnc3C2)cc1] | MWT-S-00145 | 21 | 40 | 6470 | 570 |
| 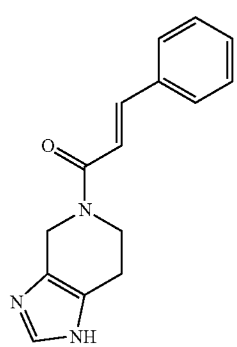 [SMILES: O=C(/C=C/c1ccccc1)N1CCc2[nH]cnc2C1] | MWT-S-00146 | 18 | 15 | 1580 | 40 |
| 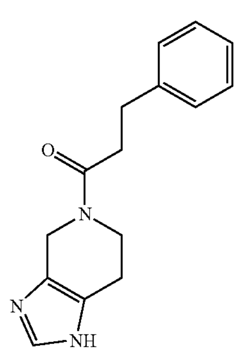 [SMILES: O=C(CCc1ccccc1)N1CCc2[nH]cnc2C1] | MWT-S-00147 | 22 | 12 | 1750 | 80 |

TABLE 4-continued

Inhibition of PgQC by bacQC inhibitors.

| Structure | ID | RA [%] | c [μM] | $K_i$ [nM] | Std($K_i$) [nM] |
|---|---|---|---|---|---|
| 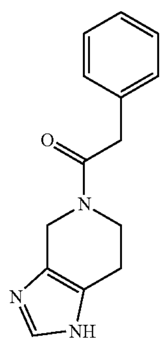 [SMILES: O=C(Cc1ccccc1)N1CCc2[nH]cnc2C1] | MWT-S-00148 | 29 | 8 | 1680 | 110 |
| 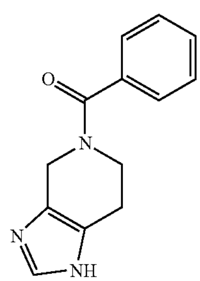 [SMILES: O=C(c1ccccc1)N1CCc2[nH]cnc2C1] | MWT-S-00149 | 20 | 4 | 435 | 21 |
| 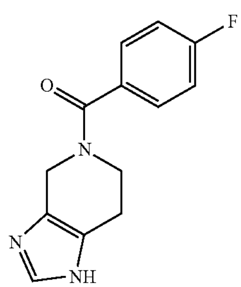 [SMILES: O=C(c1ccc(F)cc1)N1CCc2[nH]cnc2C1] | MWT-S-00156 | 24 | 5 | 879 | 10 |
| 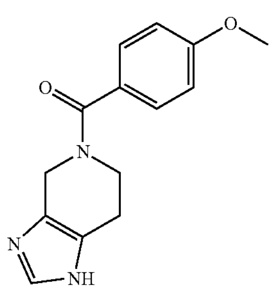 [SMILES: COc1ccc(C(=O)N2CCc3[nH]cnc3C2)cc1] | MWT-S-00157 | 24 | 5 | 833 | 69 |
| 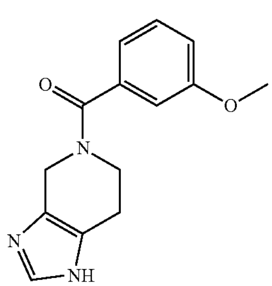 [SMILES: COc1cccc(C(=O)N2CCc3[nH]cnc3C2)c1] | MWT-S-00158 | 21 | 2 | 335 | 10 |

TABLE 4-continued

Inhibition of PgQC by bacQC inhibitors.

| Structure | ID | RA [%] | c [μM] | $K_i$ [nM] | Std($K_i$) [nM] |
|---|---|---|---|---|---|
| 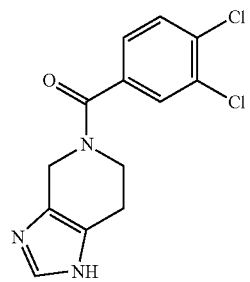 [SMILES: O=C(c1ccc(Cl)c(Cl)c1)N1CCc2[nH]cnc2C1] | MWT-S-00159 | 18 | 2 | 257 | 21 |
| 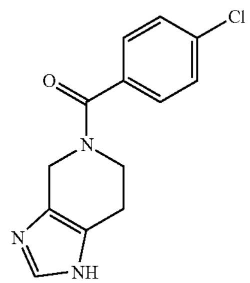 [SMILES: O=C(c1ccc(Cl)cc1)N1CCc2[nH]cnc2C1] | MWT-S-00160 | 20 | 5 | 681 | 34 |
| 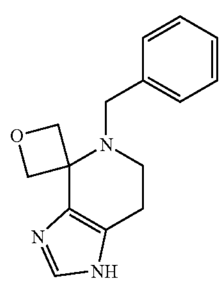 [SMILES: c1ccc(CN2CCc3[nH]cnc3C23COC3)cc1] | MWT-S-00260 | 22 | 10 | 1760 | 210 |
| 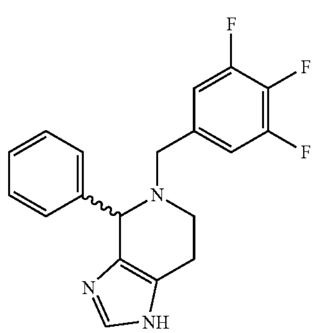 [SMILES: Fc1cc(CN2CCc3[nH]cnc3C2c2ccccc2)cc(F)c1F] | MWT-S-00261 | 93 | 20 | n.d. | |
| 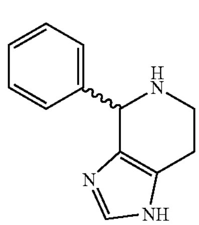 [SMILES: c1ccc(C2NCCc3[nH]cnc32)cc1] | MWT-S-00264 | 92 | 100 | n.d. | |

TABLE 4-continued

Inhibition of PgQC by bacQC inhibitors.

| Structure | ID | RA [%] | c [μM] | $K_i$ [nM] | Std($K_i$) [nM] |
|---|---|---|---|---|---|
| 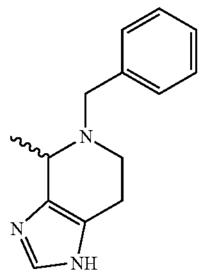 [SMILES: CC1c2nc[nH]c2CCN1Cc1ccccc1] | MWT-S-00265 | 21 | 20 | 3080 | 60 |
| 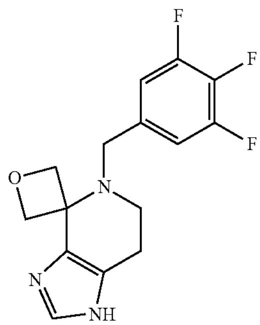 [SMILES: Fc1cc(CN2CCc3[nH]cnc3C23COC3)cc(F)c1F] | MWT-S-00266 | 19 | 4 | 556 | 65 |
| 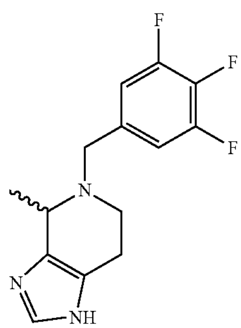 [SMILES: CC1c2nc[nH]c2CCN1Cc1cc(F)c(F)c(F)c1] | MWT-S-00267 | 20 | 4 | 528 | 64 |
| 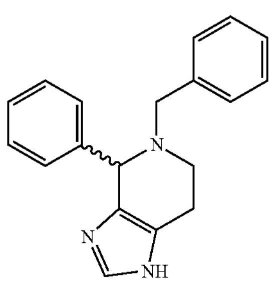 [SMILES: c1ccc(CN2CCc3[nH]cnc3C2c2ccccc2)cc1] | MWT-S-00268 | 93 | 16 | n.d. | |
| 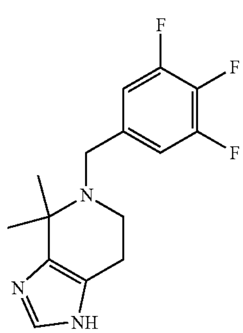 [SMILES: CC1(C)c2nc[nH]c2CCN1Cc1cc(F)c(F)c(F)c1] | MWT-S-00275 | 22 | 1 | 143 | 17 |

TABLE 4-continued
Inhibition of PgQC by bacQC inhibitors.
| Structure | ID | RA [%] | c [µM] | $K_i$ [nM] | Std($K_i$) [nM] |
|---|---|---|---|---|---|
| 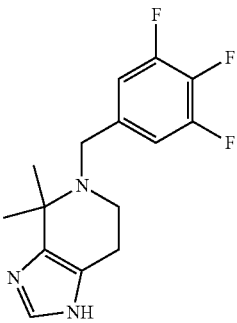 [SMILES: CC1(C)c2nc[nH]c2CCN1Cc1cc(F)c(F)c(F)c1] | MWT-S-00320 | 16 | 7.6 | 665 | 42 |
| 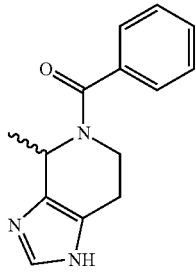 [SMILES: CC1c2nc[nH]c2CCN1C(=O)c1ccccc1] | MWT-S-00327 | 18 | 100 | n.d. | |
| 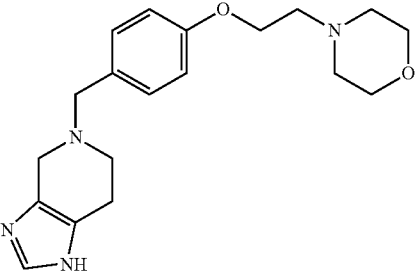 [SMILES: c1nc2c([nH]1)CCN(Cc1ccc(OCCN3CCOCC3)cc1)C2] | MWT-S-00330 | 22 | 8 | 940 | 100 |
| 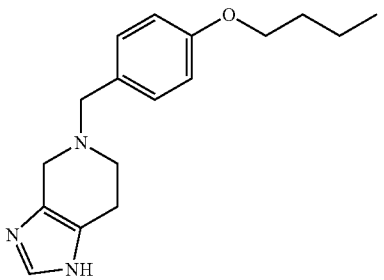 [SMILES: CCCCOc1ccc(CN2CCc3[nH]cnc3C2)cc1] | MWT-S-00331 | 26 | 1.5 | 254 | 39 |
| 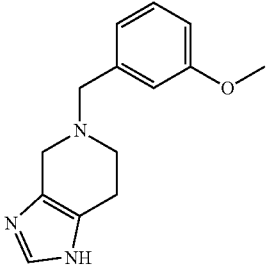 [SMILES: COc1cccc(CN2CCc3[nH]cnc3C2)c1] | MWT-S-00343 | 65 | 1 | n.d. | |

TABLE 4-continued
Inhibition of PgQC by bacQC inhibitors.
| Structure | ID | RA [%] | c [μM] | $K_i$ [nM] | Std($K_i$) [nM] |
|---|---|---|---|---|---|
| 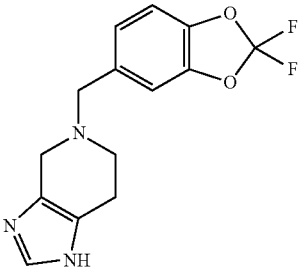 [SMILES: FC1(F)Oc2ccc(CN3CCc4[nH]cnc4C3)cc2O1] | MWT-S-00344 | 56 | 1 | n.d. | |
| 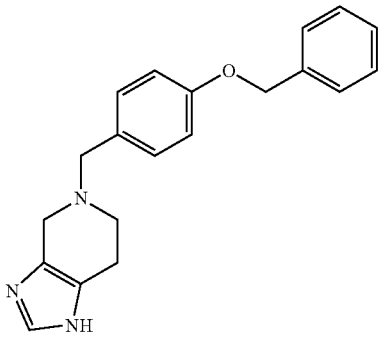 [SMILES: c1ccc(COc2ccc(CN3CCc4[nH]cnc4C3)cc2)cc1] | MWT-S-00359 | 31 | 1 | 192 | 1 |
| 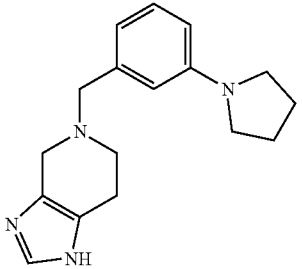 [SMILES: c1cc(CN2CCc3[nH]cnc3C2)cc(N2CCCC2)c1] | MWT-S-00361 | 80 | 1 | n.d. | |
| 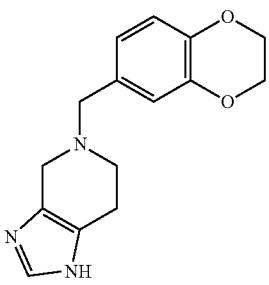 [SMILES: c1nc2c([nH]1)CCN(Cc1ccc3c(c1)OCCO3)C2] | MWT-S-00380 | 39 | 1 | 311 | 4 |
| 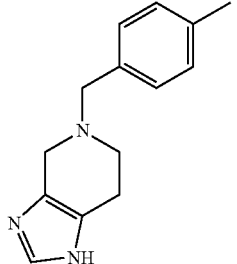 | MWT-S-00420 | 16 | 10 | 806 | 52 |

TABLE 4-continued
Inhibition of PgQC by bacQC inhibitors.
| Structure | ID | RA [%] | c [μM] | $K_i$ [nM] | $Std(K_i)$ [nM] |
|---|---|---|---|---|---|
| 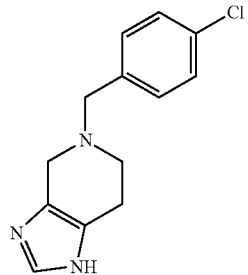 [SMILES: Clc1ccc(CN2CCc3[nH]cnc3C2)cc1] | MWT-S-00421 | 11 | 10 | 540 | 3 |
| 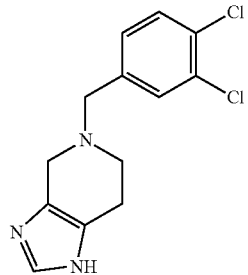 [SMILES: Clc1ccc(CN2CCc3[nH]cnc3C2)cc1Cl] | MWT-S-00423 | 8 | 10 | 367 | 23 |
| 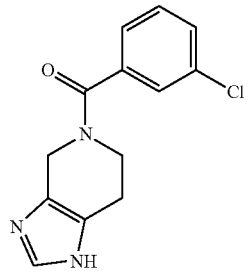 [SMILES: O=C(c1cccc(Cl)c1)N1CCc2[nH]cnc2C1] | MWT-S-00425 | 5 | 10 | 174 | 14 |
| 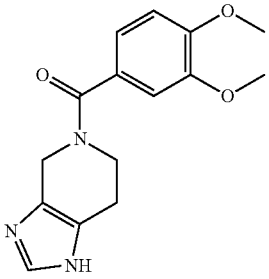 [SMILES: COc1ccc(C(=O)N2CCc3[nH]cnc3C2)cc1OC] | MWT-S-00426 | 26 | 10 | 1465 | 304 |
| 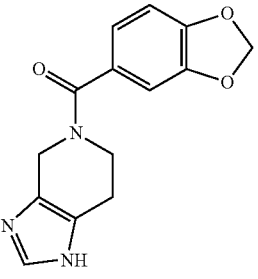 [SMILES: O=C(c1ccc2c(c1)OCO2)N1CCc2[nH]cnc2C1] | MWT-S-00427 | 13 | 10 | 560 | 4 |

TABLE 4-continued

Inhibition of PgQC by bacQC inhibitors.

| Structure | ID | RA [%] | c [μM] | $K_i$ [nM] | Std($K_i$) [nM] |
|---|---|---|---|---|---|
| 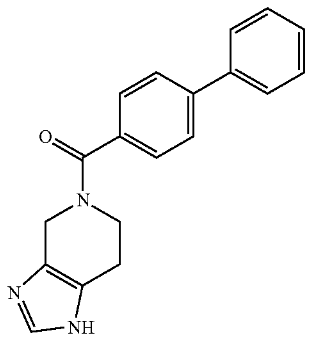 [SMILES: O=C(c1ccc(-c2ccccc2)cc1)N1CCc2[nH]cnc2C1] | MWT-S-00428 | 83 | 1 | 1900 | 71 |
| 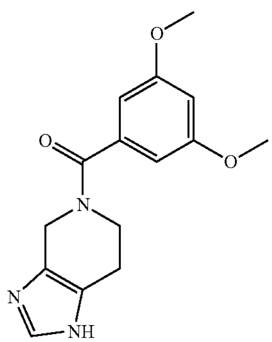 [SMILES: COc1cc(OC)cc(C(=O)N2CCc3[nH]cnc3C2)c1] | MWT-S-00429 | 16 | 10 | 928 | 21 |
| 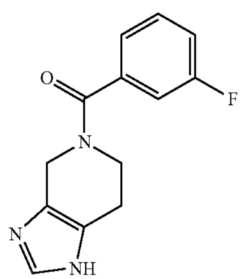 [SMILES: O=C(c1cccc(F)c1)N1CCc2[nH]cnc2C1] | MWT-S-00430 | 40 | 1 | 322 | 6 |
| 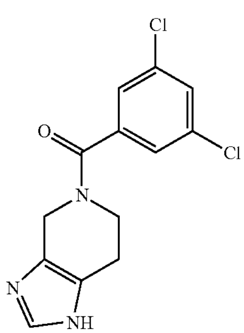 [SMILES: O=C(c1cc(Cl)cc(Cl)c1)N1CCc2[nH]cnc2C1] | MWT-S-00431 | 3 | 10 | 100 | 6 |
| 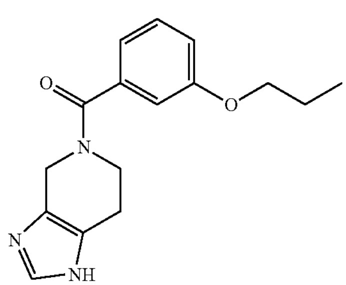 [SMILES: CCCOc1cccc(C(=O)N2CCc3[nH]cnc3C2)c1] | MWT-S-00432 | 2 | 100 | 780 | 24 |

TABLE 4-continued

Inhibition of PgQC by bacQC inhibitors.

| Structure | ID | RA [%] | c [μM] | $K_i$ [nM] | Std($K_i$) [nM] |
|---|---|---|---|---|---|
| 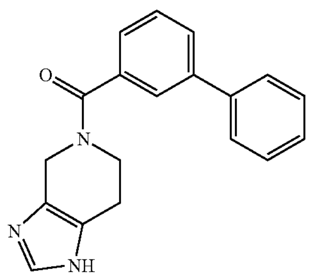 [SMILES: O=C(c1cccc(-c2ccccc2)c1)N1CCc2[nH]cnc2C1] | MWT-S-00433 | 47 | 1 | 547 | 41 |
| 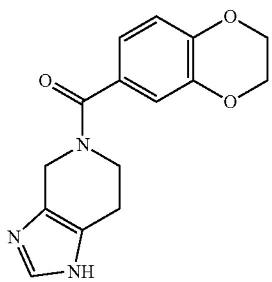 [SMILES: O=C(c1ccc2c(c1)OCCO2)N1CCc2[nH]cnc2C1] | MWT-S-00434 | 3 | 100 | 1335 | 219 |
| 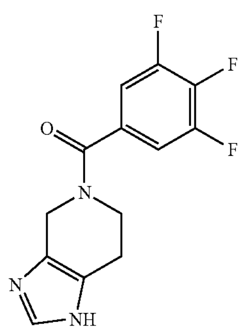 [SMILES: O=C(c1cc(F)c(F)c(F)c1)N1CCc2[nH]cnc2C1] | MWT-S-00435 | 16 | 10 | 904 | 7 |
| 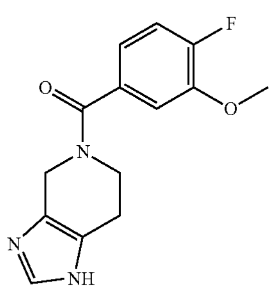 [SMILES: COc1cc(C(=O)N2CCc3[nH]cnc3C2)ccc1F] | MWT-S-00436 | 3 | 100 | 1240 | 113 |
| 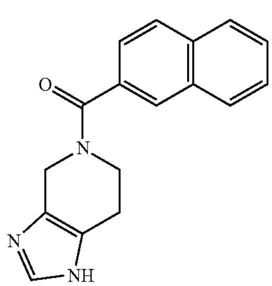 [SMILES: O=C(c1ccc2ccccc2c1)N1CCc2[nH]cnc2C1] | MWT-S-00440 | 4 | 10 | 126 | 9 |

TABLE 4-continued

Inhibition of PgQC by bacQC inhibitors.

| Structure | ID | RA [%] | c [µM] | $K_i$ [nM] | Std($K_i$) [nM] |
|---|---|---|---|---|---|
| (3-chloro-5-methoxyphenyl)(1,4,6,7-tetrahydro-5H-imidazo[4,5-c]pyridin-5-yl)methanone | MWT-S-00441 | 17 | 1 | 87 | 6 |

Example 4: pH and Ionic Strength Dependency of Bacterial QC Activity

QC activity at different pH ranges and furthermore at different concentrations of sodium chloride was assayed fluorometrically as described above. For investigations of pH dependency, a 3-component buffer consisting of 0.05 M acetic acid, 0.05 M MES, 0.1 M Tris and 0.05 M NaCl at pH ranges from 6.0 to 8.5 was used. This buffer provides a constant ionic strength over a broad pH range. All bacQC activity determinations were carried out under first-order rate law conditions, i.e. at substrate concentrations at $^{1}/_{10}$ $K_m$. Thus, the results represent the pH-dependency of the specificity constant $k_{cat}/K_m$. Because of the reduced stability of the auxiliary enzyme pyroglutamyl aminopeptidases under acid or basic conditions, pH dependency of bacQCs cannot be determined below pH 6 or above pH 9. The resulting kinetic data were evaluated by applying a three-inflection-point mathematical model (bell-shaped curve) using GraFit software (version 7, Erithacus software Ltd., Horley, UK). For investigations of ionic strength dependency on bacQC activity, different sodium chloride concentrations in a range from 0-500 mM were applied in an activity assay and the residual bacQC activity was determined under assay conditions.

Figure 5:
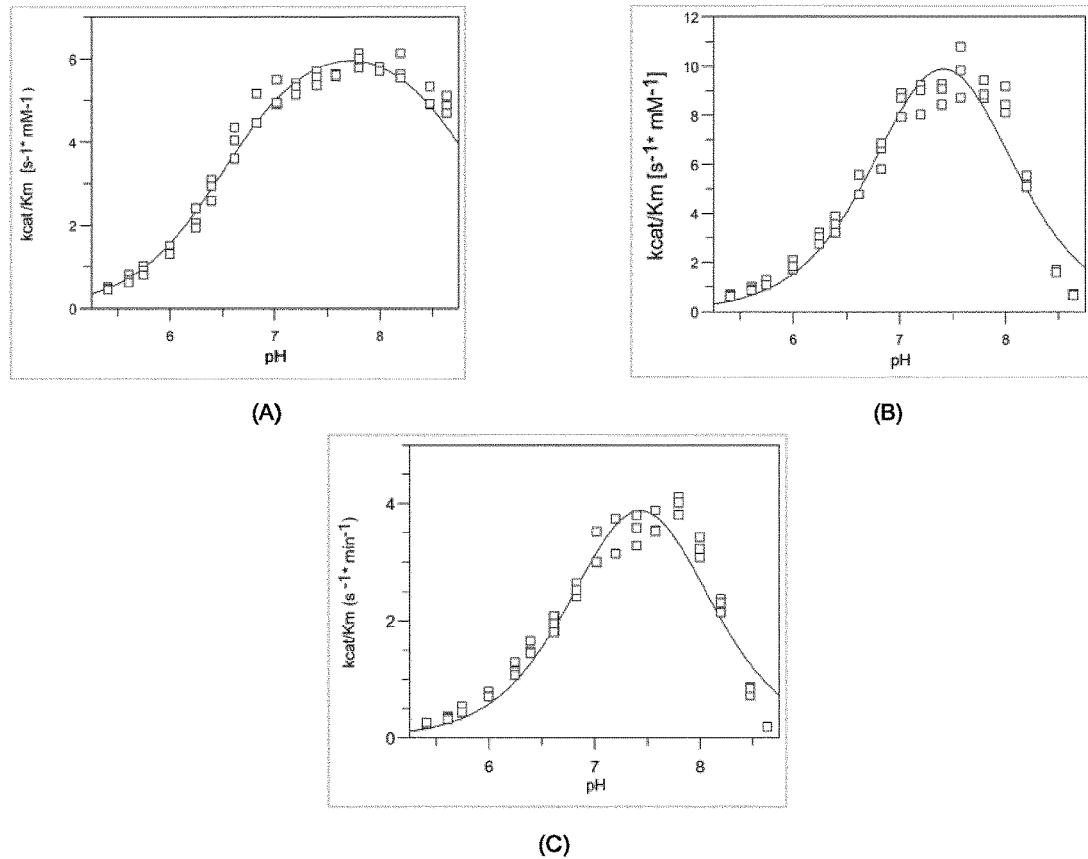
FIG. 5 shows the pH dependency of PgQC activity (A), PiQC activity (B) and TfQC activity (C).

FIG. 5 shows the pH dependency of PgQC activity (A), PiQC activity (B) and TfQC activity (C). The specific constants $k_{cat}/K_m$ of PgQC (A), PiQC (B) and TfQC (C) for the conversion of H-Gln-AMC were determined under first-order rate low conditions whereas substrate concentrations were $^{1}/_{10}$ $K_m$ and therefore [S]<<$K_m$. All determinations were carried out at 30° C. in buffer consisting of 0.1 M Tris-HCl, 0.05 MES, 0.05 mM acetic acid and 0.05 mM NaCl.

TABLE 5

Determination of pKa values of bacterial QCs under first-order rate low conditions

|  | pKa1 | pKa2 | pH optimum |
|---|---|---|---|
| PgQC | 6.50 ± 0.035 | 8.93 ± 0.014 | 7.71 ± 0.007 |
| PiQC | 6.97 ± 0.099 | 7.82 ± 0.057 | 7.36 ± 0.07 |
| TfQC | 7.05 ± 0.016 | 7.81 ± 0.037 | 7.43 ± 0.003 |

Conclusions:

Enzymatic activities of bacterial QC were determined at different pH ranges. The rate profiles obtained fit to classical bell-shaped curves in each case (FIG. 5). PgQC (A) exhibits maximum activity in the mild alkaline range, with pKa1=6.5±0.035 and pKa2=8.93±0.014 (Table 5). bacQC of P. intermedia (B) and T. forsythia (T) shows maximum activity at around neutral pH with and pKa1=6.97±0.99 and pKa2=7.92±0.057 for PiQC and pKa1=7.05±0.016 and pKa2=7.81±0.037 for TfQC (Table 5). PgQC possess high enzymatic activity over broader pH range than PiQC and TfQC which is indicated by increased distance between pKa1 and pKa2 values.

Figure 6:
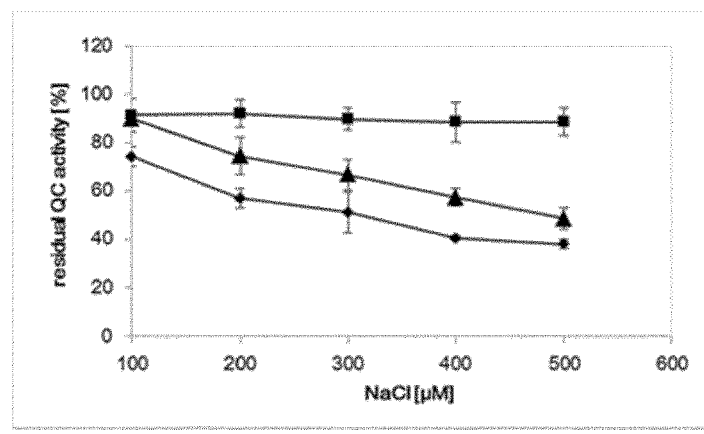
FIG. 6 shows the influence of ionic strength on bacterial QC activity.

FIG. 6 shows the influence of ionic strength on bacterial QC activity. bacQC activity was determined in presence of different concentrations of sodium chloride. Measurements were performed in 50 mM Tris-HCl and up to 500 µM potassium chloride. All reactions were carried out at 30° C. and described above. (■) indicates residual PgQC activity, (▲) indicates residual PiQC activity and (♦) indicates residual TfQC activity.

Conclusions:

In contrast to PgQC, the enzymatic activity of PiQC and TfQC decreases by increasing potassium chloride concentrations; 500 µM sodium chloride resulted in approximately 50% residual activity (FIG. 6). This is an important aspect for the performance of activity assay in accordance to physiological circumstances in saliva. Under physiological conditions, sodium chloride is present in the saliva, and therefore activity assay for bacterial QCs were always performed in the presence of 50 µM sodium chloride.

Example 5: Inhibition of Bacterial QC by Metal Chelators

Time-dependent turnover of ½ $K_m$ H-Gln-AMC in the presence of different concentrations of 1,10-phenanthroline, dipicolinic acid or EDTA at low bacQC concentrations (4 nM) should provide an indication for metal dependent catalysis of bacterial QC. The fluorometrically activity assay was carried out as described above, except the presence of 1% (v/v) DMSO in the case of 1,10-phenanthroline or dipicolinic acid. Finally the residual bacQC activity was determined at steady state whereas bacQC without Chelators and +/−1% DMSO served as positive control.

Figure 7:
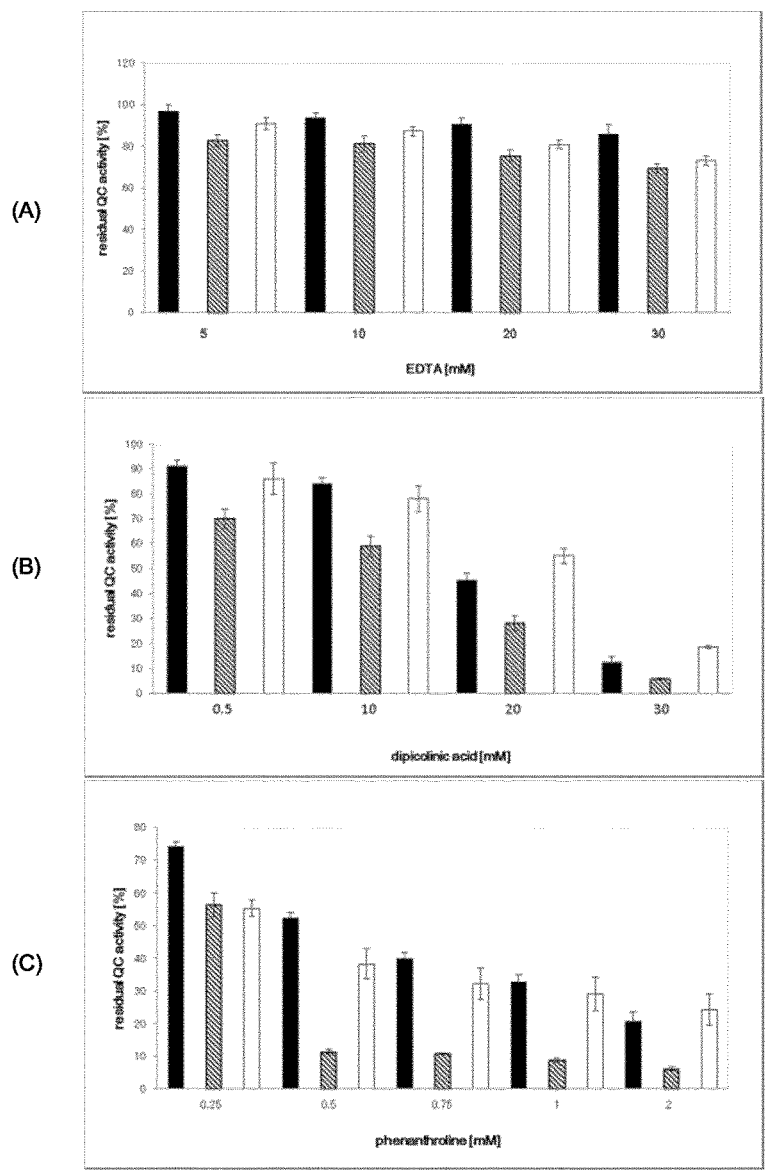
FIG. 7 shows the inhibition of bacterial QC activity by different metal chelators: EDTA (A), dipicolinic acid (B), and 1,10-phenantroline (C).

FIG. 7 shows inhibition of bacterial QC activity by different metal chelators: (A) EDTA, (B) dipicolinic acid and (C) 1,10-phenanthroline. 250 µM H-Gln-AMC and increasing concentrations of chelators were used to investigate the inhibitory effect on bacQC activity. The reaction was initiated by adding approximately 5 nM bacQC. Black bars indicate residual PgQC activity, striped bars represent residual PiQC activity, and white bars display residual TfQC activity. All determinations were carried out at 30° C. as described above.

Conclusions:

Amino acid alignments with human QC revealed putative metal binding sites in the active center of bacterial QCs. This suggested that bacterial QC acts as metal dependent enzymes as previously described for human QC (Schilling et al., 2002). Therefore bacterial QC activity should be determined in presence of different metal chelators to investigate a metal dependent catalysis. As shown in FIG. 7A, EDTA even at high concentrations does not influence bacQC activity, in contrast to dipicolinic acid (B) or phenanthroline (C) that show strong inhibitory activity towards all three bacterial QC. Phenanthroline inhibited QC activity already at low mM range, and especially PiQC seems to be sensitive against phenanthroline. In summary, QC activity is inhibited by metal depletion caused by metal chelators suggesting bacterial QCs are metalloenzymes.

Example 6: CD Spectroscopic Analysis of Bacterial QCs

Figure 8:
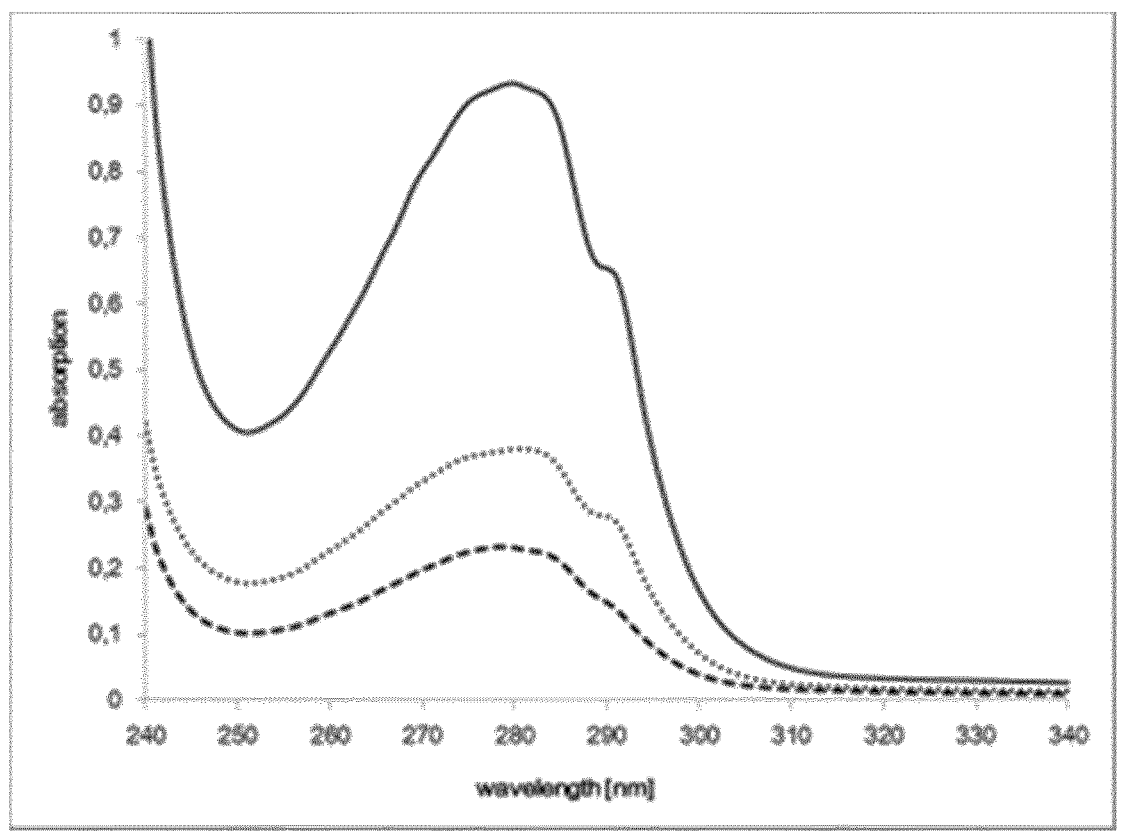
FIG. 8 shows UV-Spectra of recombinant bacterial QCs.

FIG. 8 shows UV-Spectra of recombinant bacterial QCs. Recombinant bacterial QCs were dialysis against 10 mM $NaH_2PO_4$, 50 mM NaCl pH 8.0. UV-spectrum between 240 nm and 340 nm was measured with the UV-Spectrometer Specord 210 plus (Analytic Jena). The thickness of the sample was 1 cm. Black line represent UV spectrum of 0.525 mg/ml PgQC, dotted line displays UV spectrum of 0.209 mg/ml PiQC, and broken line displays UV spectrum of 0.142 mg/ml TfQC.

Figure 9:
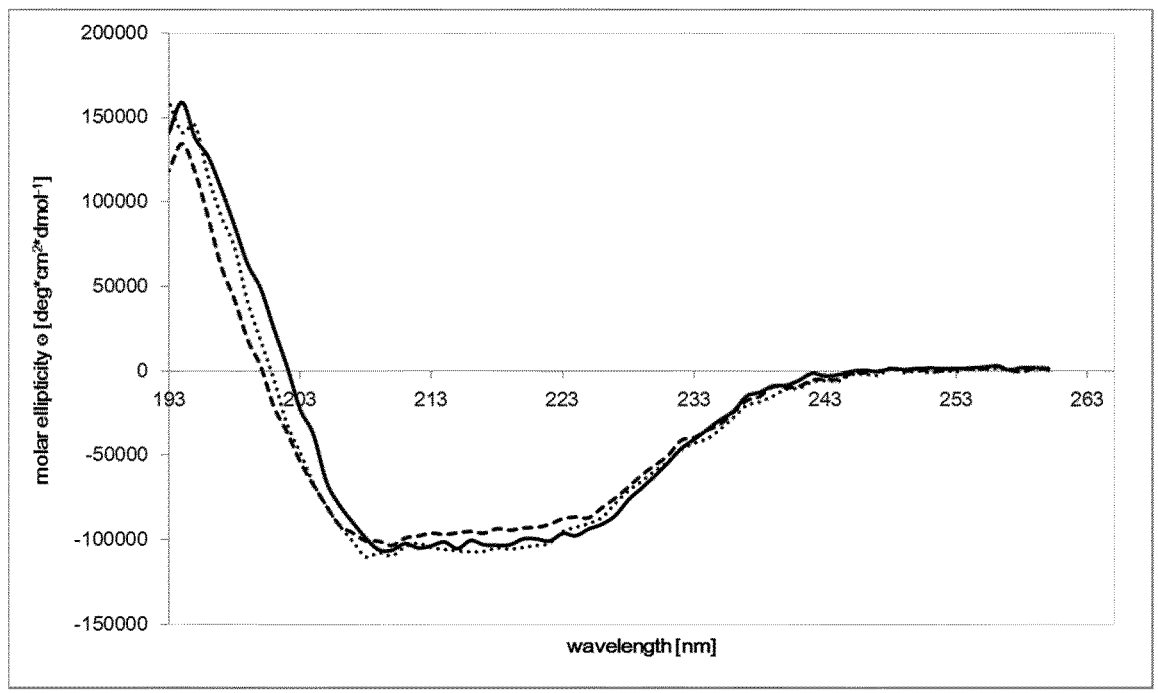
FIG. 9 shows a CD spectroscopic analysis of recombinant bacterial QCs.

FIG. 9 shows a CD spectroscopic analysis of recombinant bacterial QCs. Purified bacQCs without His Tag were dialyzed against 10 mM $NaH_2PO_4$, 50 mM NaCl pH 8.0, and diluted to a final concentration of approximately 0.05 mg/ml. Spectral analysis of recombinant bacQCs were measured at 20° C. with Jasco J-710 spectropolarimeter (Jasco GmbH, GroR-Umstadt) between 190 and 260 nm using quartz cuvettes of 0.1 cm path length, with 20 accumulations and 1 s integration. The spectra were corrected by subtracting the buffer spectra. The percentage of secondary structure elements were calculated using the Jasco secondary structure estimation program based on the method of Yang et al. (Yang, J. T., Wu, C. S., and Martinez, H. M. Methods Enzymol. 1986, 130, 208-269).

Conclusion:

Further characterization of recombinant bacterial QCs were performed by applying CD spectroscopy (FIG. 9). CD spectra were virtually identical of all bacterial QCs this support the strong similarity between PgQC, PiQC and TfQC globular domains. Spectrum of proteins with high a helical content exhibits two typical minima at 208 nm and 222 nm in their secondary structures which were also observed for PgQC, PiQC and TfQC. Additionally a calculation of quantities of α-helix, β-sheet, turn, and random structure according to the method of Yang et al., indicating similar folding patterns of all three proteins and suggesting an alp topology.

Example 7: Thermal Stability of Bacterial QC

Figure 10:
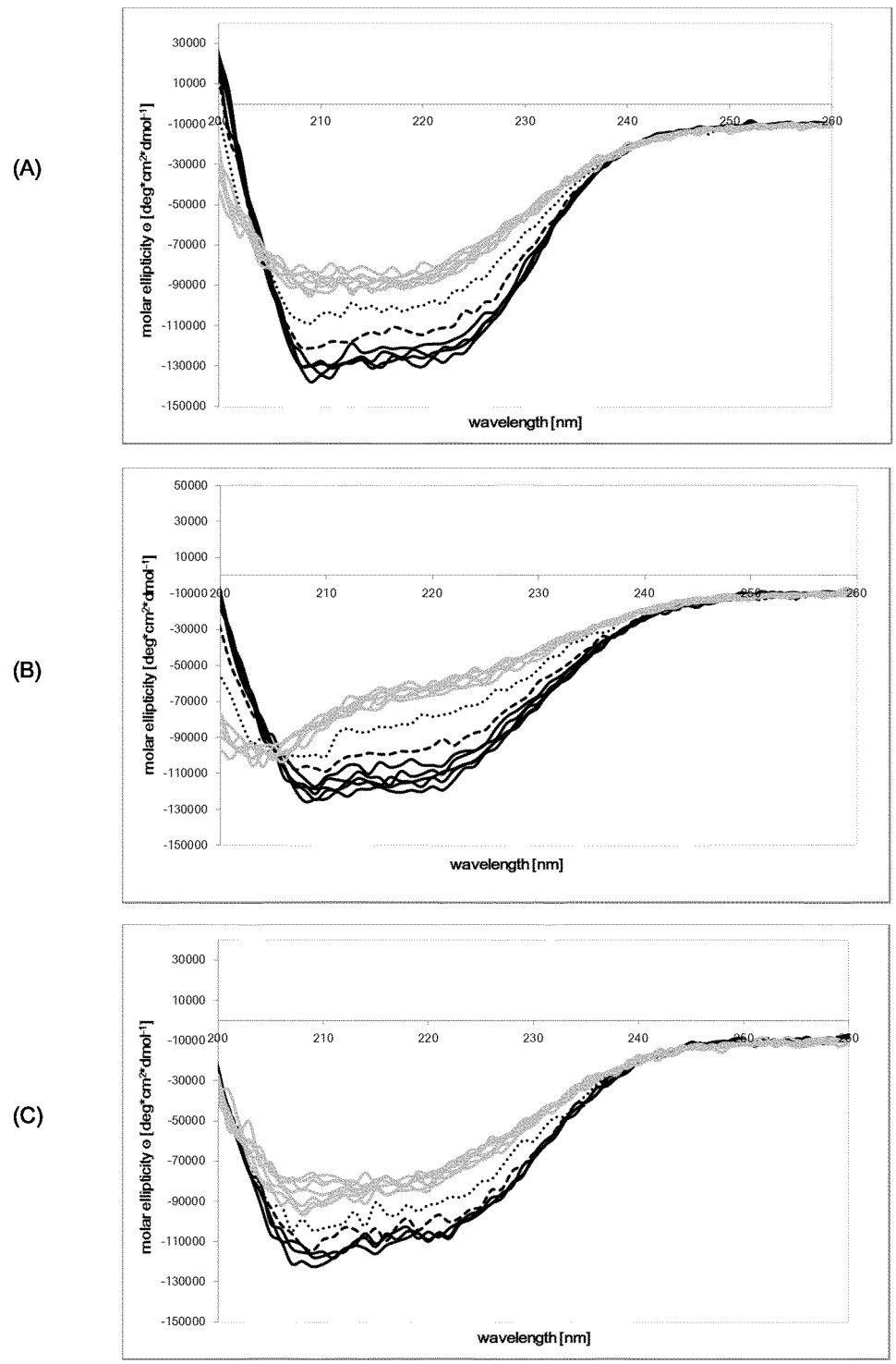
FIG. 10 shows the thermal stability of recombinant bacterial QCs: PgQC (A), PiQC (B), and TfQC (C).

FIG. 10 shows the thermal stability of recombinant bacterial QCs: PgQC(A), PiQC (B), and TfQC (C). Purified bacQCs without His Tag were dialyzed against 10 mM $NaH_2PO_4$, 50 mM NaCl pH 8.0 and diluted to a final concentration of approximately 0.05 mg/ml. The CD-spectrum was measured at temperature from 20° C. up to 80° C. with Jasco J-710 spectropolarimeter between 200 and 260 nm. Measurements carried out in 5° C. intervals, 10 accumulations with heat rate of 30 K/h, 1 s integration, and 1 mm thickness of the sample. Temperature equilibrated 180 s before each measurement. Striped and dotted line indicates temperature transitions for PgQC (A) and TfQC (C) at 40° C. and 45° C., and for PiQC (B) at 45° C. and 50° C. Black lines indicate temperature from 20° C. to 35° C. for PgQC (A) and TfQC (C), and for PiQC (B) temperature from 20° C. to 40° C. Lines in grey represent, in the case of PgQC (A) and TfQC (C) temperature from 50° C. to 80° C., and for PiQC (B) temperature from 55° C. to 80° C.

Conclusion:

CD spectra can be used for analyzing of altered secondary structure in dependency of different environmental conditions. Therefore changes in secondary structure of recombinant proteins were observed using CD with increasing temperature from 20° C. to 80° C. As shown in FIGS. 10A and C, the spectra of PgQC and TfQC changed starting from a temperature of 40° C., which indicates a starting point of denaturation. The spectrum of PiQC (FIG. 10B) changed starting from a temperature of 45° C. All three proteins were fully denaturated at 50° C. This indicates a thermal stability up to 40° C. for PgQC and TfQC, and up to 45° C. for PiQC.

Example 8: Determination of $_{seq}$QC-'PhoA Activity

Figure 11:
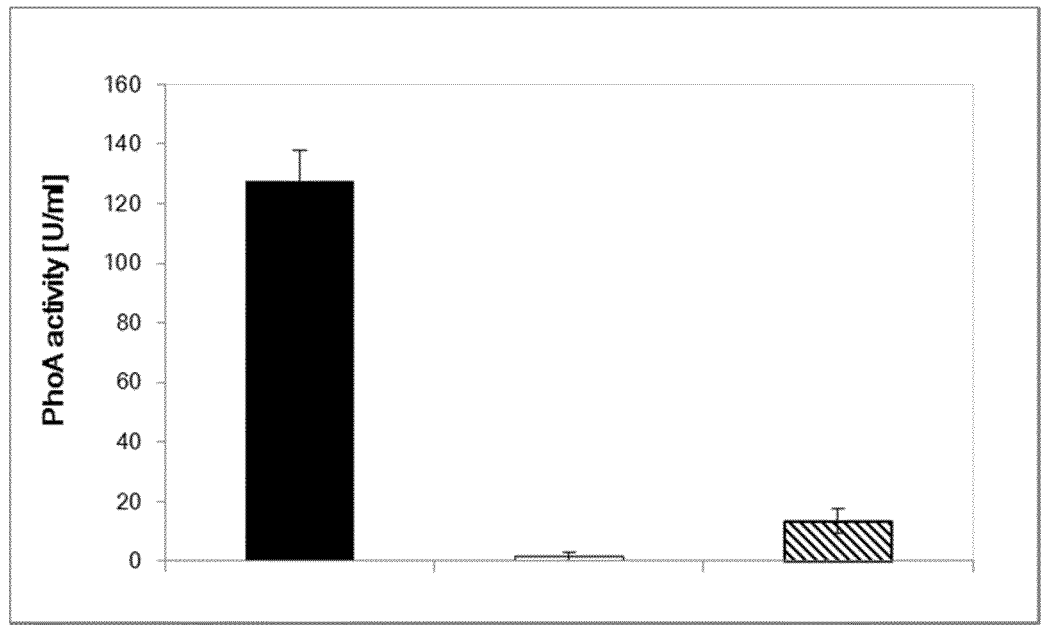
FIG. 11 shows PhoA activity in permeabilized *E. coli* CC118 pGP1-2 cells expressing seqPgQC-'PhoA fusion proteins.

FIG. 11 shows the PhoA activity in permeabilized E. coli CC118 pGP1-2 cells expressing $_{seq}$PgQC-'PhoA fusion proteins. PgQC with native putative signal sequence was cloned in pECD637 create a $_{seq}$PgQC-'PhoA fusion protein. Resulted vector was transformed into E. coli strain CC118 pGP1-2. The expression of fusion protein was initiated by incubation of the culture at 42° C. for 20 min. The PhoA activity of the induced culture was determined as described previously (Pribyl, T., Topologie des CzcCBA-Efflux-Komplexes aus Ralstonia metallidurans CH34. Dissertation, 2001, Martin-Luther-University Halle-Wittenberg). Black bar represent PhoA activity of E. coli cells expressing $_{seq}$PgQC-'PhoA, striped bar displays PhoA activity of cells expressing 'BlaM-'PhoA and served as positive control and cells expressed vector without insert were used as negative control (blank bar).

PhoA activity was determined from cultures grown as described above using chromogenic substrate p-nitrophenylphosphate (PNPP) (Pribyl, 2001). Therefore 200 μl cell suspension with known OD600 was harvested at 13000 rpm at 4° C. for 10 min. Cell pellet was washed in 0.5 ml 10 mM Tris-HCl pH 8.0, 10 mM $MgSO_4$ und 1 mM iodoacetamide. Resulted cell pellet was resuspended in 1 ml 1 M Tris-HCl pH 8.0, 0.1 mM $ZnCl_2$ und 1 mM iodoacetamide. Then 50 μl 0.1% (w/v) SDS and 50 μl Chloroform was added to the mixture followed by an incubation time for 5 min at 37° C. The reaction was then initiated by addition of 100 μl substrate solution (1 M Tris-HCl pH 8.0, 0.4% (w/v) PNPP). The reaction mixture was furthermore incubated at 37° C. until the solution turns yellow. The reaction was then stopped by addition of 120 μl 1 M $KH_2PO_4$, 0.5 M EDTA pH 8.0. The time taken to develop a yellow coloration defined specific enzymatic PhoA activity. Cell debris was removed by centrifugation (13000 rpm, 20 min) and optical density at 420 nm was determined of supernatant. PhoA activity was determined according to the Lambert-Beer law. E. coli CC118 pGP1-2 cultures bearing the empty vector pECD637 served as negative control whereas *E. coli* CC118 pGP1-2 with pECD619 (Pribyl, 2001) served as positive control. This plasmid encodes a short form of β-lactamase ('blaM) inclusive signal sequence downstream of 'phoA domain.

Conclusion:

In silico analysis of open reading frame of PgQC revealed a putative signal sequence. This indicates a localization of PgQC outside the cytoplasm in *P. gingivalis*. C-terminal fusions of PgQC inclusive "native" signal sequences with alkaline phosphatase (PhoA) were constructed to investigate the "nature" localization of PgQC. Fusions with alkaline phosphatases are exclusively active when localized in the periplasm. Expression of $_{seq}$PgQC-'PhoA resulted in high phosphatase activity of 638.5 U/I±50.9 (FIG. 11). This indicates that PgQC is localized in the periplasm.

Example 9: Antibodies Against PgQC, TfQC and PiQC

Polyclonal antibodies were generated by 5-step immunization procedure of rabbits using the expressed and purified full protein of PgQC, TfQC, and PiQC, respectively (without the HisTag), and subsequent purification of the antiserum.

Figure 12:
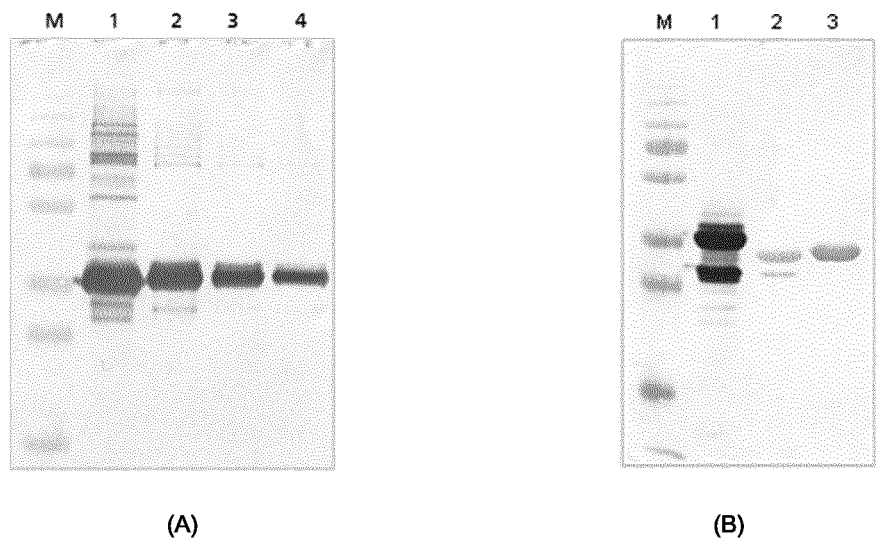
FIG. 12 shows the specifity of polyclonal antiserum against (A) PgQC and (B) TfQC and PiQC.

FIG. 12 shows the specifity of a polyclonal antiserum against (A) PgQC, and (B) TfQC and PiQC. (A): A polyclonal antiserum of PgQC was used in a 1:10000 dilution for detection of lane (1) crude extract of *E. coli* cells expressing PgQC; lane 2, 5 μg purified HisPgQC, lane 3, 0.5 μg HisPgQC, and lane 4, 0.05 μg purified PgQC in western blot. (B): Furthermore, polyclonal PgQC antibody was tested for detection of 5 μg PiQC (lane 2), and 5 μg HisTfQC (lane 3). 5 μg HisPgQC (lane 1) served as positive control. PageRuler Plus Prestained (Fermentas) served as a molecular standard.

Conclusion:

Polyclonal antibodies against PgQC that exhibits high affinity and specifity for PgQC were generated. PiQC and TfQC were also detected with comparatively lower affinity by this polyclonal antibody.

Example 10: Detailed Description of Synthetic Methods

Scheme 1

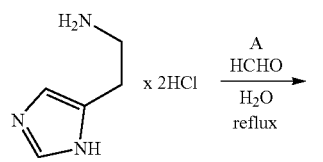

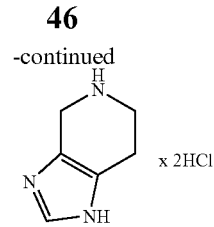

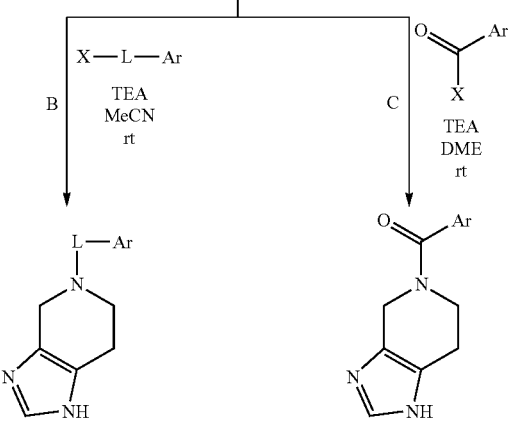

Method A:

4,5,6,7-Tetrahydro-1H-imidazo[4,5-c]pyridine

Histamine dihydrochloride (3.68 g; 20 mmol; 1 eq) and Paraformaldehyde (1.20 g; 40 mmol; 2 eq) were dissolved in water (30 ml). The mixture was heated to reflux for 4 hours. The volatiles were evaporated and the residue was dried under vacuum. The compound was used without further purification. Yield: quantitative; ESI-MS m/z: 124.1 [M+H]$^+$; HPLC (Gradient C): rt 1.25 min (100%), $^1$H-NMR, 400 MHz, DMSO d$_6$: δ 2.95-2.98, 3.42 (t, 2H, $^3$J=5.9 Hz), 4.28 (s, 2H), 9.02 (s, 1H), 10.13 (br s, 2H), 14.83 (br s, 1H);

Method B:

A suspension of 4,5,6,7-Tetrahydro-1H-imidazo[4,5-c]pyridine (0.196 g; 1 mmol; 1 eq) in acetonitrile (10 ml) was treated with triethylamine (416 μl; 3 mmol; 3 eq) and the mixture was at room temperature for 30 minutes. The respective halide, preferably an alkyl bromide (1 mmol; 1 eq) was added and the mixture was stirred at room temperature for further 12 hours. The volatiles were evaporated and the residue was taken up in water. The aqueous layer was extracted with EtOAc (3×20 ml). The combined organic layers were washed with brine, dried over Na$_2$SO$_4$ and evaporated. The product was purified by flash chromatography on silica using a CHC$_3$-MeOH gradient.

Examples

Methyl (E)-4-(3,4,6,7-tetrahydroimidazo[4,5-c]pyridin-5-yl)but-2-enoate (MWT-S-00138)

The compound was synthesized by method B as described above, starting from 4,5,6,7-Tetrahydro-1H-imidazo[4,5-c]pyridine (0.196 g) and Methyl 4-bromocrotonate (0.179 g). Yield: 62 mg (28%); ESI-MS: m/z 222.2 [M+H]$^+$; HPLC (gradient 1): 3.49 min (99.4%); $^1$H-NMR, 400 MHz, DMSO d$_6$: δ 2.56 (t, 2H, $^3$J=5.5 Hz), 2.70 (t, 2H, $^3$J=5.5 Hz), 3.34 (dd, 2H, $^3$J=5.8 Hz, $^4$J=1.8 Hz), 3.41 (s, 2H), 3.677 (s, 3H), 6.07 (td, 1H, $^3J$=15.8 Hz, $^4J$=1.8 Hz), 6.90 (td, 1H, $^3J$=15.7 Hz, $^3J$=5.9 Hz), 7.43 (s, 1H), 11.70 (s, 1H)

5-Benzyl-3,4,6,7-tetrahydroimidazo[4,5-c]pyridine (MWT-S-00139)

The compound was synthesized by method B as described above, starting from 4,5,6,7-Tetrahydro-1H-imidazo[4,5-c]pyridine (0.196 g) and phenethylbromide (137 µl). Yield: 82 mg (38%); ESI-MS: m/z 214.1 [M+H]$^+$; HPLC (gradient 1): 8.56 min (100%); $^1$H-NMR, 400 MHz, DMSO d$_6$: δ 2.56 (t, 2H, $^3J$=5.5 Hz), 2.71 (t, 2H, $^3J$=5.7 Hz), 3.34 (s, 2H), 3.67 (s, 2H), 7.24-7.30 (m, 1H), 7.33-7.36 (m, 4H), 7.40 (s, 1H), 11.65 (br s, 1H)

5-(2-Phenylethyl)-3,4,6,7-tetrahydroimidazo[4,5-c]pyridine (MWT-S-00145)

The compound was synthesized by method B as described above, starting from 4,5,6,7-Tetrahydro-1H-imidazo[4,5-c]pyridine (0.196 g) and benzylbromide (119 µl). Yield: 10 mg (4%); ESI-MS: m/z 228.2 [M+H]$^+$; HPLC (gradient 2): 5.41 min (100%); $^1$H-NMR, 400 MHz, DMSO d$_6$: δ 2.58 (t, 2H, $^3J$=5.7 Hz), 2.77-2.86 (m, 6H), 3.53 (s, 2H), 7.16-7.21 (m, 1H), 7.24-7.31 (m, 4H), 7.46 (s, 1H)

Method C:
A suspension of 4,5,6,7-Tetrahydro-1H-imidazo[4,5-c]pyridine (0.196 g; 1 mmol; 1 eq) in dimethoxyethane (10 ml) was treated with triethylamine (485 µl; 3.5 mmol; 3.5 eq) and the mixture was stirred at room temperature for 30 minutes. The solution was cooled to 0° C. and the respective acyl halide, preferably an acyl chloride (1 mmol; 1 eq) was added dropwise. After complete addition, the mixture was stirred at room temperature for 12 hours. The volatiles were evaporated and the residue was taken up in water. The aqueous layer was extracted with EtOAc (3×20 ml). The organic layer was washed with brine, dried over Na$_2$SO$_4$ and evaporated. The product was purified by flash chromatography on silica using a CHCl$_3$-MeOH gradient.

Examples

(E)-3-Phenyl-1-(3,4,6,7-tetrahydroimidazo[4,5-c]pyridin-5-yl)prop-2-en-1-one (MWT-S-00146)

The compound was synthesized by method C as described above, starting from 4,5,6,7-Tetrahydro-1H-imidazo[4,5-c]pyridine (0.196 g) and cinnamoyl chloride (167 mg). Yield: 17 mg (6.7%); ESI-MS: m/z 254.1 [M+H]$^+$; HPLC (gradient 2): 8.56 min (97.3%); $^1$H-NMR, 400 MHz, DMSO d$_6$: δ 2.68-2.72 (m, 2H), 3.92 (t, 2H, $^3J$=5.5 Hz), 4.62 (s, 2H), 7.22-7.30 (m, 1H), 7.37-7.44 (m, 3H), 7.47-7.54 (m, 2H), 7.67-7.75 (m, 2H), 11.67 (br s, 1H)

3-Phenyl-1-(3,4,6,7-tetrahydroimidazo[4,5-c]pyridin-5-yl)propan-1-one (MWT-S-00147)

The compound was synthesized by method C as described above, starting from 4,5,6,7-Tetrahydro-1H-imidazo[4,5-c]pyridine (0.196 g) and Phenylacetyl chloride (132 µl). Yield: 68 mg (26.6%); ESI-MS: m/z 256.1 [M+H]$^+$; HPLC (gradient 2): 7.65 min (94.5%); $^1$H-NMR, 400 MHz, DMSO d$_6$: δ 2.56-2.62 (m, 2H), 2.68-2.75 (m, 2H), 2.84-2.92 (m, 2H), 3.65-3.81 (m, 2H), 4.44 (s, 2H), 7.16-7.21 (m, 1H), 7.24-7.30 (m, 4H), 7.44 (s, 1H), 11.63 (br s, 1H)

2-Phenyl-1-(3,4,6,7-tetrahydroimidazo[4,5-c]pyridin-5-yl)ethanone (MWT-S-00148)

The compound was synthesized by method C as described above, starting from 4,5,6,7-Tetrahydro-1H-imidazo[4,5-c]pyridine (0.196 g) and hydrocinnamoyl chloride (148 µl). Yield: 23 mg (9.5%); ESI-MS: m/z 242.1 [M+H]$^+$; HPLC (gradient 2): 7.04 min (95.9%); $^1$H-NMR, 400 MHz, DMSO d$_6$: δ 3.71-3.86 (m, 4H), 4.48 (s, 2H), 7.18-7.35 (m, 5H), 7.44 (s, 1H), 11.64 (br s, 1H)

Phenyl(3,4,6,7-tetrahydroimidazo[4,5-c]pyridin-5-yl)methanone (MWT-S-00149)

The compound was synthesized by method C as described above, starting from 4,5,6,7-Tetrahydro-1H-imidazo[4,5-c]pyridine (0.196 g) and benzoylchloride (116 µl). Yield: 34 mg (15%); ESI-MS: m/z 228.1 [M+H]$^+$; HPLC (gradient 2): 6.11 min (100%); $^1$H-NMR, 400 MHz, DMSO d$_6$: δ 2.62-2.71 (m, 2H), 3.60-3.85 (m, 2H), 4.49 (s, 2H), 7.41-7.50 (m, 6H), 11.72 (br s, 1H)

(4-Fluorophenyl)-(3,4,6,7-tetrahydroimidazo[4,5-c]pyridin-5-yl)methanone (MWT-S-00156)

The compound was synthesized by method C as described above, starting from 4,5,6,7-Tetrahydro-1H-imidazo[4,5-c]pyridine (0.196 g) and 4-Fluorbenzoylchloride (118 µl). Yield: 43 mg (17.5%); ESI-MS: m/z 246.1 [M+H]$^+$; HPLC (gradient 2): 6.72 min (100%); $^1$H-NMR, 400 MHz, DMSO d$_6$: δ 2.57-2.72 (m, 2H), 3.43-3.70 (m, 1.4H), 3.76-3.99 (m, 0.6H), 4.25-4.66 (m, 2H), 7.25-7.32 (m, 2H), 7.45-7.57 (m, 3H), 11.91 (br s, 1H)

(4-Methoxyphenyl)-(3,4,6,7-tetrahydroimidazo[4,5-c]pyridin-5-yl)methanone (MWT-S-00157)

The compound was synthesized by method C as described above, starting from 4,5,6,7-Tetrahydro-1H-imidazo[4,5-c]pyridine (0.196 g) and 4-Methoxybenzoylchloride (135 µl) and was further purified by semi-preparative HPLC. Yield: 14 mg (3.8%); ESI-MS: m/z 258.1 [M+H]$^+$; HPLC (gradient 2): 6.88 min (100%); $^1$H-NMR, 400 MHz, DMSO d$_6$: δ 2.79 (t, 2H, $^3J$=5.5 Hz), 3.69-3.81 (m, 2H), 3.81 (s, 3H), 4.59-4.76 (m, 2H), 6.98-7.05 (m, 2H), 7.44-7.49 (m, 2H), 8.90 (s, 1H), 14.27 (br s, 1H)

(3-Methoxyphenyl)-(3,4,6,7-tetrahydroimidazo[4,5-c]pyridin-5-yl)methanone (MWT-S-00158)

The compound was synthesized by method C as described above, starting from 4,5,6,7-Tetrahydro-1H-imidazo[4,5-c]pyridine (0.196 g) and 3-Methoxybenzoylchloride (141 µl) and was further purified by semi-preparative HPLC. Yield: 19 mg (5%); ESI-MS: m/z 258.1 [M+H]$^+$; HPLC (gradient 2): 6.91 min (100%); $^1$H-NMR, 400 MHz, DMSO d$_6$: δ 2.69-2.83 (m, 2H), 3.61-3.68 (m, 1.4H), 3.79 (s, 3H), 3.85-4.01 (m, 0.6H), 4.42-4.81 (m, 2H), 6.99-7.04 (m, 2H), 7.07 (ddd, 1H, $^3J$=8.3, $^4J$=2.6, $^4J$=0.9), 7.4 (t, 1H, $^3J$=7.9), 8.75-8.96 (m, 1H), 14.22 (brs, 1H)

(3,4-Dichlorophenyl)-(3,4,6,7-tetrahydroimidazo[4,5-c]pyridin-5-yl)methanone (MWT-S-00159)

The compound was synthesized by method C as described above, starting from 4,5,6,7-Tetrahydro-1H-imidazo[4,5-c]pyridine (0.196 g) and 3,4-Dichlorobenzoylchloride (209 mg) and was further purified by semi-preparative HPLC. Yield: 57 mg (18.9%); ESI-MS: m/z 296.1 [M+H]$^+$; HPLC (gradient 2): 9.52 min (100%); $^1$H-NMR, 400 MHz, DMSO d$_6$: δ 2.71-2.84 (m, 2H), 3.56-3.70 (m, 1.4H), 3.84-3.99 (m, 0.6H), 4.44-4.79 (m, 2H), 7.44-7.50 (m, 1H), 7.71-7.80 (m, 2H), 8.74-8.94 (m, 1H), 14.12 (brs, 1H)

(4-Chlorophenyl)-(3,4,6,7-tetrahydroimidazo[4,5-c]pyridin-5-yl)methanone (MWT-S-00160)

The compound was synthesized by method C as described above, starting from 4,5,6,7-Tetrahydro-1H-imidazo[4,5-c]pyridine (0.196 g) and 4-Chlorobenzoylchloride (128 μl). Yield: 89 mg (34%); ESI-MS: m/z 262.1 [M+H]$^+$; HPLC (gradient 2): 8.03 min (96.4%); $^1$H-NMR, 400 MHz, DMSO d$_6$: δ 2.56-2.71 (m, 2H), 3.45-3.58 (m, 1H), 3.85-3.99 (m, 1H), 4.22-4.61 (m, 2H), 7.46-7.58 (m, 5H), 11.96 (brs, 1H)

(3-Chlorophenyl)(1,4,6,7-tetrahydro-5H-imidazo[4,5-c]pyridin-5-yl)methanone (MWT-S-00425)

ESI-MS: m/z 262.1 [M+H]$^+$; HPLC (gradient 2): 8.00 min (100%); $^1$H-NMR, 400 MHz, DMSO d$_6$: δ 2.59-2.73 (m, 2H), 3.49-3.59 (m, 1H), 3.87-3.97 (m, 1H), 4.29-4.39 (m, 1H), 4.58 (br s, 1H); 7.39-7.41 (m, 1H), 7.49-7.58 (m, 4H); 11.90 (br s, 1H)

(3,4-Dimethoxyphenyl)(1,4,6,7-tetrahydro-5H-imidazo[4,5-c]pyridin-5-yl)methanone (MWT-S-00426)

ESI-MS: m/z 288.1 [M+H]$^+$; HPLC (gradient 2): 5.89/6.37 min (100%; doublepeak); $^1$H-NMR, 400 MHz, DMSO d$_6$: δ 2.65-2.68 (m, 2H), 3.79-3.83 (m, 8H), 4.49 (br s, 2H); 7.01-7.03 (m, 3H), 7.53 (br s, 1H); 11.88 (br s, 1H)

Benzo[d][1,3]dioxol-5-yl(1,4,6,7-tetrahydro-5H-imidazo[4,5-c]pyridin-5-yl)methanone (MWT-S-00427)

ESI-MS: m/z 272.1 [M+H]$^+$; HPLC (gradient 2): 6.53 min (100%); $^1$H-NMR, 400 MHz, DMSO d$_6$: δ 2.65 (br s, 2H); 3.52-3.90 (m, 2H); 4.47 (br s, 2H); 6.09 (s, 2H); 6.94-7.01 (m, 3H); 7.51 (s, 1H); 11.88 (br s, 1H)

[1,1'-Biphenyl]-4-yl(1,4,6,7-tetrahydro-5H-imidazo[4,5-c]pyridin-5-yl)methanone (MWT-S-00428)

ESI-MS: m/z 304.1 [M+H]$^+$; HPLC (gradient 2): 10.61 min (100%); $^1$H-NMR, 400 MHz, DMSO d$_6$: δ 2.68 (s, 2H); 3.63 (br s; 1H); 3.94 (br s; 1H); 4.42-4.60 (m, 2H); 7.40-7.43 (m, 1H); 7.49-7.55 (m, 5H); 7.72-7.78 (m, 4H); 11.91 (br s, 1H)

(3,5-Dimethoxyphenyl)(1,4,6,7-tetrahydro-5H-imidazo[4,5-c]pyridin-5-yl)methanone (MWT-S-00429)

ESI-MS: m/z 288.1 [M+H]$^+$; HPLC (gradient 2): 7.71 min (92.9%); $^1$H-NMR, 400 MHz, DMSO d$_6$: 2.58-2.68 (m, 2H); 3.54 (br s, 1H); 3.78 (s, 6H); 3.90 (br s, 1H); 4.34 (br s, 1H); 4.56 (br s, 1H); 6.54 (s, 2H); 6.58-6.59 (m, 1H); 7.48-7.53 (m, 1H); 11.88 (br s; 1H)

(3-Fluorophenyl)(1,4,6,7-tetrahydro-5H-imidazo[4,5-c]pyridin-5-yl)methanone (MWT-S-00430)

ESI-MS: m/z 245.1 [M+H]$^+$; HPLC (gradient 2): 6.64 min (100%); $^1$H-NMR, 400 MHz, DMSO d$_6$: δ 2.59-2.73 (m, 2H); 3.53 (br s, 1H); 3.92 (br s, 1H); 4.33 (br s, 1H); 4.58 (s, 1H); 7.27-7.36 (m, 3H); 7.48-7.55 (m, 2H); 11.89 (br s, 1H)

(3,5-Dichlorophenyl)(1,4,6,7-tetrahydro-5H-imidazo[4,5-c]pyridin-5-yl)methanone (MWT-S-00431)

APCI-MS: m/z 295.9 [M+H]$^+$; HPLC (gradient 2): 9.23 min (98.3%); $^1$H-NMR, 400 MHz, DMSO d$_6$: δ 2.61-2.68 (m, 2H); 3.53 (br s, 1H); 3.91 (br s, 1H); 4.33 (s, 1H); 4.58 (s, 1H); 7.52-7.56 (m, 3H); 7.74-7.75 (m, 1H); 11.95 (br s, 1H)

(3-Propoxyphenyl)(1,4,6,7-tetrahydro-5H-imidazo[4,5-c]pyridin-5-yl)methanone (MWT-S-00432)

APCI-MS: m/z 286.1 [M+H]$^+$; HPLC (gradient 2): 9.23 min (86.6%); $^1$H-NMR, 400 MHz, DMSO d$_6$: δ 0.98 (t, 3H, $^3$J=7.3 Hz); 1.74 (sext, 2H, $^3$J=6.8 Hz); 2.60-2.71 (m, 2H); 3.54 (br s, 1H); 3.86-3.98 (m, 3H); 4.34 (br s, 1H); 4.57 (br s, 1H); 6.94-7.08 (m, 3H); 7.35-7.39 (m, 1H); 7.50-7.56 (m, 1H); 11.94 (br s, 1H)

[1,1'-Biphenyl]-3-yl(1,4,6,7-tetrahydro-5H-imidazo[4,5-c]pyridin-5-yl)methanone (MWT-S-00433)

APCI-MS: m/z 304.1 [M+H]$^+$; HPLC (gradient 2): 10.22 min (99.5%); $^1$H-NMR, 400 MHz, DMSO d$_6$: δ 2.60-2.76 (m, 2H); 3.61 (br s, 1H); 3.95 (br s, 1H); 4.41 (br s, 1H); 4.62 (s, 1H); 7.39-7.59 (m, 6H); 7.70-7.73 (m, 3H); 7.78-7.80 (m, 1H); 11.91 (brs, 1H)

(2,3-Dihydrobenzo[b][1,4]dioxin-6-yl)(1,4,6,7-tetrahydro-5H-imidazo-[4,5-c]pyridin-5-yl)methanone (MWT-S-00434)

APCI-MS: m/z 286.0 [M+H]$^+$; HPLC (gradient 2): 6.52 min (99.6%); $^1$H-NMR, 400 MHz, DMSO d$_6$: δ 2.63-2.66 (m, 2H); 3.58-3.91 (m, 2H); 4.28-4.30 (m, 4H); 4.47 (br s; 2H); 6.92-6.94 (m, 3H); 7.51 (s, 1H); 11.87 (br s, 1H)

(1,4,6,7-Tetrahydro-5H-imidazo[4,5-c]pyridin-5-yl)(3,4,5-trifluoro-phenyl)methanone (MWT-S-00435)

APCI-MS: m/z 282.0 [M+H]$^+$; HPLC (gradient 2): 7.65 min (96.9%); $^1$H-NMR, 400 MHz, DMSO d$_6$: δ 2.66 (br s, 2H); 3.49-3.59 (m, 1H); 3.89 (br s, 1H); 4.36 (s, 1H); 4.57 (s, 1H); 7.45-7.57 (m, 3H); 11.96 (br s, 1H)

(4-Fluoro-3-methoxyphenyl)(1,4,6,7-tetrahydro-5H-imidazo[4,5-c]pyridin-5-yl)methanone (MWT-S-00436)

APCI-MS: m/z 276.0 [M+H]$^+$; HPLC (gradient 2): 7.10 min (99.7%); $^1$H-NMR, 400 MHz, DMSO d$_6$: δ 2.63-2.72 (m, 2H); 3.57 (br s, 1H); 3.88-3.95 (m, 4H); 4.38 (br s, 1H); 4.56 (br s, 1H); 7.00-7.04 (m, 1H); 7.23 (dd, 2H, $^4$J=1.5 Hz, $^3$J=8.3 Hz); 7.27-7.32 (m, 1H); 7.50-7.58 (m, 1H); 11.89 (br s; 1H)

Naphthalen-2-yl(1,4,6,7-tetrahydro-5H-imidazo[4,5-c]pyridin-5-yl)methanone (MWT-S-00440)

ESI-MS: m/z 278.1 [M+H]$^+$; HPLC (gradient 2): 9.20 min (100%); $^1$H-NMR, 400 MHz, DMSO d$_6$: δ 2.70 (brs, 2H); 3.61 (brs, 1H); 3.98 (brs, 1H); 4.43 (brs, 1H); 4.63 (brs, 1H); 7.44-7.64 (m, 4H); 7.98-8.04 (m, 4H); 11.89 (br s, 1H)

(3-Chloro-5-methoxyphenyl)(1,4,6,7-tetrahydro-5H-imidazo[4,5-c]pyridin-5-yl)methanone (MWT-S-00441)

APCI-MS: m/z 292.1 [M+H]$^+$; HPLC (gradient 2): 8.80 min (100%); $^1$H-NMR, 400 MHz, DMSO d$_6$: δ 2.62-2.71 (m, 2H); 3.53 (br s, 1H); 3.82 (s, 3H); 3.90 (br s, 1H); 4.32 (br s, 1H); 4.57 (br s, 1H); 6.95 (br s, 1H); 7.05 (s, 1H); 7.14 (s, 1H); 7.49-7.54 (m, 1H); 11.87 (br s, 1H)

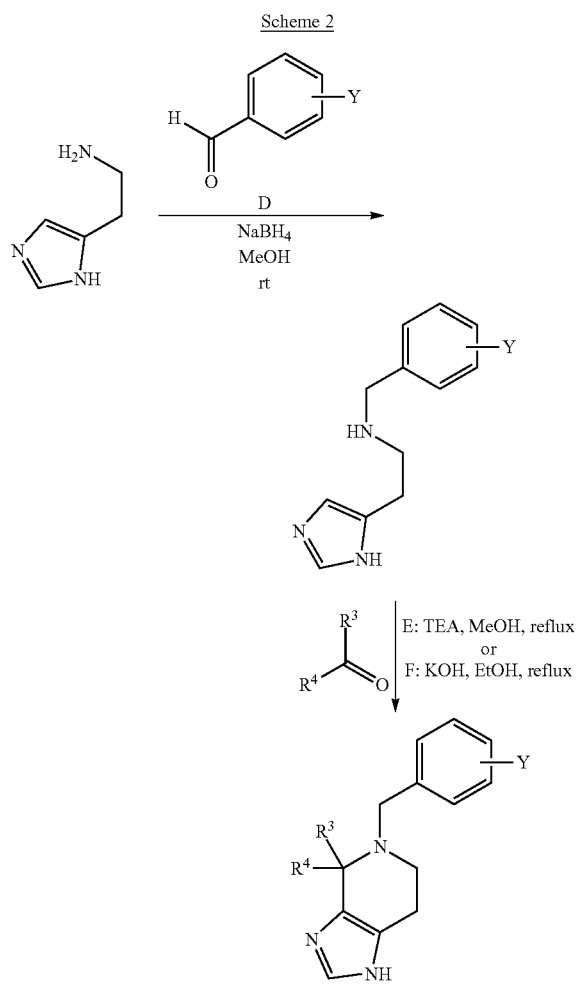

Scheme 2

Method D:

Histamine (1 eq) was dissolved in methanol (30 ml). The respective aldehyde (1 eq) was added and the mixture was stirred at room temperature for 3 hours. Sodium borohydride (1.5 eq) was added in portions and the reaction was stirred at room temperature for further 3 hours. The volatiles were evaporated and the residue was taken up in water. The aqueous layer was extracted with EtOAc (3×50 ml). The combined organic layers were dried over Na$_2$SO$_4$ and evaporated. The product was used without further purification. If necessary, the product was purified by flash chromatography on silica using a CHCl$_3$-MeOH gradient.

Method E:

The N-Benzylhistamine derivative obtained by method D (1 mmol; 1 eq) was dissolved in methanol or ethanol (0.3-0.5 M). The respective aldehyde (1.2 mmol; 1.2 eq) and trimethylamine (1 mmol; 1 eq) were added and the mixture was heated to reflux overnight. The volatiles were evaporated and the residue was taken up in water and a small amount of saturated aqueous NaHCO$_3$. The aqueous layer was extracted with EtOAc (3×20 ml). The combined organic layers were washed with brine, dried over Na$_2$SO$_4$ and evaporated. The product was purified by flash chromatography on silica using a CHCl$_3$-MeOH gradient.

Method F:

The N-Benzylhistamine derivative obtained by method D (1 eq) was dissolved in ethanol (2 ml). Paraformaldehyde (2 eq) and potassium hydroxide (1 eq) were added and the mixture was heated in a microwave (100° C., 5 min). The volatiles were evaporated and the residue was taken up in water and a small amount of saturated aqueous NaHCO$_3$. The aqueous layer was extracted with EtOAc (3×20 ml). The combined organic layers were washed with brine, dried over Na$_2$SO$_4$ and evaporated. The product purified by flash chromatography on silica using a CHCl$_3$-MeOH gradient.

Examples

5-Benzylspiro[6,7-dihydro-3H-imidazo[4,5-c]pyridine-4,3'-oxetane] (MWT-S-00260)

The compound was synthesized by methods D & E as described above, starting from Histamine (1111 mg; 10 mmol; 1 eq), benzaldehyde (1.02 ml; 10 mmol; 1 eq), NaBH$_4$ (568 mg; 15 mmol; 1.5 eq); oxetan-3-one (59 μl; 1 mmol; 1 eq) and triethylamine (139 μl; 1 mmol; 1 eq) for the second step. Yield (second step): 133 mg (52%); ESI-MS: m/z 256.2 [M+H]$^+$; HPLC (gradient 2): 7.93 min (97.2%); $^1$H-NMR, 400 MHz, DMSO d$_6$: δ 2.46 (t, 2H, $^3$J=5.0 Hz), 2.67 (t, 2H, $^3$J=5.7 Hz), 3.89 (s, 2H), 4.74-4.86 (m, 4H), 7.24-7.29 (m, 1H), 7.33-7.38 (m, 2H), 7.42-7.47 (m, 2H), 7.56 (s, 1H), 11.84 (br s, 1H)

4-Phenyl-5-[(3,4,5-trifluorophenyl)methyl]-3,4,6,7-tetrahydroimidazo[4,5-c]pyridine (MWT-S-00261)

The compound was synthesized by methods D & E as described above, starting from Histamine (1111 mg; 10 mmol; 1 eq), 3,4,5-Trifluorobenzaldehyde (1.6 g; 10 mmol; 1 eq), NaBH$_4$ (568 mg; 15 mmol; 1.5 eq); benzaldehyde (122 μl; 1.2 mmol; 1.2 eq) and triethylamine (139 μl; 1 mmol; 1 eq) for the second step. Yield (second step): 150 mg (43.7%); ESI-MS: m/z 344.3 [M+H]$^+$; HPLC (gradient 2): 12.71 min (98.3%); $^1$H-NMR, 400 MHz, DMSO d$_6$: δ 2.58-2.68 (m, 3H), 2.86-2.93 (m, 1H), 3.52 (d, 1H, J=14.5 Hz), 3.61 (d, 1H, J=14.5 Hz), 4.58 (s, 1H), 7.22-7.29 (m, 3H), 7.31-7.34 (m, 4H), 7.54 (s, 1H), 12.09 (br s, 1H)

5-Benzyl-4-methyl-3,4,6,7-tetrahydroimidazo[4,5-c]pyridine (MWT-S-00265)

The compound was synthesized by methods D & E as described above, starting from Histamine (1111 mg; 10 mmol; 1 eq), 3,4,5-Trifluorobenzaldehyde (1.6 g; 10 mmol; 1 eq), NaBH$_4$ (568 mg; 15 mmol; 1.5 eq); acetaldehyde (112 μl; 2 mmol; 2 eq) and triethylamine (139 μl; 1 mmol; 1 eq) for the second step. The reaction was carried out in a sealed vessel. Yield (second step): 60 mg (26.4%); ESI-MS: m/z 228.2 [M+H]$^+$; HPLC (gradient 2): 3.79 min (95.3%); $^1$H-NMR, 400 MHz, DMSO d$_6$: δ 1.29 (d, 3H, $^3$J=6.1 Hz), 2.35-2.48 (m, 2H), 2.53-2.61 (m, 1H), 2.83-2.96 (m, 1H),

5-[(3,4,5-Trifluorophenyl)methyl]spiro[6,7-dihydro-3H-imidazo[4,5-c]pyridine-4,3'-oxetane](MWT-S-00266)

The compound was synthesized by methods D & E as described above, starting from Histamine (1111 mg; 10 mmol; 1 eq), 3,4,5-Trifluorobenzaldehyde (1.6 g; 10 mmol; 1 eq), NaBH$_4$ (568 mg; 15 mmol; 1.5 eq); oxetanone (70 µl; 1.2 mmol; 1.2 eq) and triethylamine (139 µl; 1 mmol; 1 eq) for the second step. Yield (second step): 236 mg (76.3%); ESI-MS: m/z 310.3 [M+H]$^+$; HPLC (gradient 2): 10.66 min (100%); $^1$H-NMR, 400 MHz, DMSO d$_6$: δ 2.68 (t, 2H, J=5.7 Hz), 3.90 (s, 2H), 4.68-4.72 (m, 2H), 4.79-4.84 (m, 2H), 7.36-7.42 (m, 2H), 7.56 (s, 1H), 11.86 (br s, 1H)

4-Methyl-5-[(3,4,5-trifluorophenyl)methyl]-3,4,6,7-tetrahydro-imidazo[4,5-c]pyridine (MWT-S-00267)

The compound was synthesized by methods D & E as described above, starting from Histamine (1111 mg; 10 mmol; 1 eq), 3,4,5-Trifluorobenzaldehyde (1.6 g; 10 mmol; 1 eq), NaBH$_4$ (568 mg; 15 mmol; 1.5 eq); acetaldehyde (112 µl; 2 mmol; 2 eq) and triethylamine (139 µl; 1 mmol; 1 eq) for the second step. Yield (second step): 227 mg (80.7%); ESI-MS: m/z 282.2 [M+H]$^+$; HPLC (gradient 2): 6.95 min (98.5%); $^1$H-NMR, 400 MHz, DMSO d$_6$: δ 1.28 (d, 3H, J=6.6 Hz), 2.41-2.49 (m, 1H), 2.52-2.63 (m, 2H), 2.88-2.96 (m, 1H), 3.54-3.60 (m, 2H), 3.81 (d, 1H, J=14.9 Hz), 7.27-7.34 (m, 2H), 7.44 (s, 1H), 11.71 (br s, 1H)

5-Benzyl-4-phenyl-3,4,6,7-tetrahydroimidazo[4,5-c]pyridine (MWT-S-268)

The compound was synthesized by methods D & E as described above, starting from Histamine (1111 mg; 10 mmol; 1 eq), benzaldehyde (1.02 ml; 10 mmol; 1 eq), NaBH$_4$ (568 mg; 15 mmol; 1.5 eq); benzaldehyde (122 µl; 1.2 mmol; 1.2 eq) and triethylamine (139 µl; 1 mmol; 1 eq) for the second step. Yield (second step): 194 mg (67%); ESI-MS: m/z 290.1 [M+H]$^+$; HPLC (gradient 2): 9.68 min (100%); $^1$H-NMR, 400 MHz, DMSO d$_6$: δ 2.54-2.63 (m, 3H), 2.89-2.96 (m, 1H), 3.43 (d, 1H, J=13.6 Hz), 3.66 (d, 1H, J=13.6 Hz), 4.51 (s, 1H), 7.21-7.26 (m, 2H), 7.30-7.34 (m, 8H), 7.39 (s, 1H), 11.65 (br s, 1H)

4,4-Dimethyl-5-[(3,4,5-trifluorophenyl)methyl]-6,7-dihydro-3H-imidazo[4,5-c]pyridine (MWT-S-00275)

The compound was synthesized by methods D & E as described above, starting from Histamine (1111 mg; 10 mmol; 1 eq), 3,4,5-Trifluorobenzaldehyde (1.6 g; 10 mmol; 1 eq), NaBH$_4$ (568 mg; 15 mmol; 1.5 eq); acetone (735 µl; 10 mmol; 10 eq) and triethylamine (139 µl; 1 mmol; 1 eq) for the second step. Yield (second step): 88 mg (29.8%); ESI-MS: m/z 296.3 [M+H]$^+$; HPLC (gradient 2): 7.89 min (100%); $^1$H-NMR, 400 MHz, DMSO d$_6$: δ 1.32 (s, 6H), 2.43 (t, 2H, $^3$J=5.5 Hz), 2.62 (t, 2H, $^3$J=5.7 Hz), 3.64 (s, 2H), 7.27-7.35 (m, 2H), 7.42 (s, 1H), 11.69 (br s, 1H)

5-[[4-(1-Piperidyl)phenyl]methyl]-1,4,6,7-tetrahydroimidazo[4,5-c]pyridine (MWT-S-00320)

The compound was synthesized by methods D & F as described above, starting from Histamine (222 mg; 2 mmol; 1 eq), 4-(1-Piperidinyl)benzaldehyde (379 mg; 2 mmol; 1 eq), NaBH$_4$ (114 mg; 3 mmol; 1.5 eq); paraformaldehyde (76 mg; 2.5 mmol; 2 eq) and potassium hydroxide (71 mg; 1.3 mmol; 1 eq) for the second step. Yield (second step): 130 mg (34.9%); ESI-MS: m/z 297.5 [M+H]$^+$; HPLC (gradient 2): 1.44/3.6 min (100%); $^1$H-NMR, 400 MHz, DMSO d$_6$: δ 1.48-1.57 (m, 2H), 1.57-1.65 (m, 4H), 2.52-2.57 (m, 2H), 2-65-2.71 (m, 2H), 3.05-3.13 (m, 4H), 3.28-3.32 (m, 2H), 3.55 (s, 2H), 6.85-6.90 (m, 2H), 7.12-7.18 (m, 2H), 7.39 (s, 1H), 11.63 (br s, 1H)

4-[2-[4-(1,4,6,7-Tetrahydroimidazo[4,5-c]pyridin-5-ylmethyl)phenoxy]ethyl]morpholine (MWT-S-00330)

The compound was synthesized by methods D & F as described above, starting from Histamine (222 mg; 2 mmol; 1 eq), 4-(2-Morpholinoethoxy)benzaldehyde (471 mg; 2 mmol; 1 eq), NaBH$_4$ (114 mg; 3 mmol; 1.5 eq); paraformaldehyde (24 mg; 0.8 mmol; 2 eq) and potassium hydroxide (22 mg; 0.4 mmol; 1 eq) for the second step. Yield (second step): 21 mg (15.5%); ESI-MS: m/z 343.4 [M+H]$^+$; HPLC (gradient 1): 1.18 min (77%); $^1$H-NMR, 400 MHz, DMSO d$_6$: δ 2.43-2.49 (m, 4H), 2.65-2.71 (m, 4H), 3.55-3.60 (m, 6H), 4.03-4.09 (m, 2H), 6.88-6.92 (m, 2H), 7.22-7.26 (m, 2H), 7.40 (s, 1H), 11.65 (br s, 1H)

5-[(4-Butoxyphenyl)methyl]-1,4,6,7-tetrahydroimidazo[4,5-c]pyridine (MWT-S-00331)

The compound was synthesized by methods D & F as described above, starting from Histamine (222 mg; 2 mmol; 1 eq), 4-Butoxybenzaldehyde (357 mg; 2 mmol; 1 eq), NaBH$_4$ (114 mg; 3 mmol; 1.5 eq); paraformaldehyde (54 mg; 1.8 mmol; 2 eq) and potassium hydroxide (50 mg; 0.9 mmol; 1 eq) for the second step. Yield (second step): 170 mg (67.3%); ESI-MS: m/z 286.3 [M+H]$^+$; HPLC (gradient 2): 8.88 min (100%); $^1$H-NMR, 400 MHz, DMSO d$_6$: δ 0.95 (t, 3H, $^3$J=7.4 Hz), 1.40-1.50 (m, 2H), 1.67-1.75 (m, 2H), 2.91-2.97 (m, 2H), 3.40-3.48 (m, 2H), 4.00 (t, 2H, $^3$J=6.5 Hz), 4.13-4.18 (m, 2H), 4.31-4.36 (m, 2H), 7.00-7.05 (m, 2H), 7.40-7.45 (m, 2H), 8.66 (s, 1H)

5-[(3-Methoxyphenyl)methyl]-1,4,6,7-tetrahydroimidazo[4,5-c]pyridine (MWT-S-00343)

The compound was synthesized by methods D & F as described above, starting from Histamine (222 mg; 2 mmol; 1 eq), 3-Methoxy-benzaldehyde (272 mg; 2 mmol; 1 eq), NaBH$_4$ (114 mg; 3 mmol; 1.5 eq); paraformaldehyde (69 mg; 2.3 mmol; 2 eq) and potassium hydroxide (64 mg; 1.1 mmol; 1 eq) for the second step. Yield (second step): 42 mg (15.1%); ESI-MS: m/z 244.3 [M+H]$^+$; HPLC (gradient 2): 4.89 min (97.6%); $^1$H-NMR, 400 MHz, DMSO d$_6$: δ 2.53-2.58 (m, 2H), 2.67-2.72 (m, 2H), 3.65 (s, 2H), 3.75 (s, 3H), 6.81-6.86 (m, 1H), 6.90-6.94 (m, 2H), 7.22-7.28 (m, 1H), 7.41 (s, 1H), 11.64 (br s, 1H)

5-[(2,2-Difluoro-1,3-benzodioxol-5-yl)methyl]-1,4,6,7-tetrahydro-imidazo[4,5-c]pyridine (MWT-S-00344)

The compound was synthesized by methods D & F as described above, starting from Histamine (222 mg; 2 mmol; 1 eq), 2,2-Difluoro-1,3-benzodioxole-5-carboxaldehyde (372 mg; 2 mmol; 1 eq), NaBH$_4$ (114 mg; 3 mmol; 1.5 eq); paraformaldehyde (49 mg; 1.6 mmol; 2 eq) and potassium Starting text of page 53: 3.49-3.59 (m, 3H), 3.85 (d, 1H, J=13.2 Hz), 7.22-7.27 (m, 1H), 7.29-7.38 (m, 4H), 7.42 (s, 1H), 11.66 (br s, 1H)

hydroxide (46 mg; 0.8 mmol; 1 eq) for the second step. Yield (second step): 53 mg (22.0%); ESI-MS: m/z 294.2 [M+H]$^+$; HPLC (gradient 2): 7.94 min (100%); $^1$H-NMR, 400 MHz, DMSO d$_6$: δ 2.53-2.59 (m, 2H), 2.7 (t, 2H, J=5.7 Hz), 3.35-3.38 (m, 2H), 3.69 (s, 2H), 7.19 (dd, 1H, $^4$J=1.3 Hz, $^3$J=8.3 Hz), 7.35 (d, 1H, $^3$J=8.3 Hz), 7.38 (d, 1H, $^4$J=1.3 Hz), 7.42 (s, 1H), 11.68 (br s, 1H)

5-[(4-Benzyloxyphenyl)methyl]-1,4,6,7-tetrahydro-imidazo[4,5-c]pyridine (MWT-S-00359)

The compound was synthesized by methods D & F as described above, starting from Histamine (222 mg; 2 mmol; 1 eq), 4-Benzyloxy-benzaldehyde (425 mg; 2 mmol; 1 eq), NaBH$_4$ (114 mg; 3 mmol; 1.5 eq); paraformaldehyde (57 mg; 1.9 mmol; 2 eq) and potassium hydroxide (53 mg; 0.94 mmol; 1 eq) for the second step. Yield (second step): 61 mg (20.2%); ESI-MS: m/z 320.2 [M+H]$^+$; HPLC (gradient 2): 9.37 min (100%); $^1$H-NMR, 400 MHz, DMSO d$_6$: δ 2.53-2.57 (m, 2H), 2.69-2.72 (m, 2H), 3.6 (s, 2H), 5.09 (s, 2H), 6.96-7.01 (m, 2H), 7.23-7.29 (m, 2H), 7.31-7.48 (m, 6H)

5-[(3-Pyrrolidin-1-ylphenyl)methyl]-1,4,6,7-tetrahydroimidazo[4,5-c]pyridine (MWT-S-00361)

The compound was synthesized by methods D & F as described above, starting from Histamine (222 mg; 2 mmol; 1 eq), 3-Pyrrolidin-1-ylbenzaldehyde (351 mg; 2 mmol; 1 eq), NaBH$_4$ (114 mg; 3 mmol; 1.5 eq); paraformaldehyde (37 mg; 1.2 mmol; 2 eq) and potassium hydroxide (35 mg; 0.61 mmol; 1 eq) for the second step. Yield (second step): 39 mg (22.4%); ESI-MS: m/z 283.4 [M+H]$^+$; HPLC (gradient 2): 7.15 min (96.5%); $^1$H-NMR, 400 MHz, DMSO d$_6$: δ 1.93-1.97 (m, 4H), 2.53-2.58 (m, 2H), 2.69-2.74 (m, 2H), 3.19-3.23 (m, 4H), 3.60 (s, 2H), 6.42-6.46 (m, 1H), 6.51-6.59 (m, 2H), 7.08-7.14 (m, 1H), 7.43 (s, 1H)

5-(2,3-Dihydro-1,4-benzodioxin-6-ylmethyl)-1,4,6,7-tetrahydro-imidazo[4,5-c]pyridine (MWT-S-00380)

The compound was synthesized by methods D & F as described above, starting from Histamine (222 mg; 2 mmol; 1 eq), 1,4-Benzodioxane-6-carboxaldehyde (328 mg; 2 mmol; 1 eq), NaBH$_4$ (114 mg; 3 mmol; 1.5 eq); paraformaldehyde (66 mg; 2.2 mmol; 2 eq) and potassium hydroxide (62 mg; 1.1 mmol; 1 eq) for the second step. The product was further purified by semi-preparative HPLC. Yield (second step): 72 mg (13.1%); ESI-MS: m/z 272.2 [M+H]$^+$; HPLC (gradient 2): 3.74 min (100%); $^1$H-NMR, 400 MHz, DMSO d$_6$: δ 2.88-2.95 (m, 2H), 4.11 (br s, 2H), 4.24 (br s, 2H), 4.27 (s, 4H), 6.92-6.98 (m, 2H), 7.04 (s, 1H), 8.62 (br s, 1H)

5-(p-Tolylmethyl)-1,4,6,7-tetrahydroimidazo[4,5-c]pyridine (MWT-S-00420)

The compound was synthesized by methods D & F as described above, starting from Histamine (222 mg; 2 mmol; 1 eq), p-Tolylaldehyde (240 mg; 2 mmol; 1 eq), NaBH$_4$ (114 mg; 3 mmol; 1.5 eq); paraformaldehyde (34 mg; 1.1 mmol; 2 eq) and potassium hydroxide (32 mg; 0.6 mmol; 1 eq) for the second step. Yield (second step): 10 mg (7.7%); ESI-MS: m/z 228.2 [M+H]$^+$; HPLC (gradient 2): 5.61 min (98.1%); $^1$H-NMR, 400 MHz, DMSO d$_6$: δ 2.34 (s, 3H), 2.89-2.94 (m, 2H), 3.35-3.44 (m, 2H), 4.08-4.13 (m, 2H), 4.27-4.33 (m, 2H), 7.26-7.3 (m, 2H), 7.37-7.41 (m, 2H), 8.66 (s, 1H)

5-[(4-Chlorophenyl)methyl]-1,4,6,7-tetrahydroimidazo[4,5-c]pyridine (MWT-S-00421)

The compound was synthesized by methods D & F as described above, starting from Histamine (222 mg; 2 mmol; 1 eq), 4-Chlorobenzaldehyde (281 mg; 2 mmol; 1 eq), NaBH$_4$ (114 mg; 3 mmol; 1.5 eq); paraformaldehyde (74 mg; 2.5 mmol; 2 eq) and potassium hydroxide (69 mg; 1.2 mmol; 1 eq) for the second step. Yield (second step): 38 mg (12.5%); ESI-MS: m/z 248.1 [M+H]$^+$; HPLC (gradient 2): 6.28 min (94.4%); $^1$H-NMR, 400 MHz, DMSO d$_6$: δ 2.82-2.89 (m, 2H), 3.18-3.28 (m, 2H), 3.90-3.96 (m, 2H), 4.12-4.20 (m, 2H), 7.47-7.54 (m, 4H), 8.73 (s, 1H)

5-[(3,4-Dichlorophenyl)methyl]-1,4,6,7-tetrahydro-imidazo[4,5-c]pyridine (MWT-S-00423)

The compound was synthesized by methods D & F as described above, starting from Histamine (222 mg; 2 mmol; 1 eq), 3,4-Dichloro-benzaldehyde (350 mg; 2 mmol; 1 eq), NaBH$_4$ (114 mg; 3 mmol; 1.5 eq); paraformaldehyde (58 mg; 1.9 mmol; 2 eq) and potassium hydroxide (54 mg; 1 mmol; 1 eq) for the second step. Yield (second step): 50 mg (18.3%); ESI-MS: m/z 282.0 [M+H]$^+$; HPLC (gradient 2): 7.47 min (100%); $^1$H-NMR, 400 MHz, DMSO d$_6$: δ 2.78-2.84 (m, 2H), 3.08-3.15 (m, 2H), 3.83-3.87 (m, 2H), 4.03-4.1 (m, 2H), 7.44 (dd, 1H, $^3$J=8.3 Hz, $^4$J=2.0 Hz), 7.67-7.74 (m, 2H), 8.79 (s, 1H)

Analytical Methods

HPLC: The analytical HPLC-system consisted of a Merck-Hitachi device (model LaChrom) utilizing a LUNA RP 18 (5 μm), analytical column (length: 125 mm, diameter: 4 mm), and a diode array detector (DAD) with λ=214 nm as the reporting wavelength. The compounds were analyzed using a gradient at a flow rate of 1 mL/min; whereby eluent (A) was acetonitrile, eluent (B) was water, both containing 0.04% (v/v) trifluoroacetic acid applying one of the following gradients:

Gradient 1: 0 min-5 min->5% (A), 5 min-17 min->5-15% (A), 17 min-27 min 15-95% (A) 27 min-30 min 95% (A)

Gradient 2: 0 min-5 min->5% (A), 5 min-15 min->5-60% (A), 15 min-20 min 60-95% (A) 20 min-30 min 95% (A)

The purities of all reported compounds were determined by the percentage of the peak area at 214 nm.

Mass-Spectrometry:

ESI-& APCI-Mass spectra were obtained with a SCIEX API 1200 spectrometer (Perkin Elmer) or an expression CMS (Advion).

Nmr-Spectroscopy:

The 1H NMR-Spectra were recorded at an Agilent DD2 400-MHz spectrometer. Chemical shifts are expressed as parts per million (ppm) downfield from tetramethylsilane. Splitting patterns have been designated as follows: s (singlet), d (doublet), dd (doublet of doublet), t (triplet), m (multiplet) and br (broad signal).

Example 11: Targeting of PgQC, TfQC and PiQC Expressing Bacteria

Bacteria expressing PgQC, TfQC and PiQC, namely *P. gingivalis* ATCC 33277, *P. gingivalis* M5-1-2, *T. forsythia* ATCC 42077, and *P. intermedia* ATCC 25611 were cultivated in the presence of compounds MWT-S-00275, MWT-S-00431, MWT-S-00441 and doxycycline in 2-fold dilution series. In the following Table 6, MIC denotes the lowest compound concentration without visible growth (turbidity), and MBC denotes the compound concentration at which no growth of subcultivation or at least reduction by 99.9% (three log$_{10}$ units) is observed.

TABLE 6

MIC and MBC inhibitory concentrations for compounds
MWT-S-00275, MWT-S-00431, MWT-S-00441 compared to doxycyclin.

| Compound | P.g. ATCC 33277 | | P.g. M5-1-2 | | T.f. ATCC 42077 | | P.i. ATCC 25611 | |
|---|---|---|---|---|---|---|---|---|
| | MIC | MBC | MIC | MBC | MIC | MBC | MIC | MBC |
| MWT-S-00275 (mg/ml) | 0.5 | 1 | 0.5 | 1 | 0.25 | 0.25 | 0.5 | 0.5 |
| MWT-S-00431 (mg/ml) | 1 | 2 | 1 | 2 | 1 | 2 | 0.125 | 0.5 |
| MWT-S-00441 (mg/ml) | 1 | 2 | 1 | >2 | 2 | 2 | 0.063 | 0.063 |
| Doxy (mg/ml) | ≤3.13 | 50 | ≤3.13 | 200 | ≤3.13 | 6.25 | ≤3.13 | 12.5 |

P.g. = *Porphyromonas gingivalis*,
T.f. = *Tannerella forsythia*,
P.i. = *Prevotella intermedia*;
Doxy = Doxycycline (broad-spectrum antibiotic).

The results in Table 6 show that compounds MWT-S-00275, MWT-S-00431, MWT-S-00441 are capable of inhibiting the growth or killing bacteria expressing PgQC, TfQC and PiQC already at significantly lower concentrations compared to the broad-spectrum antibiotic doxycycline, which is currently being used as standard adjuvant antibiotic periodontitis therapy.

Conclusions:

compounds according to the present invention are capable of targeting pathogens which induce a periodontal disease at much lower concentration than a non-specific, broad-spectrum antibiotic.

INDUSTRIAL APPLICABILITY

The bacterial glutaminyl cyclases (bacQC) according to the present invention represent therapeutic target proteins which can be specifically and substantially used for identifying inhibitors capable of selective targeting of periodontitis-inducing pathogen. Thus, they are relevant to the treatment of a particular disease, e.g. periodontitis, and, accordingly, susceptible to industrial applicability.

The antibodies according to the present invention recognize bacQC enzymes. The presence of bacQC-expressing bacteria is associated with the occurrence of periodontitis and inhibition of a bacQC can be used in the treatment of periodontitis, on the other. The antibodies according to the present invention can therefore be used in the treatment and/or diagnosis of a particular disease, and are therefore susceptible to industrial applicability.

The method for identifying an inhibitor of the bacQC according to the present is industrially applicable in view of the pharmaceutical relevance of the bacQC enzymes to the occurrence of periodontitis and their essentiality for the growth of periodontal pathogens demonstrated herein.

The bacQC inhibitors according to the present invention, including inhibitors identified by the method for identifying an inhibitor of the bacQC according to the present invention, and the pharmaceutical composition according to the present invention are also susceptible to industrial applicability, because these can be used in methods for treatment of the human or animal body, in particular in a method for therapy or prophylaxis of a bacterial infection, e.g. a bacterial infection caused by a bacterium selected from the group consisting of *Porphyromonas gingivalis*, *Prevotella intermedia* and *Tannerella forsythia*, and/or in a method for therapy or prophylaxis of an acute, chronic or recurrent periodontal disease, e.g. periodontitis.

The invention claimed is:

1. A method for therapy and/or prophylaxis of:

(i) a bacterial infection caused by:

a bacterium that expresses a bacterial glutaminyl cyclase (bacQC), wherein the bacQC is a polypeptide comprising an amino acid sequence selected from the group consisting of SEQ ID NO: 1, SEQ ID NO: 2, SEQ ID NO: 3, and an amino acid sequence having a sequence identity of 80% or more to any one of SEQ ID NO: 1, SEQ ID NO: 2 and SEQ ID NO: 3, a bacterium selected from the group consisting of *Porphyromonas gingivalis*, *Prevotella intermedia* and *Tannerella forsythia*, or a bacterium selected from the group consisting of *Porphyromonas gingivalis*, *Prevotella intermedia* and *Tannerella forsythia*, wherein the growth of said bacterium within a biofilm is selectively inhibited;

or (ii) an acute, chronic or recurrent periodontal disease;

wherein the method comprises administration of a therapeutically effective amount of a compound according to the following Formula I:

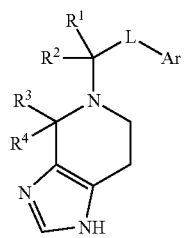

Formula I or an enantiomer, a diastereoisomer, a hydrate, a solvate, a crystal form, a tautomer, or a pharmaceutically acceptable salt thereof, wherein:

Ar is selected from the group consisting of optionally substituted aryl and optionally substituted heteroaryl;

wherein L is selected from the group consisting of single bond, $-CR^5(R^6)-$, $-CR^5(R^6)-CR^7(R^8)-$ and $-C(R^5)=C(R^6)-$;

wherein $R^1$, $R^2$, $R^5$, $R^6$, $R^7$ and $R^8$ are the same or different from each other and are independently selected from the group consisting of H, F, Cl, Br, I, OH, optionally substituted alkyl, optionally substituted aryl, optionally substituted heteroalkyl and optionally substituted heteroaryl;

$R^3$ and $R^4$ are the same or different from each other and are independently selected from the group consisting of H, F, Cl, Br, I, OH, optionally substituted alkyl, and optionally substituted heteroalkyl;

wherein within each pair of groups $R^1/R^2$, $R^3/R^4$, $R^5/R^6$ and $R^7/R^8$, the two groups can be optionally joined together to form a carbocyclic or a heterocyclic ring, or can optionally represent =O;

or a pharmaceutical composition comprising said compound, or an enantiomer, a diastereoisomer, a hydrate, a solvate, a crystal form, a tautomer, or a pharmaceutically acceptable salt thereof, and a pharmaceutically acceptable excipient;

to a subject in need thereof.

2. The method according to claim 1, wherein the acute, chronic or recurrent periodontal disease is selected from the group consisting of: dental plaque-induced gingival diseases, chronic periodontitis, aggressive periodontitis, periodontitis as a manifestation of systemic diseases, necrotizing periodontal diseases, abscesses of the periodontium, periodontitis associated with endodontic lesions, peri-implant mucositis, peri-implantitis and endodontic infections.

3. The method according to claim 1, wherein the route of administration is topical administration or systemic administration, and/or the method is a nonsurgical method.

4. The method according to claim 2, wherein the route of administration is topical administration or systemic administration, and/or the method is a nonsurgical method.

5. A method for therapy and/or prophylaxis of a bacterial infection, wherein the method comprises administration of a therapeutically effective amount of a compound according to the following Formula I:

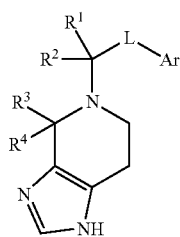

Formula I or an enantiomer, a diastereoisomer, a hydrate, a solvate, a crystal form, a tautomer, or a pharmaceutically acceptable salt thereof, wherein:

Ar is selected from the group consisting of optionally substituted aryl and optionally substituted heteroaryl;

wherein L is selected from the group consisting of single bond, —$CR^5(R^6)$—, —$CR^5(R^6)$—$CR^7(R^8)$— and —$C(R^5)$=$C(R^6)$—;

wherein $R^1$ and $R^2$ are the same or different from each other and are independently selected from the group consisting of H, F, Cl, Br, I, OH, optionally substituted alkyl, optionally substituted aryl, optionally substituted heteroalkyl and optionally substituted heteroaryl;

wherein $R^3$, $R^4$, $R^5$, $R^6$, $R^7$ and $R^8$ are the same or different from each other and are independently selected from the group consisting of H, F, Cl, Br, I, OH, optionally substituted alkyl and optionally substituted heteroalkyl;

wherein within each pair of groups $R^1/R^2$, $R^3/R^4$, $R^5/R^6$ and $R^7/R^8$, the two groups can be optionally joined together to form a carbocyclic or a heterocyclic ring, or can optionally represent =O;

or a pharmaceutical composition comprising said compound, or an enantiomer, a diastereoisomer, a hydrate, a solvate, a crystal form, a tautomer, or a pharmaceutically acceptable salt thereof, and a pharmaceutically acceptable excipient, to a subject in need thereof.

6. The method according to claim 5, wherein the route of administration is topical administration or systemic administration, and/or the method is a nonsurgical method.

7. The method of claim 1, wherein:

L is selected from the group consisting of single bond, —$CR^5(R^6)$—, —$CR^5(R^6)$—$CR^7(R^8)$— and —$C(R^5)$=$C(R^6)$—;

$R^3$, $R^4$, $R^5$, $R^6$, $R^7$ and $R^8$ are the same or different from each other and are independently selected from the group consisting of H, F, Cl, Br, I, OH, optionally substituted alkyl and optionally substituted heteroalkyl;

wherein within each pair of groups $R^3/R^4$, $R^5/R^6$ and $R^7/R^8$, the two groups can be optionally joined together to form a carbocyclic or a heterocyclic ring, or can optionally represent =O, and (i) when each of $R^1$ and $R^2$ is H; Ar is selected from the group consisting of aryl, optionally substituted alkoxyaryl, optionally substituted carboxyaryl, optionally substituted cyanoaryl, haloaryl, optionally substituted hydroxyaryl, optionally substituted alkoxyheteroaryl, optionally substituted cyanoheteroaryl, optionally substituted haloheteroaryl, optionally substituted heteroarylaryl, optionally substituted hydroxyheteroaryl and optionally substituted carboxyheteroaryl; or (ii) when $R^1$ and $R^2$ together represent =O; Ar is optionally substituted aryl selected from the group consisting of carboxyaryl, cyanoaryl, hydroxyaryl, heteroarylaryl, 1,3-benzodioxol-5-yl, 2,3-dichlorophenyl, 2,3-dihydro-1,4-benzodioxin-6-yl, 3-chloro-5-methoxyphenyl, 3-chlorophenyl, 3-fluorophenyl, 3-methoxyphenyl, 3,4,5-trifluorophenyl, 3,5-dichlorophenyl, 4-(benzyloxy)phenyl, 4-[2-(morpholin-4-yl)ethoxy]phen-1-yl, 4-butoxyphenyl, 4-chlorophenyl, 4-fluoro-3-methoxyphenyl, 4-fluorophenyl, 4-methoxyphenyl, biphenyl-3-yl, naphthalen-2-yl, and phenyl, or is optionally substituted heteroaryl selected from the group consisting of alkoxyheteroaryl, cyanoheteroaryl, haloheteroaryl, hydroxyheteroaryl and carboxyheteroaryl, or a pharmaceutical composition comprising said compound, or an enantiomer, a diastereoisomer, a hydrate, a solvate, a crystal form, tautomer, or a pharmaceutically acceptable salt thereof, and a pharmaceutically acceptable excipient,

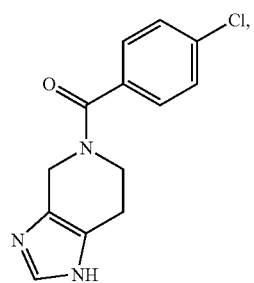 [SMILES: O=C(c1ccc(Cl)cc1)N1CCc2[nH]cnc2C1]

provided that the compound of Formula I is not to a subject in need thereof.

8. The method according to claim 7, wherein the compound of Formula I is not:

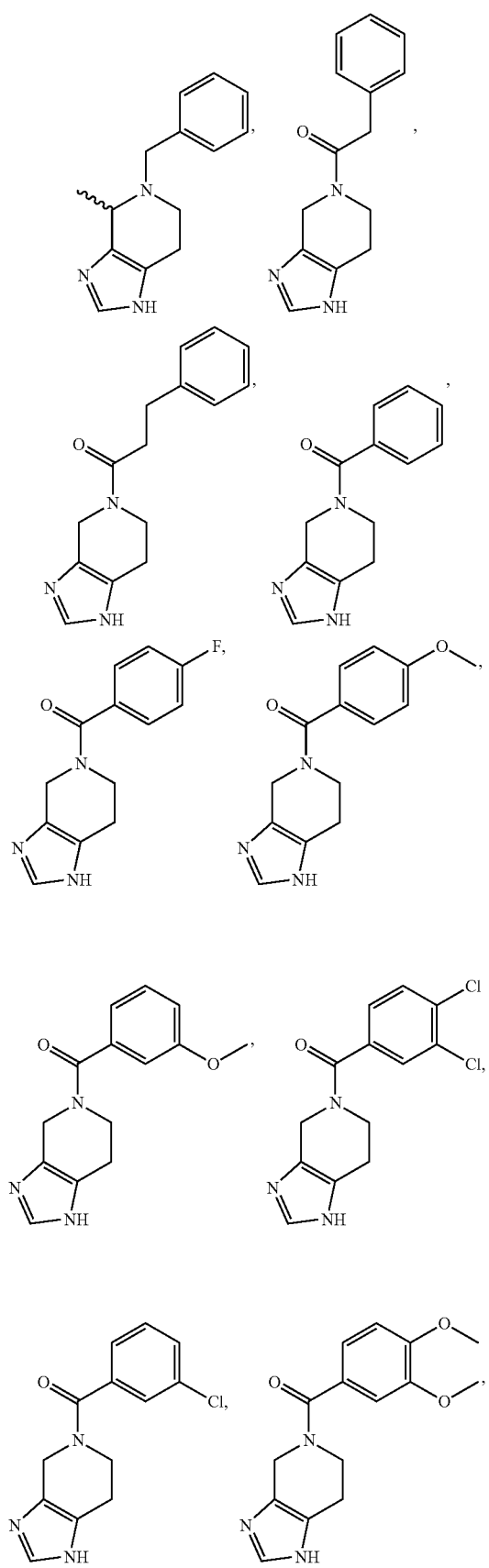
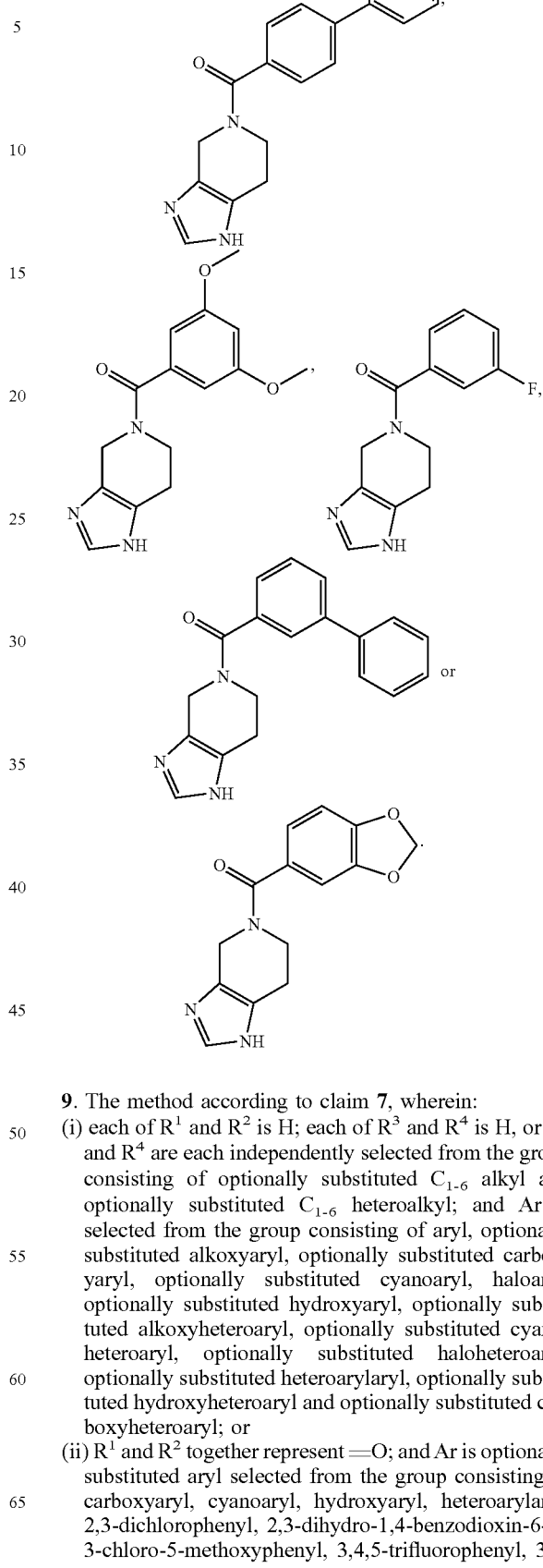

9. The method according to claim 7, wherein:
(i) each of $R^1$ and $R^2$ is H; each of $R^3$ and $R^4$ is H, or $R^3$ and $R^4$ are each independently selected from the group consisting of optionally substituted $C_{1-6}$ alkyl and optionally substituted $C_{1-6}$ heteroalkyl; and Ar is selected from the group consisting of aryl, optionally substituted alkoxyaryl, optionally substituted carboxyaryl, optionally substituted cyanoaryl, haloaryl, optionally substituted hydroxyaryl, optionally substituted alkoxyheteroaryl, optionally substituted cyanoheteroaryl, optionally substituted haloheteroaryl, optionally substituted heteroarylaryl, optionally substituted hydroxyheteroaryl and optionally substituted carboxyheteroaryl; or
(ii) $R^1$ and $R^2$ together represent =O; and Ar is optionally substituted aryl selected from the group consisting of carboxyaryl, cyanoaryl, hydroxyaryl, heteroarylaryl, 2,3-dichlorophenyl, 2,3-dihydro-1,4-benzodioxin-6-yl, 3-chloro-5-methoxyphenyl, 3,4,5-trifluorophenyl, 3,5- dichlorophenyl, 4-(benzyloxy)phenyl, 4-[2-(morpholin-4-yl)ethoxy]phen-1-yl, 4-butoxyphenyl, 4-fluoro-3-methoxyphenyl and naphthalen-2-yl, or is optionally substituted heteroaryl selected from the group consisting of alkoxyheteroaryl, cyanoheteroaryl, haloheteroaryl, hydroxyheteroaryl and carboxyheteroaryl.

10. The method according to claim 9, wherein when $R^1$ and $R^2$ together represent =O, $R^3$ and $R^4$ are each independently selected from group consisting of H, optionally substituted $C_{1-6}$ alkyl and optionally substituted $C_{1-6}$ heteroalkyl.

11. The method according to claim 10, wherein $R^3$ is methyl; and/or $R^4$ is selected from the group consisting of H and methyl.

12. The method according to claim 9, wherein each of $R^3$ and $R^4$ is methyl; or each of $R^3$ and $R^4$ is H.

13. The method according to claim 9, wherein L in Formula I is selected from the group consisting of a single bond, —$CR^5(R^6)$—, —$C(R^5)$=$C(R^6)$— and —$CR^5(R^6)$—$CR^7(R^8)$–.

14. The method according to claim 13, wherein in Formula I, $R^5$, $R^6$, $R^7$ and $R^8$ are the same or different from each other, and are independently selected from group consisting of H, OH, optionally substituted $C_{1-6}$ alkyl and optionally substituted $C_{1-6}$ heteroalkyl; or each of $R^5$, $R^6$, $R^7$ and $R^8$ is H.

15. The method according to claim 7, wherein Ar in Formula I is selected from the group consisting of: 1,3-benzodioxol-5-yl, 2,3-dichlorophenyl, 2,3-dihydro-1,4-benzodioxin-6-yl, 3-chloro-5-methoxyphenyl, 3,4,5-trifluorophenyl, 3,5-dichlorophenyl, 4-(benzyloxy)phenyl, 4-[2-(morpholin-4-yl)ethoxy]phen-1-yl, 4-butoxyphenyl, 4-fluoro-3-methoxyphenyl and naphthalen-2-yl.

16. The method according to claim 1, wherein in $R^3$ and $R^4$, said alkyl is selected from methyl, ethyl, propyl, butyl, pentyl, hexyl, heptyl, octyl, cyclobutyl, cyclopentyl, cyclohexyl and cyclooctyl.

17. The method according to claim 1, wherein $R^3$ is methyl and $R^4$ is H; or each of $R^3$ and $R^4$ is methyl; or each of $R^3$ and $R^4$ is H.

18. The method according to claim 5, wherein in $R^3$ and $R^4$, said alkyl is selected from methyl, ethyl, propyl, butyl, pentyl, hexyl, heptyl, octyl, cyclobutyl, cyclopentyl, cyclohexyl and cyclooctyl.

19. The method according to claim 5, wherein $R^3$ is methyl and $R^4$ is H; or each of $R^3$ and $R^4$ is methyl; or each of $R^3$ and $R^4$ is H.

20. The method according to claim 7, wherein in $R^3$ and $R^4$, said alkyl is selected from methyl, ethyl, propyl, butyl, pentyl, hexyl, heptyl, octyl, cyclobutyl, cyclopentyl, cyclohexyl, cycloheptyl and cyclooctyl.

* * * * *